(12) United States Patent
Markovitz et al.

(10) Patent No.: US 7,052,676 B2
(45) Date of Patent: May 30, 2006

(54) METHODS FOR INHIBITION OF HIV REPLICATION USING A SMALL MOLECULE INHIBITOR

(75) Inventors: David M. Markovitz, Ann Arbor, MI (US); Brian R. Lane, Ann Arbor, MI (US); Peter J. Polverini, Falcon Heights, MN (US); Robert M. Strieter, Sherman Oaks, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/961,696

(22) Filed: Sep. 20, 2001

(65) Prior Publication Data

US 2003/0026802 A1 Feb. 6, 2003

Related U.S. Application Data

(60) Provisional application No. 60/235,634, filed on Sep. 26, 2000.

(51) Int. Cl.
*A61K 49/00* (2006.01)
(52) U.S. Cl. ............................................. 424/9.2; 435/5
(58) Field of Classification Search ................. 424/9.2, 424/208.1; 435/5; 514/79, 80
See application file for complete search history.

(56) References Cited

U.S. PATENT DOCUMENTS 5,965,536 A * 10/1999 Cohen et al. .................. 514/17
6,140,338 A    10/2000 Naya et al.
2004/0022762 A1 * 2/2004 Dillon et al. .............. 424/85.2

OTHER PUBLICATIONS

Murayama et al. Potential involvement of IL-8 in the pathogenesis of human cytomegalovirus infection. Journal of Leukocyte Biology (1998) vol. 68, pp. 62-67.*
Howard et al. Inhibition of in vitro and in vivo HIV replication by distamycin analogue that interferes with the chemokine receptor function: a candidate for chemotherapeutic and microbicidal application. Journal of Medicinal Chemistry (1998) vol. 41, pp.*
"The CXC Chemokines Growth-regulated Oncogene (GRO) α, GROβ, GROγ, Neutrophil-activating Peptide-2, and Epithelial Cell-derived Neutrophil-activating Peptide-78 are Potent Agonists for the Type, B, but Not the Type A, Human Interlukin-8 Receptor", S.K. Ahuja et al., The Journal of Biological Chemistry, vol. 271, No. 34, Aug. 1996, pp. 20545-20550.
"CC CKR5: A Rantes, MIP-1α, MIP-1β Receptor as a Fusion Cofactor for Macrophage-Tropic HIV-1", G. Alkhatib et al., SCIENCE, vol. 272, Jun. 28, 1996, pp. 1955-1958.

"HIV Coreceptor Downregulation as Antiviral Principle: SDF-1α-dependent Internalization of the Chemokine Receptor CXCR4 Contributes to Inhibition of HIV Replication", A. Amara et al., J. Exp. Med., The Rockefeller University Press, vol. 186, No. 1, Jul. 1997, pp. 139-146.
"Constitutive overexpression of a growth-regulated gene in transformed Chinese hamster and human cells", A. Anisowicz et al., Proc. Natl. Acad. Sci. USA, vol. 84, Oct. 1987, pp. 7188-7192.
"Human herpesvirus KSHV encodes a constitutively active G-protein-coupled receptor linked to cell proliferation" L. Arvanitakis et al., NATURE, vol. 385, Jan. 1997, pp. 347-349.
"Kaposi's Sarcoma in the Gambia, West Africa is Less Frequent in Human Immunodeficiency Virus Type 2 than in Human Immunodeficiency Virus Type 1 Infection Despite a High Prevalence of Human Herpesvirus 8", K. Ariyoshi et al., Journal of Human Virology, vol. 1, No. 3, Mar./Apr. 1998, pp.; 193-199.
"Macrophage-dependent Apoptosis of CD4+ T Lymphocytes from HIV-infected Individuals is Mediated by FasL and Tumor Necrosis Factor", A. Badley et al., J. Exp. Med., The Rockefeller University Press, vol. 185, No. 1, Jan. 1997, pp. 55-64.
"G-protein-coupled receptor of Kaposi's sarcoma-associated herpesvirus is a viral oncogene and angiogensis activator", C. Bais et al., NATURE, vol. 391, Jan. 1998, pp. 86-69.
"The Tat protein of human immunodeficiency virus type 1, a growth factor for AIDS Kaposi sarcoma and cytokine-activated vascular cells, induces adhesion of the same cell types by using integrin receptors recognizing the RGD amino acid sequence", G. Barillari et al., Proc. Natl. Acad. Sci. USA, vol. 90, Sep. 1993, pp. 7941-7945.
"Kaposi's sarcoma among persons with AIDS: a sexually transmitted infection?", V. Beral et al., The Lancet, Medical Science, vol. 335, Jan. 1990, pp. 123-128.
"The lymphocyte chemoattractant SDF-1 is a ligand for LESTR/fusin and blocks HIV-1 entry", C. Bleul et al., NATURE, vol. 382, Aug. 1996, pp. 829-833.
"A Highly Efficacious Lymphocyte Chemoattractant, Stromal Cell-derived Factor 1 (SDF-1)", C. Bleul et al., J. Exp. Med., The Rockefeller University Press, vol. 184, Sep. 1996, pp. 1101-1109.

(Continued)

*Primary Examiner*—Ulrike Winkler
(74) *Attorney, Agent, or Firm*—Harness, Dickey & Pierce, P.L.C.

(57) ABSTRACT

Methods are provided for inhibiting or suppressing viral replication in an infected host cell. More specifically, methods are provided for inhibiting or suppressing viral replication in an infected host cell by administering compounds that interfere with the binding of C-X-C chemokines to C-X-C chemokine receptors. Such methods are advantageous for treating viral infections such as human immunodefeciency virus infections.

5 Claims, 39 Drawing Sheets

OTHER PUBLICATIONS

"Induction of Interleukin-10 by Human Immunodeficiency Virus Type 1 and its gp120 Protein in Human Monocytes/Macrophages", P. Borghi et al., Journal of Virology, Feb. 1995, pp. 1284-1287.

"Kaposi's sarcoma-associated herpesvirus infects endothelial and spindle cells" C. Boshoff et al., Nature Medicine, vol. 1, No. 12, Dec. 1995, pp. 1274-1278.

"Kaposi's Sarcoma-Associated Herpesvirus", C. Boshoff et al., Advances in Cancer Research, 1998, pp. 57-86.

"Clinical aspects of Kaposi's sarcoma", A. Buchbinder, MD et al., Cancer in AIDS, 1992 Current Science ISSN, Current Opinion in Oncology 1992, vol. 4, pp. 867-874.

"Regulation of HIV-1 Expression by Cytokine Networks in a $CD4^+$ Model of Chronic Infection", S. Butera et al., The Journal of Immunology, vol. 150, No. 2, Jan. 1993, pp. 625-634.

"Macrophage Inflammatory Protein-1α is Induced by Human Immunodeficiency Virus Infection of Monocyte-Derived Macrophages", B. Canque et al., BLOOD, vol. 87, No. 5, Mar. 1996, pp. 2011-2019.

"Inhibition of HIV Type 1 BaL Replication by MIP-1α, MIP-1β, and RANTES in Macrophages", M. Capobianci et al., Aids Research and Human Retroviruses, vol. 14, Nov. 3, 1998, pp. 233-240.

"Identification of Herpesvirus-Like DNA Sequences in AIDS-Associated Kaposi's Sarcoma" Y. Chang et al., SCIENCE, vol. 266, Dec. 1994, pp. 1865-1869.

"The β-Chemokine Receptors CCR3 and CCR5 Facilitate Infection by Primary HIV-1 Isolates", H. Choe et al., CELL, vol. 85, Jun. 1996, pp. 1135-1148.

"The HIV-1 gp120 Envelope Protein has the Intrinsic Capacity to Stimulate Monokine Secretion", K. Clouse et al., The Journal of Immunology, vol. 147, No. 9, Nov. 1991, pp. 2892-2900.

"Identification of RANTES, MIP-1α, and MIP-1β as the Major HIV-Suppressive Factors Produced by $CD8^+$ T Cells", F. Cocchi et al., SCIENCE, vol. 270, Dec. 1995, pp. 1811-1815.

"RANTES inhibits HIV-1 replication in human peripheral blood monocytes and alveolar macrophages", M. Coffey et al., The American Physiological Society, 1997, pp. L1025-L1029.

"Change in Coreceptor Use Correlates with Disease Progression in HIV-1 Infected Individuals", R. Connor et al., J. Exp. Med., The Rockefeller University Press, vol. 185, No. 4, Feb. 1997, pp. 621-628.

"Coordinate Enhancement of Cytokine Gene Expression in Human Immunodeficiency Virus Type 1-Infected Promonocytic Cells", M. D'Addario et al., Journal of Virology, vol. 64, No. 12, Dec. 1990, pp. 6080-6089.

"Expression of Human Herpesvirus 8-Encoded Cyclin D in Kaposi's Sarcoma Spindle Cells", M. Davis et al., Journal of the National Cancer Institute, vol. 89, No. 24, Dec. 1997, pp. 1868-1874.

"Genetic Restriction of HIV-1 Infection and Progression to AIDS by a Deletion Allete of the CKR5 Structural Gene", M. Dean et al., SCIENCE, vol. 273, Sep. 1996, pp. 1856-1862.

"Identification of a major co-receptor for primary isolates of HIV-1", H. Deng et al., NATURE, vol. 381, Jun. 1996, pp. 661-666.

"Dysregulation of Interleukin 8, Interleukin 10, and Interleukin 12 Release by Alveolar Macrophages from HIV Type 1-Infected Subjects", M. Denis et al., AIDS Research and Human Retroviruses, vol. 10, Nov. 1994, pp. 1619-1627.

"Increased replication of T-cell-tropic HIV strains and CXC-chemokine receptor-4 induction in T cells treated with macrophage inflammatory protein (MIP)-1α, MIP-1β and RANTESβ-chemokines", A. Dolei et al., AIDS 1998, vol. 12, No. 2 pp. 183-190.

"A Dual-Tropic Primary HIV-1 Isolate that Uses Fusin and the β-Chemokine Receptors CKR-5, CKR-3 and CKR-2b as Fusion Cofactors", B. Doranz et al., Cell, vol. 85, Jun. 1996, pp. 1149-1158.

"HIV-1 entry into $CD4^+$ cells is mediated by the chemokine receptor CC-CKR-5", T. Dragic et al., NATURE, vol. 381, Jun. 1996, pp. 667-673.

"Release, Uptake, and Effects of Extracellular Human Immunodeficiency Virus Type 1 Tat Protein on Cell Growth and Viral Transactivation", B. Ensoli et al., Journal of Virology, Jan. 1993, pp. 277-287.

"Synergy between basic fibroblast growth factor and HIV-1 Tat protein in induction of Kaposi's sarcoma", B. Ensoli et al., NATURE, vol. 371, Oct. 1994, pp. 674-680.

"Tat protein HIV-1 stimulates growth of cells derived from Kaposi's sarcoma lesions of AIDS patients", B. Ensoli et al., NATURE, vol. 345, May 1990, pp. 84-86.

"Individual Cell Analysis of the Cytokine Repretoire in Human Immunodeficiency Virus-1-Infected Monocytes/Macrophages by a Combination of Immunocytochemistry and In Situ Hybridization", R. Esser et al., BLOOD, vol. 91, No. 12, Jun. 1998, pp. 4752-4760.

"A Sensitive Elisa for the Detection of Human Monocyte Chemoattractant Protein-1 (MCP-1)", H. Evanoff et al., Immunological Investigations, 21(1), 1992, pp. 39-45.

"Multifactorial Nature of Human Immunodeficiency Virus Disease: Implications for Therapy", A. Fauci et al., SCIENCE, vol. 262, Nov. 1993, pp. 1011-1018.

"HIV-1 Entry Cofactor: Functional cDNA Cloning of a Seven-Transmembrane, G Protein-Coupled Receptor", Y. Feng et al., SCIENCE, vol. 272, May 1996, pp. 872-877.

"γ-Interferon Produced by $CD8^+$T Cells Infiltrating Kaposi's Sarcoma Induces Spindle Cells with Angiogenic Phenotype and Synergy with Human Imminodeficiency Virus-1 Tat Protein: An Immune Response to Human Herpesvirus-8 Infection?", V. Fiorelli et al., Blood, vol. 91, No. 3, Feb. 1998, pp. 956-967.

"Transformation of primary human endothelial cells by Koposi's sarcoma-associated herpesvirus", O. Flore et al., NATURE, vol. 394, Aug. 1998, pp. 588-592.

"Distinct Biology of Koposi's Sarcoma-Associated Herpesvirus from Primary Lesions and Body Cavity Lymphomas", J. Friborg, Jr. et al., Journal of Virology, vol. 72, No. 12, Dec. 1998, pp. 10073-10082.

"Disseminated Kaposi's Sarcoma in Homosexual Men", A. Friedman-Kien et al., Annals of Internal Medicine, Jun. 1982, vol. 96, No. 6 (Part 1), pp. 693-700.

"Disseminated Kaposi's sarcoma syndrome in young homosexual men", A. Friedman-Kien, Am Acad Dermatol, Journal of the American Academy of Dermatology, vol. 5, No. 4, Oct. 1981, pp. 468-471.

"The Engimas of Kaposi's Sarcoma", R. Gallo, SCIENCE, vol. 282, Dec. 1998, pp. 1837-1839.

"HIV Infection and Dementia", S. Gartner, SCIENCE, vol. 287, Jan. 2000, pp. 602-604.

"The Role of Mononuclear Phagoscytes in HTLV-III/LAV Infection", S. Gartner et al., SCIENCE, vol. 233, Jul. 1986, pp. 215-219.

"Seroconversion to Antibodies Against Kaposi's Sarcoma-Associated Herpesvirus-Related Latent Nuclear Antigens Before the Development of Kaposi's Sarcoma", S.J. Gao, Ph.D., et al, The New England Journal of Medicine, vol. 335, No. 4, Jul. 1996, pp. 233-241.

"Chemokines Activate Kaposi's Sarcoma-associated Herpesvirus G Protein-coupled Receptor in Mammalian Cells in Culture", M. Gershengorn et al., J. Clin. Invest., Rapid Publication, vol. 102, No. 8, Oct. 1998, pp. 1469-1472.

"MCP-1 and IL-8 trigger firm adhesion of monocytes to vascular endothelium under flow conditions", R. Gerszten et al., NATURE, vol. 398, Apr. 1999, pp. 718-723.

"Enhancement of Human Immunodeficiency Virus Type 1 Infection by the CC-Chemokine RANTES is Independent of the Mechanism of Virus-Cell Fusion", C. Gordon et al., Journal of Virology, Jan. 1999, pp. 684-694.

"Kaposi's Sarcoma: An Extensively Disseminated Form in Young Homosexual Men", G. Gottlieb et al., Human Pathology, vol. 13, No. 10, Oct. 1982, pp. 882-892.

"Patterns and Emerging Mechanisms of the Angiogenic Switch during Tumoringenesis", D. Hanahan et al., CELL, vol. 86, Aug. 1996, pp. 353-364.

"Apoptosis of $CD8^+$ T cells is mediated by macrophages through interaction of HIV gp 120 with chemokine receptor CXCR4", G. Herbein et al., NATURE, vol. 395, Sep. 1998, pp. 189-193 & 117.

"HIV-1 induces tumor necrosis factor and IL-1 gene expression in primary human macrophages independent of productive infection", G. Herbein et al., Clin. Exp. Immunol., 1994, 95:442-449.

"HIV-1 tat protein induces the production of interleukin-8 by human brain-derived endothelial cells", F. Hofman et al., Journal of Neuroimmunology, 94, 1999, pp. 28-39.

"Mononuclear Cell Adherence Induces Neutrophil Chemotactic Factor/Interleukin-8 Gene Expression", K. Kasahara et al., Journal of Leukocyte Biology 50:287-295 (1991).

"Highly Porous Polymer Matrices as a Three-Dimensional Culture System for Hepatocytes", P. Kaufmann et al., Cell Transplantation, vol. 6, No. 5, 1997, pp. 463-468.

"Cutting Edge: Dichotomous Effects of β-Chemokines on HIV Replication in Monocytes and Monocyte-Derived Macrophages", M. Kelly et al., CUTTING EDGE, The Journal of Immunology, 1998, pp. 3091-3095.

"CC-chemokines enhance the replication of T-tropic strains of HIV-1 in CD4+ T Cells: Role of signal transduction", A. Kinter et al., Proc. Natl. Acad. Sci. USA, vol. 95, pp. 11880-11885, Sep. 1998.

"Interleukin-8 as a Macrophage-Derived mediator of Angiogenesis", A. Koch et al., SCIENCE, vol. 258, Dec. 1992, pp. 1798-1801.

"Reduced Binding and Phagocytosis of Pneumocystis Carinii by Alveolar Macrophages from Persons Infected with HIV-1 Correlates with Mannose Receptor Downregulation", H. Koziel et al., J. Clin. Invest., vol. 102, No. 7, Oct. 1998, pp. 1332-1344.

"Activation of Monocytes by HIV-Tat Treatment is Mediated by Cytokine Expression", R. Lafrenie et al., The Journal of Immunology, 1997, pp. 4077-4083.

"TNF-α Inhibits HIV-1 Replication in Peripheral Blood Monocytes and Alveolar Macrophages by Inducing the Production of RANTES and Decreasing C-C Chemokine Receptor 5 (CCR5) Expression", B.R. Lane, et al., The Journal of Immunology, 1999, pp. 3654-3661.

"Leukotriene $B_4$ and Interleukin-8 in Human Immunodeficiency Virus-related Pulmonary Disease", G.Y. Lipschik, M.D., et al., CHEST, vol. 104, No. 3, Sep. 1993, pp. 763-769.

"Homozygous Defect in HIV-1 Coreceptor Accounts for Resistance of Some Multiply-Exposed Individuals to HIV-1 Infection", Rong Liu, et al., CELL, vol. 86, Aug. 1996, pp. 367-377.

Mechanism and biological significance of constitutive expression of MGSA/GRO chemokines in malignant melanoma tumor progression, Jing Luan, et al., Journal of Leukocyte Biology, vol. 62, Nov. 1997, pp. 588-597.

"Chemokines and their Receptors in Lymphocyte Traffic and HIV Infection", P. Loetscher, et al., Advances in Immunology, vol. 74, 2000, pp. 127-157.

"Aminooxypentane-RANTES Induces CCR5 Internatlization but Inhibits Recycling: A Novel Inhibitory Mechanism of HIV Infectivity", M. Mack, et al., J. Exp. Med., vol. 187, No. 8, Apr. 1998, pp. 1215-1224.

"Effect of Cytokines on HIV Replication in $CD4^+$ Lymphocytes: Lack of Identity with the $CD8^+$ Cell Antiviral Factor", C.E. Mackewicz et al., Cellular Immunology, vol. 153, 1994, pp. 329-343.

"Opposite Effects of SDF-1 on Human Immunodeficiency Virus Type 1 Replication", V. Marechal, et al., Journal of Virology, May 1999, pp. 3608-3615.

"Blockage of CC Chemokine Receptor 5 (CCR5)—Tropic Human Immunodeficiency Virus-1 Replication in Human Lymphoid Tissue by CC Chemokines", L.B. Margolis, et al., The Journal of Clinical Investigation, vol. 101, No. 9, May 1998, pp. 1876-1880.

"Activation of the Human Immunodeficiency Virus Type 1 Enhancer is not Dependent of NFAT-1", D.M. Markovitz, et al., Journal of Virology, Jun. 1992, pp. 3961-3965.

"Elevated serum levels of IL-8 in patients with HIV infection", T. Matsumoto, et al., Clin. Exp. Immunol, 1993 93:149-151.

"Early Lesions of Kaposi's Sarcoma in Homosexual Men—An Ultrastructural Comparison with Other Vascular Proliferations in Skin", N.S. McNutt, M.D., et al., Ultrastructure of Kaposi's Sarcoma, vol. III, No. 1, pp. 62-77.

"Role of Mononuclear Phagocytes in the Pathogenesis of Human Immunodeficiency Virus Infection", M.S. Meltzer, et al., Annu. Rev. Immunol. 1990, pp. 169-194.

"Tumor Necrosis Factor Alpha, Interleukin 1 and Related Cytokines in Brain Development: Normal and Pathological", Jean E. Merrill, REVIEW Dev. Neurosci, 1992; 14, pp. 1-10.

"Inflammatory Reactivation and Angigenicity of Kaposi's Sarcoma-Associated Herpesvirus? HHV8: A Missing Link in the Pathogensis of Acquired Immunodeficiency Syndrome-Associated Kaposi's Sarcoma", Enrique A. Mesri, *BLOOD*, vol. 93, No. 12, pp. 4031-4033.

"Antibodies to Butyrate-Inductible Antigens of Kaposi's Sarcoma-Associated Herpesvirus in Patients with HIV-1 Infection", G. Miller, M.D., et al., The New England Journal of Medicine, May 16, 1996, pp. 1292-1297.

"The Incidence of AIDS-Defining Illnesses in 4883 Patients with Human Immunodeficiency Virus Infection", A. Mocroft, Ph.D., et al., Arch Intern Med, vol. 158, Mar. 1998, pp. 491-497.

"Factors Secreted by Human T Lymphotropic Virus Type I (HTLV-I)-infected Cells Can Enhance or Inhibit Replication of HIV-1 in HTLV-I-uninfected Cells: Implications for In "Vivo Coinfection with HTLV-I and HIV-1", H. Moriuchi et al., The Journal of Experimental Medicine, vol. 187, No. 10, May 1998, pp. 1689-1697.

"Exposure to Bacterial Products Renders macrophages Highly Susceptible to T-Tropic HIV-1", M. Moriuchi et al., The Journal of Clinical Investigation, vol. 102, No. 8, Oct. 1998, pp. 1540-1550.

"Neutrophil-Activating Properties of the Melanoma Growth-Stimulatory Activity", B. Moser, J. Exp. Med., The Rockefeller University Press, vol. 171, May. 1990, pp. 1797-1802.

"Long-Term Infection and Transformatin of Dermal Microvascular Endothelial Cells by Human Herpesvirus8", A. V. Moses, et al., Journal of Virology, Aug. 1999, pp. 6892-6902.

"Enhanced HIV-1 Replication by Chemokines Constitutively Expressed in Secondary Lymphoid Tissues", M. Nagira et al., VIROLOGY, vol. 264, 1999, pp. 422-426.

"Induction of IL-6 (B Cell Stimulatory Factor-2IFN-$\beta_2$) Production by HIV$^1$", K. Nakajima et al., The Journal of Immunology, vol. 142, No. 2, Jan. 1989, pp. 531-536.

"Vascular Endothelial Growth Factor (VEGF)-Mediated Angiofenesis is Associated with Enhanced Endothelial Cell Survival and Induction of Bcl-2 Expression", J. E. Nör et al., American Journal of Pathology, vol. 154, No. 2, Feb. 1999, pp. 375-384.

"The CXC chemokine SDF-1 is the ligand for LESTR/fusin and prevents infection by T-cell-line-adapted HIV-1", E. Oberlin et al., NATURE, vol. 382, Aug. 1996, pp. 833-835.

"Identification of HIV-1 Envelope Glycoprotein in the Serum of AIDS and ARC Patients", Se-Kyung Oh et al., Journal of Acquired Immune Deficiency Syndromes, vol. 5, No. 3, 1992, pp. 251-256.

"Superinduction of IL-8 in T Cells by HIV-1 Tat Protein Is Mediated Through NF-κB Factors", M. Ott et al., The American Association of Immunologists, 1998, pp. 2873-2880.

"Role of Cytokines in the Pathogenesis of Human Immunodeficeincy Virus Infection", Guido Poli et al., Human Cytokines: Their Role in Disease and Therapy, pp. 421-449.

"Cytokine modulation of HIV expression", G. Poli et al., Seminars in IMMUNOLOGY, vol. 5, 1993, pp. 165-173.

"Assay and Purification of Naturally Occurring Inhibitor of Angiogenesis", Peter J. Polverini et al., Methods in Enzymology, vol. 198, 1991, pp. 440-450.

"Replication of HIV-1 in Primary Monocyte Cultures", B. J. Potts et al., VIROLOGY, 175, 1990, pp. 465-476.

"HIV positive patients first presenting with an AIDS defining illness: characteristics and survival", M.C. Poznanasky et al., BMJ, 1995, 311, pp. 156-158.

"Human Kaposi's Sarcoma Cell-Mediated Tumorigenesis in Human Immunodeficiency Type 1 Tat-Expressing Transgenic Mice", O. Prakash et al., Journal of the National Cancer Institute, vol. 92, May 2000, pp. 721-728.

"Human Immunodeficiency Virus-Associated Oral Kaposi's Sarcoma", J. Regezi et al., American Jouranal of Pathology, vol. 143, No. 1, Jul. 1993, pp. 240-249.

"Lytic growth of Kaposi's sarcoma-associated herpesvirus (human herpesvirus 8) in culture", R. Renne et al., Nature Medicine, vol. 2, No. 3, Mar. 1996, pp. 342-346.

"Human Herpesvirus 8 Seropositivity and Risk of Koposi's Sarcoma and Other Acquired Immunodeficiency Syndrome-Related Diseases", G. Rezza et al., Journal of the National Cancer Institute, vol. 91, No. 17, Sep. 1999, pp. 1468-1474.

"Purification of Melanoma Growth Stimulatory Activity", A. Richmond et al., Journal of Cellular Physiology, vol. 129, 1986, pp. 375-384.

"Resistance of HIV-1 infection in Caucasian individuals bearing mutant alleles of the CCR-5 chemokine receptor gene", M. Samson et al., NATURE, vol. 382, Aug. 1996, pp. 722-725.

"Human Immunodeficiency Virus Type 1 T-Lymphotropic Strains Enter Macrophages via a CD4- and CXCR4-Mediated Pathway: Replication is Restricted at a Postentry Level", H. Schmidtmayerova et al., Journal of Virology, vol. 72, No. 6, Jun. 1998, pp. 4633-4642.

"Human immunodeficiency virus type 1 infection alters chemokine β peptide expression in human monocytes: Implications for recruitment of leukocytes into brain and lymph nodes", H. Schmidtmayerova et al., Proc. Natl. Acad. Sci. USA, vol. 93, Jan. 1996, pp. 700-704.

"Mechanism of Paclitaxel Activity in Kaposi's Sarcoma", C. Sgadari, et al., The American Association of Immunologists, 2000, pp. 509-516.

"Modulation of the Effector Function of Human Monocytes for Mycobacterium avium by Human Immunodeficiency Virus-1 Envelope Glycoprotein gp 120", H. Shiratsuchi et al., J. Clin. Invest., vol. 93, Feb. 1994, pp. 885-891.

"CXCR4 as a Functional Coreceptor for Human Immunodeficiency Virus Type 1 Infection of Primary Macrophages", G. Simmons et al., Journal of Virology, Oct. 1998, pp. 8453-8457.

"Contrasting Genetic Influence of CCR2 and CCR5 Variants on HIV-1 Infection and Disease Progression", M. W. Smith et al., SCIENCE, vol. 277, Aug. 1997, pp. 959-965.

"The epidemiology of HIV-associated Kaposi's sarcoma: the unraveling mystery", S.A. Strathdee et al., AIDS 1996, vol. 10, pp. S51-S57.

"The Functional Role of the ELR Motif in CXC Chemokine-mediated Angiogenesis", R.M. Strieter et al., The Journal of Biological Chemistry, vol. 270, No. 45, Issue of Nov. 10, pp. 27348-27357.

"The CC-Chemokine RANTES Increases the Attachment of Human Immunodeficiency Virus Type 1 to Target Cells via Glycosaminoglycans and Also Activates a Signal Transduction Pathway that Enhances Viral Infectivity", A. Trkola et al., Journal of Virology, Aug. 1999, pp. 6370-6379.

"CD4-dependent, antibody-sensitive interactions between HIV-1 and its co-receptor CCR-5", A. Trkola et al., NATURE, vol. 384, Nov. 1996, pp. 184-187.

"Cutting Edge: CXCR4 is a Functional Coreceptor for Infection of Human Macrophages by CXCR4-Dependent Primary HIV-1 Isolates", A. Verani et al., The Journal of Immunology, 1998, pp. 2084-2088.

"GRO Alpha and Interleukin-8 in Pneumocystis carinii or Bacterial Pneumonia and Adult Respiratory Distress Syndrome", J. Villard et al., American Journal of Respiratory and Critical Care Medicine, vol. 152, 1995, pp. 1549-1554.

"Chemokines and T Lymphocytes: More than an Attraction", S. G. Ward et al., IMMUNITY, vol. 9, Jul. 1998, pp. 1-11.

"Current pathologic methods for measuring intratumoral microvessel density within breast carcinoma and other solid tumors", N. Weidner, Breast Cancer Research and Treatment, vol. 36, 1995, pp. 169-180.

"Tumor Angiogenesis and Metastasis—Correlation in Invasive Breast Carcinoma", N. Weidner et al., The New England Journal of Medicine, vol. 324, No. 1, Jan. 1991, pp. 1-8.

"Genetic Restriction of AIDS Pathogenesis by an SDF-1 Chemokine Gene Variant", C. Winkler et al., SCIENCE, vol. 279, Jan. 1998, pp. 389-392.

"CD4-induced interaction of primary HIV-1 gp120 glycoproteins with the chemokine receptor CCR-5", L. Wu et al., NATURE, vol. 384, Nov. 1996, pp. 179-183.

"Intracellular CXCR4 signaling, neuronal apoptosis and neuropathogenic mechanisms of HIV-1 associated dementia", J. Zheng et al., Journal of Neuroimmunolgy, vol. 98, 1999, pp. 185-200.

"Interleukin-1 and Tumor Necrosis Factor α Can Be Induced from Mononuclear Phagocytes by Human Immunodeficiency Virus Type 1 Binding to the CD4 Receptor", J.E. Merrill, et al., Journal of Virology, vol. 63, No. 10, Oct. 1989, pp. 4404-4408.

John R. White et al., "Identification of a Potent, Selective Non-peptide CXCR2 Antagonist That Inhibits Interleukin-5-induced Neutrophil Migration," J. Biological Chemistry, vol. 273, No. 17, pp. 10095-10098 (Apr. 24, 1996.

Tatjans Dragic et al., "A binding pocket for a small molecule inhibitor of HIV-1 entry within the transmembrane helices of CCR5," PNAS, vol. 97, No. 10, pp. 5639-5644 (May 9, 2000).

* cited by examiner

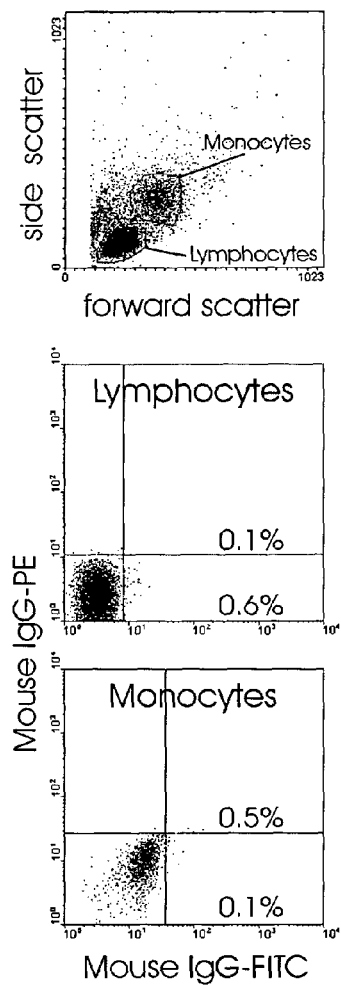
FIG. 7A
FIG. 7B
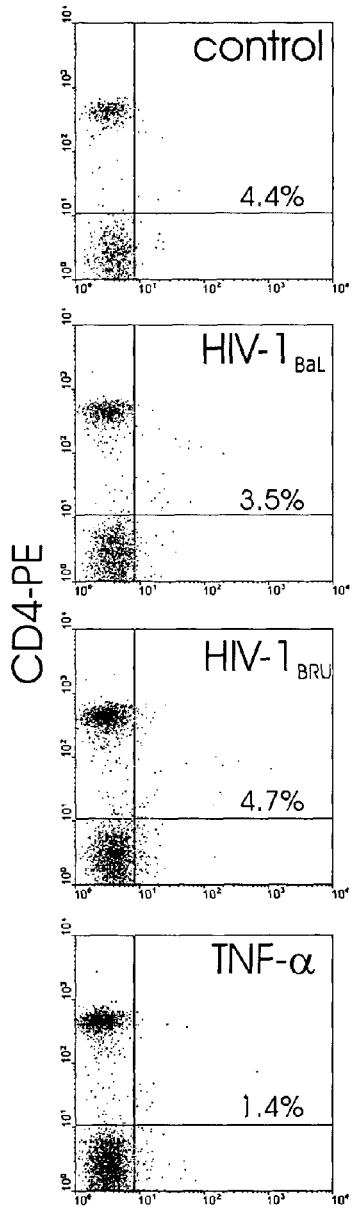
FIG. 7C
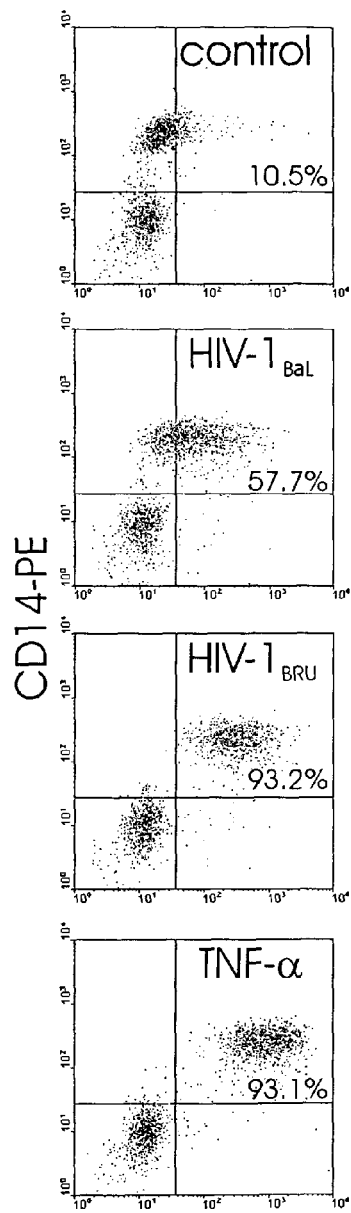

FIGURES 15A-D

METHODS FOR INHIBITION OF HIV REPLICATION USING A SMALL MOLECULE INHIBITOR

This application claims the benefit of Provisional 60/235,634 filed Sep. 26, 2000.

SPONSORSHIP

Work on this invention was sponsored in part by National Institutes of Health Grant AI36685. The Government may have certain rights in the invention.

BACKGROUND OF THE INVENTION

Medical therapy for infection with the human immunodeficiency virus type 1 (HIV-1) has improved over the last several years. However, many patients still fail to respond to the available pharmacologic agents, due to drug resistance and other factors. In addition, the antivirals currently available are often not well tolerated by patients.

The currently available drugs for treating HIV-1 infection either attack the reverse transcriptase or protease enzymes of the virus. Such compounds have the problem of rapidly developing drug resistance due to rapid transformation of the infecting viral genome. However, despite the problem of rapid drug resistance such drugs have been used to treat HIV seropositive individuals to help prevent the progression of the infection into the clinical symptoms of acquired immunodeficiency syndrome (AIDS). Such drugs are also used to obtain regression of AIDS.

Infection of CD4+ T lymphocytes and monocyte-derived macrophages (MDM) by the human immunodeficiency virus type 1 (HIV-1) triggers the production and release of inflammatory mediators. Butera, S. T. et al., *J Immunol* 150, 625–34 (1993); D'Addario, M. et al., *J Virol* 64, 6080–9 (1990); Nakajima, K. et al., *J Immunol* 142, 531–6 (1989); Poli, G. et al. and Fauci, *Semin Immunol* 5, 165–73 (1993); Meltzer, *Annu Rev Immunol* 8, 169–194 (1990). These cytokines have been shown to participate in the host defense against HIV-1, but also contribute to the pathogenesis of HIV-1 infection. Fauci, A. S., *Science* 262, 1011–8 (1993). A subset of the cytokine family, the chemokines, are a group of small polypeptide molecules that attract and activate leukocytes via interactions with seven-transmembrane-domain G-protein-coupled-receptors (GPCR) Loetscher, P. et al., *Adv Immunol* 74, 127–80 (2000). The chemokines are divided into subgroups according to the position of the first two cysteine residues in their sequence. C-C chemokines act primarily on mononuclear cells, including macrophages and lymphocytes. While initially characterized by their ability to attract neutrophils, some C-X-C chemokines have been shown to attract activated T cells, act as angiogenic regulators, and to stimulate monocyte adherence. Gerszten, R. E. et al., *Nature* 398, 718–23 (1999); Strieter, R. M. et al., *J Biol Chem* 270, 27348–57 (1995); Ward, S. G. et al., *Immunity* 9, 1–11 (1998).

Chemokines and chemokine receptors have recently come to the forefront of HIV biology. In the past few years, it has been shown that the C-C chemokines RANTES, MIP-1α and MIP-1β suppress HIV replication Cocchi, F. et al., *Science* 270, 1811–1815 (1995); Coffey, M. J. et al., *Am J Physiol* 272, L1025–9 (1997), although under some circumstances these same chemokines can actually enhance HIV-1 replication. Dolei, A. et al., *Aids* 12, 183–190 (1998); Gordon, C. J. et al., *J Virol* 73, 684–94 (1999); Kelly, M. D. et al., *J Immuno* 160, 3091–5 (1998); Kinter, A. et al., *Proc Natl Acad Sci USA* 95, 11880–11885 (1998); Marechal, V. et al., *J Virol* 73, 3608–15 (1999); Margolis, L. B. et al., *J Clin Invest* 101, 1876–80 (1998); Moriuchi, H. et al., *J Exp Med* 187, 1689–97 (1998); Moriuchi, M. et al., *J Clin Invest* 102, 1540–1550 (1998); Schmidtmayerova, H. et al., *Proc Natl Acad Sci USA* 93, 700–704 (1996); Trkola, A. et al., *J Virol* 73, 6370–9 (1999). It is now well known that HIV-1 enters cells by binding first to the CD4 receptor, which induces a conformational change in gp120, and then to a second receptor, which exposes the fusogenic epitopes of gp41 and permits fusion with the host cell membrane and subsequent entry into the cell. It has been shown that the major co-receptor for T cell tropic HIV-1 is the C-X-C chemokine receptor CXCR4, the ligand for which is SDF-1α. Bleul, C. C. et al., *Nature* 382, 829–33 (1996); Bleul, C. C. et al., *J Exp Med* 184, 1101–9 (1996); Feng, Y. et al., *Science* 272, 872–7 (1996). The principal co-receptor for monocytotropic HIV-1 isolates has been identified as CCR5, a C-C chemokine receptor that has as its ligands RANTES, MIP-1α and MIP-1β. Alkhatib, G. et al., *Science* 272, 1955–1958 (1996); Choe, H. et al., *Cell* 85, 1135–48 (1996); Deng, H. et al., *Nature* 381, 661–6 (1996); Doranz, B. J. et al., *Cell* 85, 1149–58 (1996); Dragic, T. et al., *Nature* 381, 667–73 (1996). It has been demonstrated that individuals having mutations in both alleles for CCR5 are highly resistant to HIV infection. Dean, M. et al., *Science* 273, 1856–62 (1996); Liu, R. et al., *Cell* 86, 367–77 (1996); Samson, M. et al., *Nature* 382, 722–5 (1996). Further, some evidence indicates that persons heterozygous for a mutation in CCR5 have a delayed clinical course following HIV infection Dean, M. et al., Science 273, 1856–62 (1996); Samson, M. et al., *Nature* 382, 722–5 (1996); Smith, M. W. et al., *Science* 277, 959–65 (1997). A polymorphism in the gene for SDF-1α has also been associated with slower disease progression in HIV-1-infected individuals (Winkler, C. et al., *Science* 279, 389–93 (1998)), and SDF-1α blocks entry by CXCR4-using (X4) isolates of HIV. Bleul, C. C. et al., *Nature* 382, 829–33 (1996); Bleul, C. C. et al., *J Exp Med* 184, 1101–9 (1996); Oberlin, E. et al., *Nature* 382, 833–835 (1996). However, like RANTES, SDF-1α can actually potentiate HIV-1 replication under certain circumstances. Marechal, V. et al., *J Virol* 73, 3608–15 (1999).

The role that other chemokines play in HIV pathogenesis has been little studied. IL-8, the prototypical member of the C-X-C chemokine family, has been extensively characterized as a chemotactic factor for neutrophils. Loetscher, P. et al., *Adv Immunol* 74, 127–80 (2000); Yoshimura, T. et al., *Proc Natl Acad Sci USA* 84, 9233–7 (1987). Elevated levels of IL-8 have been detected in the serum and lungs of HIV-infected individuals. Denis, M. et al., *AIDS Res Hum Retroviruses* 10, 1619–27 (1994); Lipschik, G. Y. et al., *Chest* 104, 763–9 (1993); Matsumoto, T. et al., *Clin Exp Immunol* 93, 149–51 (1993). The presence of elevated levels of IL-8 in individuals infected with HIV-1 has led several groups to suggest that IL-8 plays a role in the pathogenesis of HIV-1 disease and infection with opportunistic infections, but little evidence has been found to support these claims.

Chemokine receptors are seven transmembrane domain-containing G-protein coupled receptors (GPCR) that transmit signals induced by a family of small, secreted polypeptides collectively known as chemokines. Chemokines attract and activate leukocytes and are divided into subgroups according to the position of the first two cysteine residues. Ward, S. G. et al., *Immunity* 9, 1–11 (1998). C-C chemokines act primarily on mononuclear cells, including MDM, lymphocytes, and eosinophils. Ward, S. G. et al., *Immunity* 9, 1–11 (1998). While initially thought to act principally on neutrophils, some C-X-C chemokines have been shown to attract activated T cells, act as angiogenic regulators, and stimulate monocyte adherence. Ward, S. G. et al., *Immunity* 9, 1–11 (1998); Strieter, R. M. et al, *J Biol Chem* 270, 27348–27357 (1995); Gerszten, R. E. et al., *Nature* 398, 718–723 (1999).

The C-X-C chemokine growth-regulated oncogene-alpha (GRO-α), also called melanoma growth stimulatory activity (MGSA), was initially identified as an autocrine growth factor for malignant melanoma cells. Richmond, A. et al., *J Cell Physiol* 129, 375–384 (1986). Subsequent studies have shown that the receptor for GRO-α is CXCR2, and GRO-α attracts cells that express this receptor, including both neutrophils and dendritic cell. Anisowicz, A. L. et al., *Proc Natl Acad Sci USA* 84, 7188–7192 (1987); Moser, B. et al, *J Exp Med* 171, 1797–1802 (1990); Ahuja, S. K. et al., *J Biol Chem* 271, 20545–20550 (1996). GRO-α also has been demonstrated to have direct angiogenic activity in several in vivo assays, and to activate orf 74 of the Kaposi's sarcoma herpesvirus (KSHV), a GPCR that has been implicated in the transformation and angiogenic phenotype of KS lesions. Strieter, R. M. et al., *J Biol Chem* 270, 27348–27357 (1995); Luan, J. et al., *J Leukoc Biol* 62, 588–597(1997); Gershengorn, M. C. et al., *J Clin Invest* 102, 1469–1472 (1998); Bais, C. et al., *Nature* 391, 86–89 (1998). GRO-α and the two other GRO chemokines, GRO-β and GRO-γ, are encoded by distinct genes, are 88% identical at the amino acid level, signal through CXCR2, and are thought to be largely functionally redundant. Ahuja, S. K. et al., *J Biol Chem* 271, 20545–20550 (1996); Luan, J. et al., *J Leukoc Biol* 62, 588–597 (1997).

Aberrant function of both infected and uninfected MDM has been implicated in the pathogenesis of HIV dementia and AIDS-associated opportunistic infections. Merrill, J. E., *Dev Neurosci* 14, 1–10 (1992); Shiratsuchi, H. et al., *J Clin Invest* 93, 885–891 (1994); Koziel, H. Q. et al., *J Clin Invest* 102, 1332–1344 (1998); Gartner, S., *Science* 287, 602–604 (2000). MDM infected with HIV-1 are known to produce a host of inflammatory mediators, including TNF-α, IL-1, and IL-6, less than 48 hours after infection. Merrill, J. E. et al., *J Virol* 63, 4404–4408 (1989); Clouse, K. A. et al., *J Immunol* 147, 2892–2901 (1991); Herbein, G. et al., *Clin Exp Immunol* 95, 442–449 (1994); Borghi, P. et al., *J Virol* 69, 1284–1287 (1995); Poli, G. et al., Cambridge, Mass.: *Blackwell Scientific*, pp. 421–449 (1995). In addition, macrophages exposed to HIV-1 contribute to the death of T lymphocytes by TNF-α- and FasL-dependent pathways. Badley, A. D. et al., *J Exp Med* 185, 55–64 (1997); Herbein, G. et al., *Nature* 395:189–194 (1998). Following infection, macrophages also produce the C-C chemokines RANTES, MIP-1α, and MIP-1β. Canque, B. et al., *Blood* 87, 2011–2019 (1996); Schmidtmayerova, H. et al., *Proc Natl Acad Sci USA* 93, 700–704 (1996). These three chemokines inhibit HIV replication by nature of their ability to ligate the HIV co-receptor CCR5 and prevent HIV entry, both by blocking binding sites and inducing receptor internalization. Cocchi, F. et al., *Science* 270, 1811–1815 (1995); Trkola, A. et al., *Nature* 384, 184–187 (1996); Wu, L. et al., *Nature* 384, 179–183 (1996); Coffey, M. J. et al., *Am J Physiol* 272, L1025–1029 (1997); Mack, M. et al., *J Exp Med* 187, 1215–1224 (1998). Subsequent reports have demonstrated that RANTES can also stimulate the replication of X4 HIV by activating, and increasing virion attachment to, target cells. Kinter, A. et al., *Proc Natl Acad Sci USA* 95, 11880–11885 (1998); Dolei, A. et al., *Aids* 12, 183–190 (1998); Gordon, C. J. et al., *J Virol* 73, 684–694 (1999); Trkola, A. et al., *J Virol* 73, 6370–6379 (1999). Similarly, the CXCR4 ligand SDF-1 can both prevent X4 HIV entry by inducing receptor internalization and stimulate HIV proviral gene expression. Bleul, C. C. et al., *Nature* 382, 829–833 (1996); Oberlin, E. et al., *Nature* 382, 833–835 (1996); Amara, A. et al., *J Exp Med* 186, 139–146 (1997); Marechal, V. et al., *J Virol* 73, 3608–3615 (1999). While much is known about the role of RANTES, MIP-1α, and MIP-1β in HIV pathogenesis, relatively little is known about the role of other chemokines produced by HIV-infected leukocytes.

Kaposi's sarcoma (KS) is one of the two most common neoplasms associated with HIV-1 infection and is difficult to treat clinically. Boshoff, C. et al., *Adv Cancer Res* 75, 57–86 (1998). KS is characterized by complex spindle cell neoplasms, composed of endothelial cells, fibroblasts, dermal dendrocytes, and inflammatory cells. Friedman-Kien, A. E., *J Am Acad Dermatol* 5, 468–71 (1981); Gottlieb, G. J. et al., *Hum Pathol* 13, 882–92 (1982); McNutt, N. S. et al., *Am J Pathol* 111, 62–77 (1983). In the early stages of disease, KS is not a monoclonal tumor, but an angioproliferative lesion driven by inflammatory cytokines. Fiorelli, V. et al., *Blood* 91, 956–67 (1998); Regezi, J. A. et al., *Am J Pathol* 143, 240–9 (1993). Although the origin of KS is still controversial, mounting evidence suggests that endothelial cells are the progenitors of the KS spindle cells. Boshoff, C. et al., *Nat Med* 1, 1274–8 (1995); Boshoff, C. et al., *Adv Cancer Res* 75, 57–86 (1998). Since Chang and coworkers first reported that over 90% of AIDS-KS tissue samples were positive for a new member of the γ-herpesvirus family, the Kaposi's sarcoma-associated herpesvirus (KSHV), also called human herpesvirus-8 (HHV-8), KSHV is believed to be necessary for the development of KS. Chang, Y. et al., *Science* 266, 1865–9 (1994); Gallo, R. C., *Science* 282, 1837–9 (1998); Mesri, E. A., *Blood* 93, 4031–3 (1999). KSHV infects endothelial cells and is found in spindle cells, and prior KSHV infection clearly predisposes for the onset of KS in AIDS patients. Boshoff, C. et al., *Nat Med* 1, 1274–8 (1995); Gao, S. J. et al., *N Engl J Med* 335, 233–41 (1996); Rezza, G. et al., *J Natl Cancer Inst* 91, 1468–74 (1999).

KSHV contains multiple open reading frames (ORF) encoding cellular homologs, including ORF 74, a GPCR most similar to CXCR2. Arvanitakis, L. et al., *Nature* 385, 347–50 (1997). Constitutive signaling by ORF 74 in NIH3T3 cells results in transformation of these cells, and transgenic mice expressing ORF 74 develop a disease with striking similarity to KS. Bais, C. et al., *Nature* 391, 86–89 (1998); Yang, T. Y. et al., *J Exp Med* 191, 445–54 (2000). The ligands for CXCR2, including IL-8, bind to ORF 74 with high affinity and activate signaling through this receptor. Gershengorn, H. C. et al., *J Clin Invest* 102, 1469–72 (1998). However, the biological ramifications of such signaling have not been clear.

While HIV-1 infection alone is not sufficient for the development of KS, AIDS-associated KS is more aggressive, disseminated, and resistant to treatment than the other forms of KS, including post-transplant KS. Buchbinder, A. et al., *Curr Opin Oncol* 4, 867–74 (1992); Friedman-Kien, A. E. et al., *Ann Intern Med* 96, 693–700 (1982); Strathdee, S. A. et al., *Aids* 10, S51–7 (1996). Therefore, immunosuppression alone cannot explain the frequent presentation of KS prior to immunosuppression, the greater prevalence of KS in AIDS patients than in other immunosuppressed individuals, and the association of KS with HIV-1, but not HIV-2, infection in West Africa. Ariyoshi, K. et al., *J Hum Virol* 1, 193–9 (1998); Beral, V. et al., *Lancet* 335, 123–8 (1990); Mocroft, A. et al., *Arch Intern Med* 158, 491–7 (1998); Poznansky, M. C. et al., *Bmj* 311, 156–8 (1995). Thus, there has been much interest in HIV-related factors which might potentiate the development of KS. The HIV-1 transactivator protein Tat has been clearly implicated in the growth of KS cells, and in combination with basic fibroblast growth factor (bFGF), is believed to drive the formation of lesions. Ensoli, B. et al., *Nature* 345, 84–6 (1990); Ensoli, B. et al., *Nature* 371, 674–80 (1994). Extracellular Tat acts in a paracrine fashion on KS cells by binding to integrin receptors. Barillari, G. et al., *Proc Natl Acad Sci USA* 90, 7941–5 (1993); Ensoli, B. et al., *J Virol* 67, 277–87 (1993). Thus, Tat is the HIV-1 protein with the strongest link to the pathogenesis of KS.

It would thus be desirable to provide a method of controlling viral replication in a host cell comprising inhibiting the biological action of chemokines in stimulating viral replication. Such methods could involve eliminating or sequestering the chemokines or alternately, blocking chemokine receptors so that the chemokines cannot bind.

It would be further desirable to provide methods for treating a patient with a viral infection. Preferably such methods will inhibit or suppress viral replication resulting in the prevention, delay or abatement of the symptoms associated with a viral infection.

SUMMARY OF THE INVENTION

Methods for suppressing or inhibiting viral replication in a virus infected host cell are provided. The methods comprise interfering with the binding of chemokines to chemokine receptors to suppress or inhibit viral replication. In a preferred embodiment viral (HIV) replication is suppressed or inhibited by interfering with the binding of C-X-C chemokines to C-X-C chemokine receptors. In a more preferred embodiment the C-X-C chemokines are IL-8, GRO-$\alpha$ or IP-10.

Also provided are methods of treating viral infections, comprising administering to a patient a therapeutically effective amount of a composition comprising at least one compound capable of preventing C-X-C chemokine stimulated viral replication. Such methods are particularly useful in treating patients that test seropositive for HIV and/or have Kaposi's Sarcoma.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 7A. Intracellular IL-8 is present in the monocytic subpopulation of PBMC exposed to HIV-1. PBMC were treated with monensin (Control) along with HIV-1$_{BaL}$, HIV-1$_{BRU}$, or TNF-$\alpha$ (100 ng/ml). PBMC were harvested after 6 hours and analyzed for intracellular IL-8 protein by flow cytometry. Lymphocyte and monocyte subpopulations were gated according to the pattern of forward scatter and side scatter;

FIG. 7B. Intracellular IL-8 is present in the monocytic subpopulation of PBMC exposed to HIV-1. PBMC were treated with monensin (Control) along with HIV-1$_{BaL}$, HIV-1$_{BRU}$, or TNF-$\alpha$ (100 ng/ml). Background staining in the lymphocyte and monocytes was determined by incubation with PE-mouse IgG$_1$ isotype control (Mouse IgG-PE) and FITC-mouse IgG$_{2a}$ isotype control (Mouse IgG-FITC). The histograms show fluorescence intensity on logarithmic scales along the x-axis (FITC) and y-axis (PE). The percentage of FITC+ cells is indicated for both the double positive and single positive gates;

FIG. 7C. Intracellular IL-8 is present in the monocytic subpopulation of PBMC exposed to HIV-1. PBMC were treated with monensin (Control) along with HIV-1$_{BaL}$, HIV-1$_{BRU}$, or TNF-$\alpha$ (100 ng/ml). Lymphocytes and monocytes were stained with a FITC-conjugated mouse anti-human IL-8 antibody (IL-8-FITC) and either a PE-conjugated mouse anti-human CD4 (CD4-PE) or CD14 (CD14-PE) respectively. The percentage of CD4+ or CD14+ cells staining positive for IL-8 in each condition is indicated. Data shown are representative of four independent experiments;

Figure 15A:
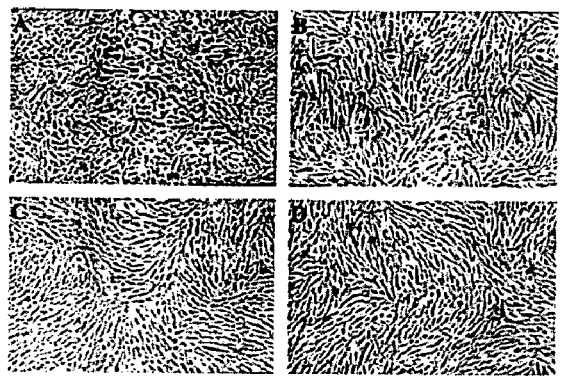
Figure 15B:
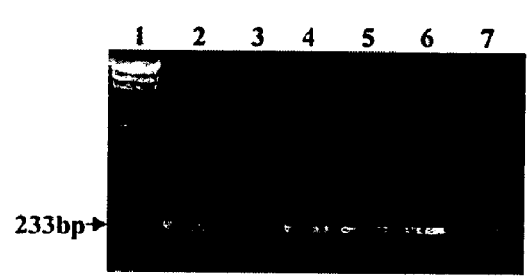
Figure 15C:
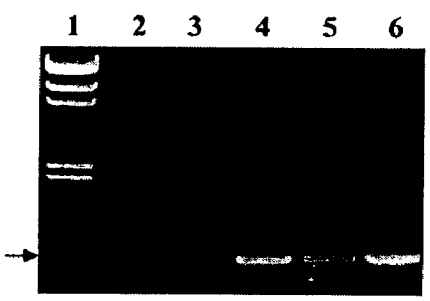
Figure 15D:
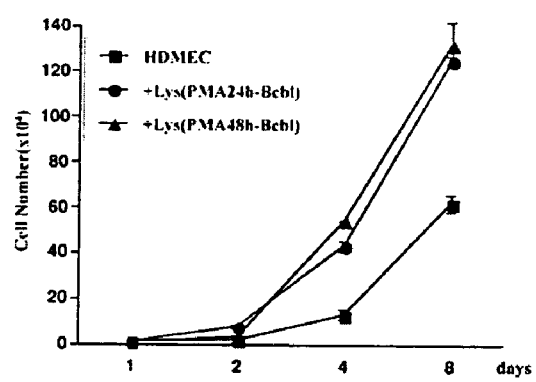
Figure 16:
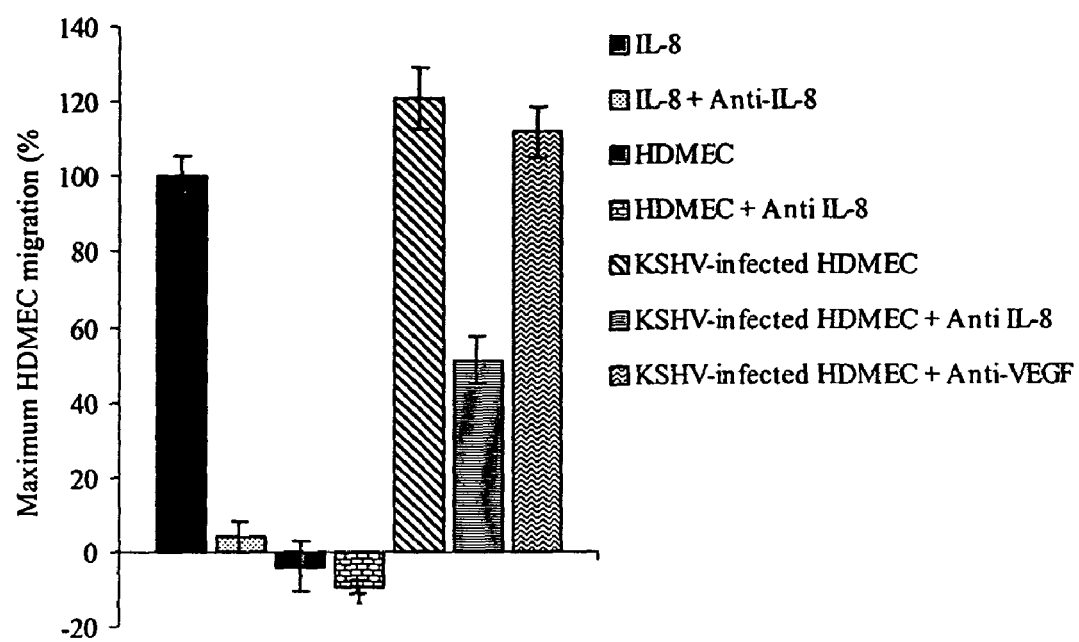
Figure 17A:
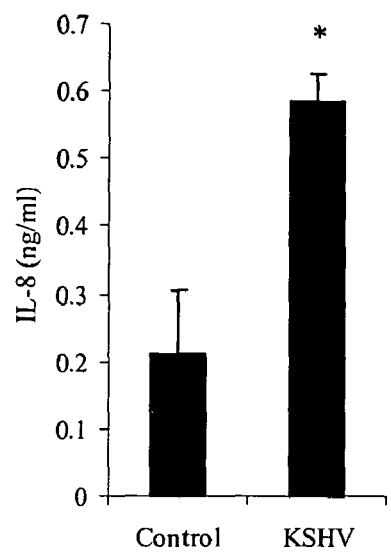
Figure 17B:
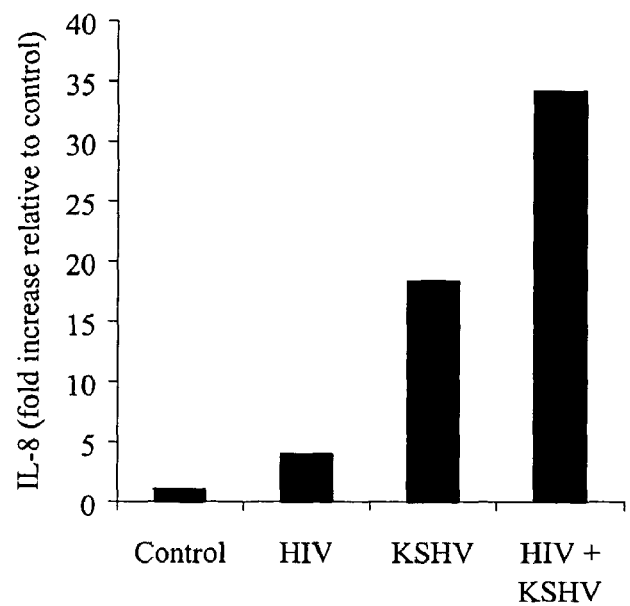

U937 cells were transfected with HIV-1 Tat or a control plasmid along with a plasmid containing the CAT gene downstream of either sequence with no known promoter (Control), the IL-8 promoter, or the HIV-1 LTR. The cells were either left untreated or treated with TNF-α (1 ng/ml) at 24 hours and harvested at 48 hours after transfection. CAT activity was quantified and normalized for the amount of protein. Values near 6000 represent complete acetylation of chloramphenicol (100%). This experiment is representative of three independent experiments;

FIG. 15A. Characterization of BCBL-1 cell lysate-treated HDMEC. Phase contrast microscopy of BCBL-1 cell lysate treated HDMEC (magnification: ×10). Untreated HDMEC were grown on gelatinized tissue culture flasks and demonstrate the typical endothelial cell morphology (a). After incubation with lysates of BCBL-1 cells (b), or BCBL-1 cells pre-treated with PMA for 24 hours (c) or 48 hours (d), the cells assume a spindle shape;

FIG. 15B. Polymerase Chain Reaction (PCR) detection of viral DNA sequence in BCBL-1 cell lysate-treated HDMEC and cell-free supernatants. Viral DNA was detected by PCR in HDMEC or their supernatants at passage 4 after BCBL-1 cell lysate treatment. Arrow denotes the specific 233 bp DNA fragment. The samples are in the following lanes: 1. DNA marker; 2. BCBL-1 cells (positive control); 3. untreated HDMEC; 4. HDMEC infected with BCBL-1 lysate; 5. HDMEC infected with 24 h PMA-treated BCBL-1 lysate; 6. HDMEC infected with 48 h PMA-treated BCBL-1 lysate; 7. Supernant of HDMEC+BCBL-1 lysate;

FIG. 15C. PCR analysis demonstrating KSHV cyclin D gene amplified in infected HDMEC at passage 12. The samples are in the following lanes: 1. DNA/HindIII marker; 2. Normal HDMEC; 3. HDMEC infected with BCBL-1 lysate; 4. HDMEC infected with 24 h PMA-treated BCBL-1 lysate; 5. HDMEC infected with 48 h PMA-treated BCBL-1 lysate; 6. BCBL-1 cells (positive control);

FIG. 15D. KSHV infection of HDMEC stimulates cellular proliferation. HDMEC (~$10^4$) were plated in triplicate in 60-mm tissue culture plates and fed every other day. The total number of parental HDMEC cells (■), or HDMEC infected with 24 or 48 h PMA-treated BCBL-1 lysates (●, ▲) was counted on each indicated day;

FIG. 16 is a bar graph showing that IL-8 is a major component of the angiogenic activity present in the conditioned media of KHSV-infected HDMEC. Conditioned media derived from uninfected or KSHV-infected HDMEC, with or without neutralizing antibodies to IL-8 or VEGF, were assayed for their ability to stimulate the chemotaxis of endothelial cells. Specific migration was determined by subtracting background migration (unstimulated control). Values are reported as a percentage (±SEM) of migration induced by recombinant IL-8;

FIG. 17A. KSHV infection of human dermal microvascular endothelial cells (HDMEC) induces the release of IL-8. HDMEC (80–95% confluent) were infected with KSHV from PMA-stimulated BCBL-1. Results are the mean of four experiments (±S.D.);

FIG. 17B. HIV-1 and KSHV act synergistically on IL-8 production. Adherent MDM were detached by EDTA treatment and then co-cultured with KSHV just prior to treatment with no virus (Control), HIV-1$_{BRU}$, KSHV, or both viruses. Conditioned media were collected after 24 hours for analysis of IL-8 by ELISA.

Figure 18A:
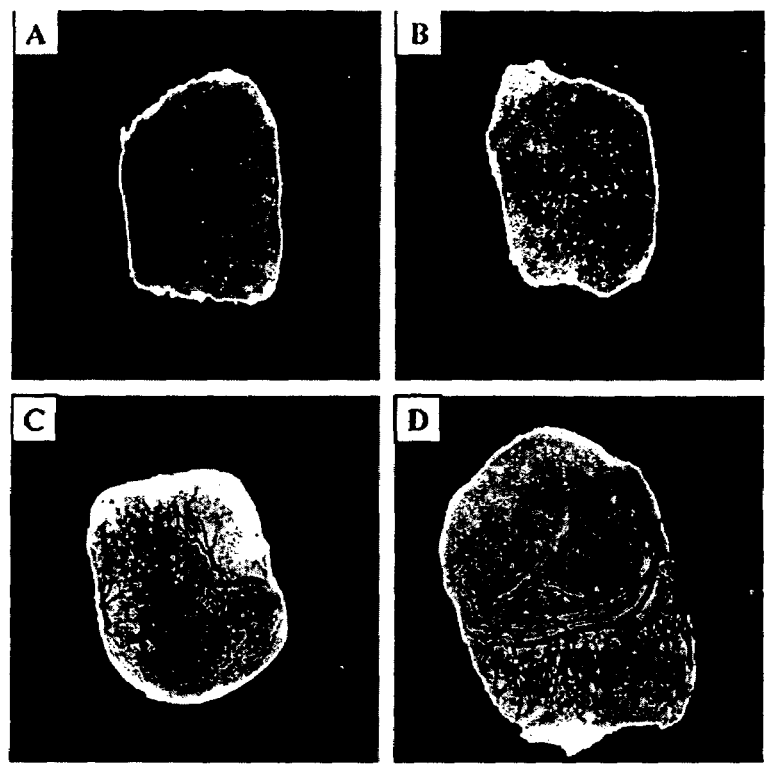
Figure 18B:
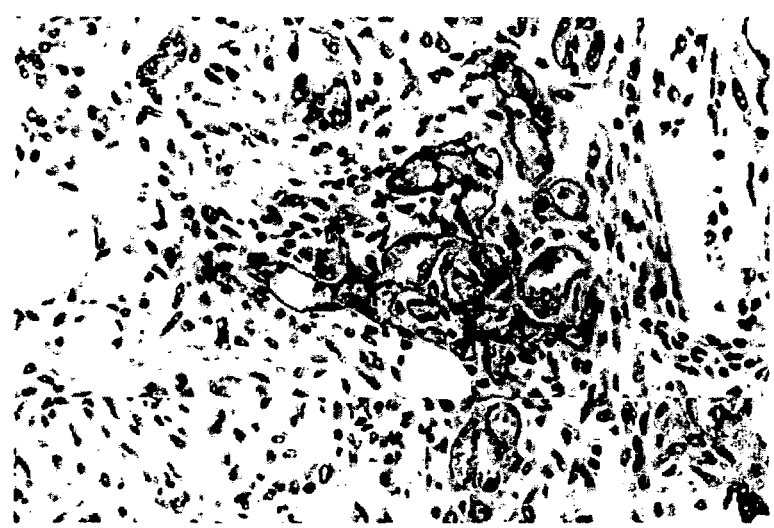
Figure 18C:
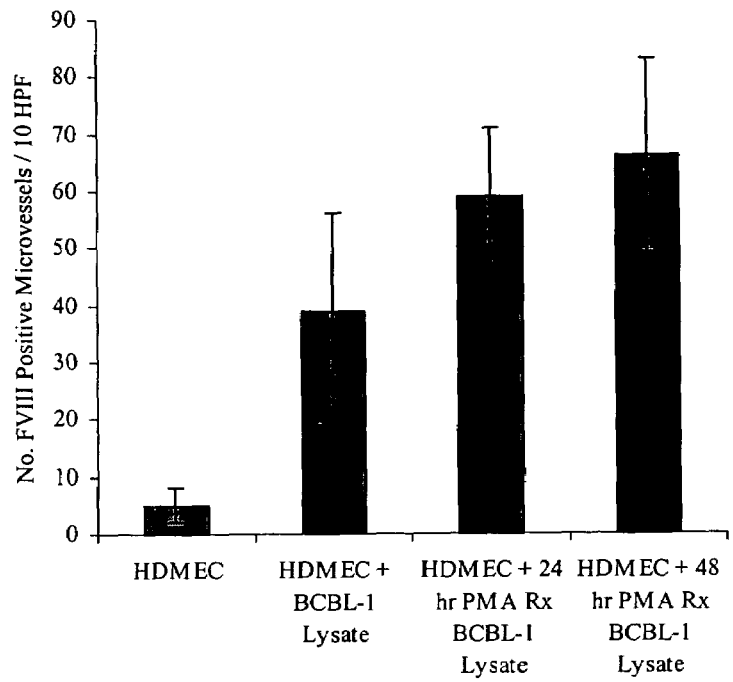
Figure 18D:
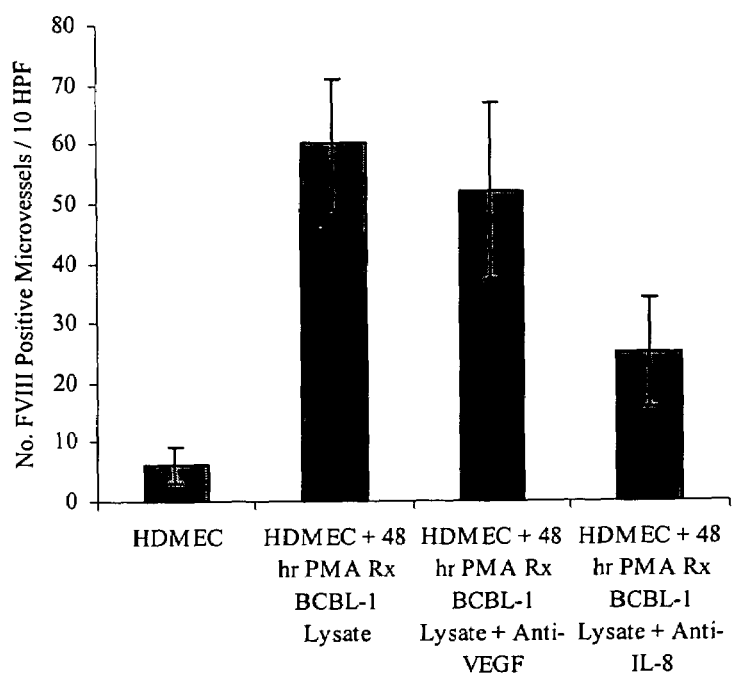
Figure 19A:
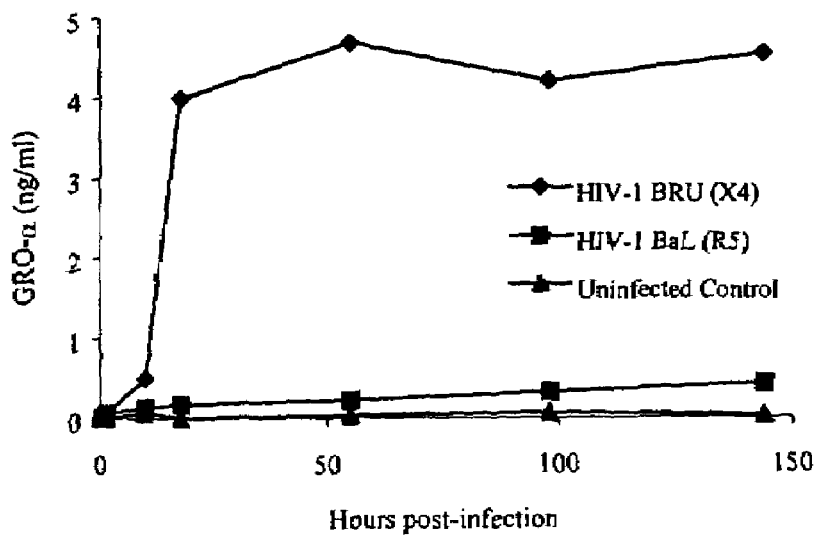
Figure 19B:
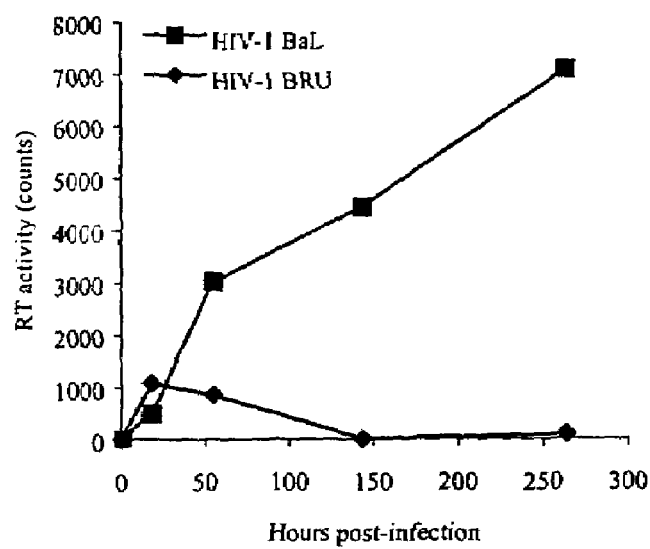
Figure 19C:
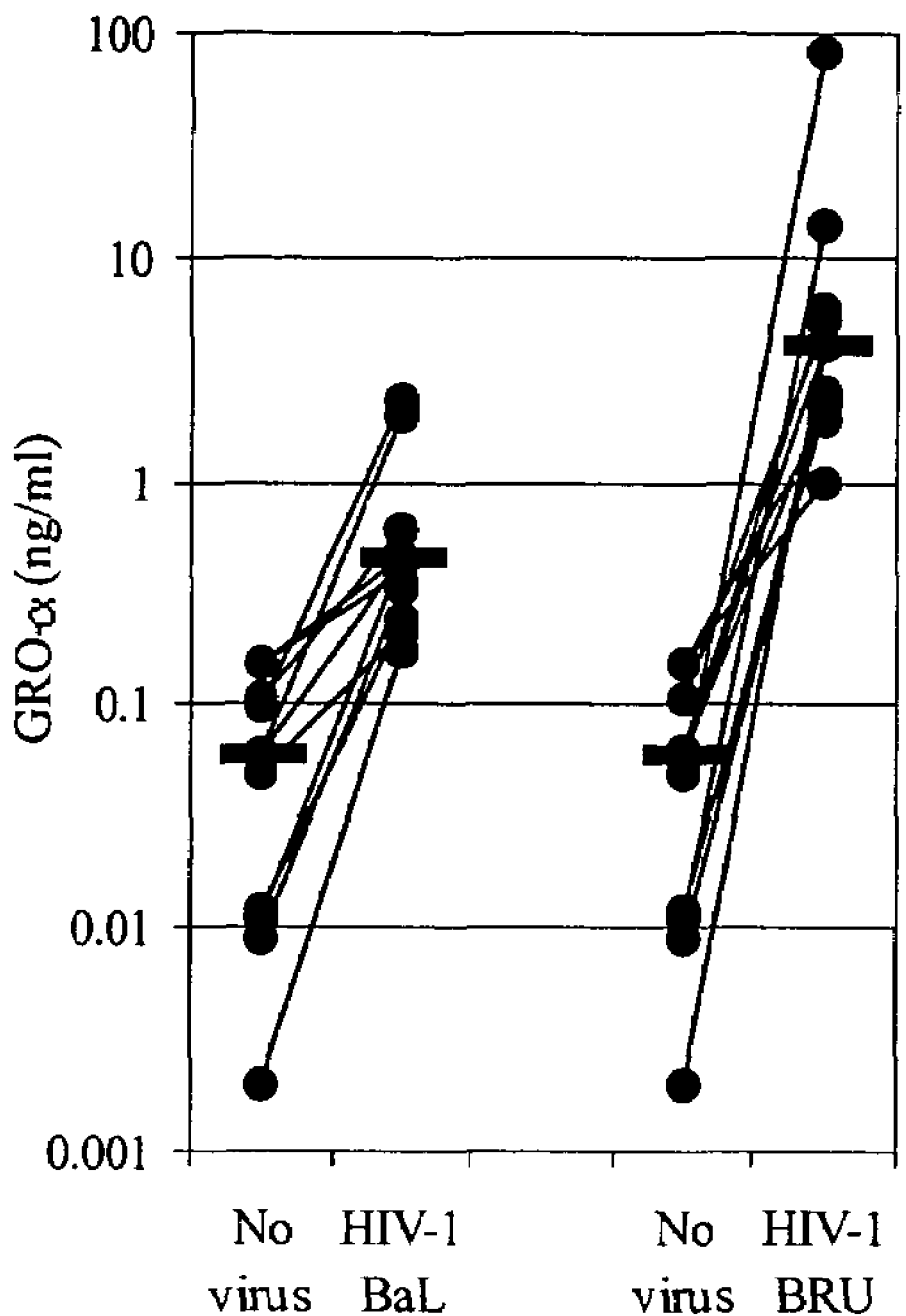
Figure 20:
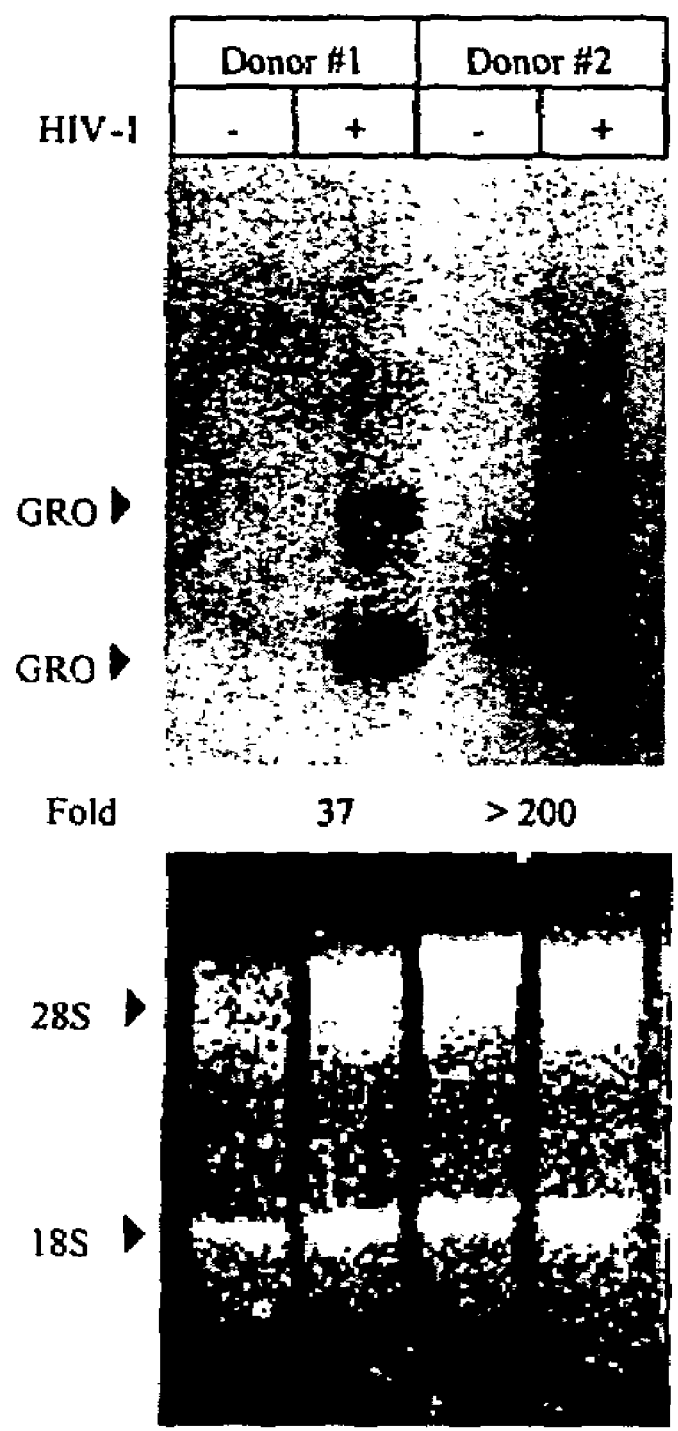
Figure 21A:
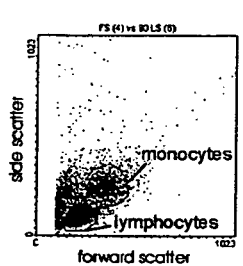
Figure 21B:
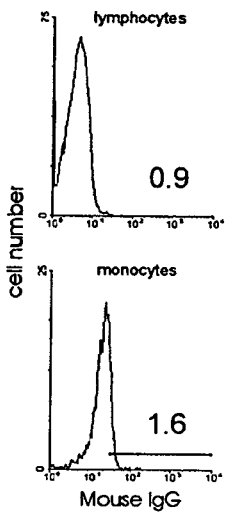
Figure 21C:
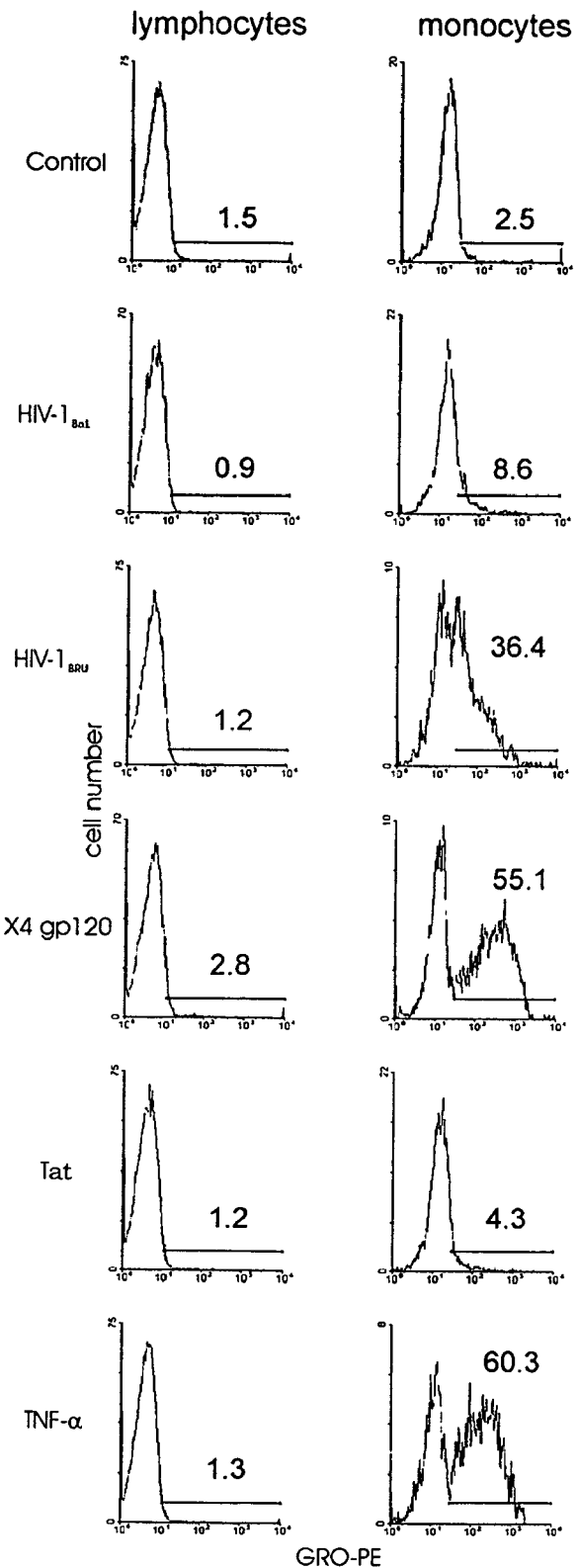
Figure 22A:
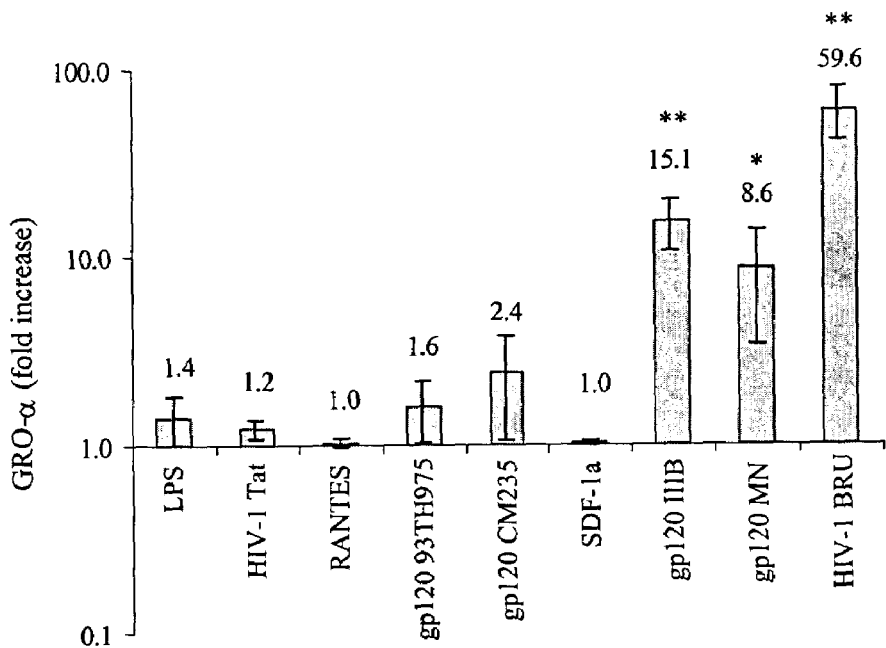
Figure 22B:
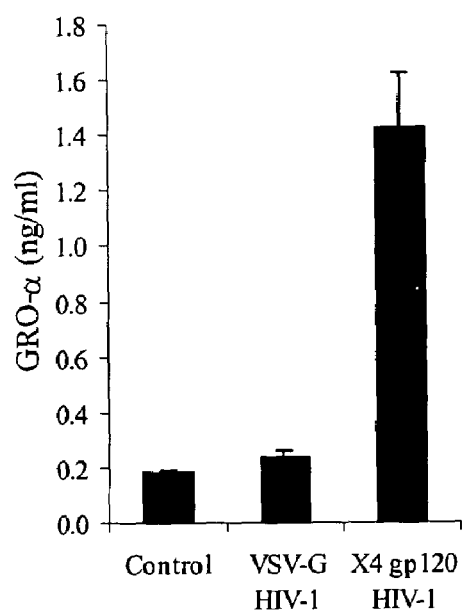
Figure 23:
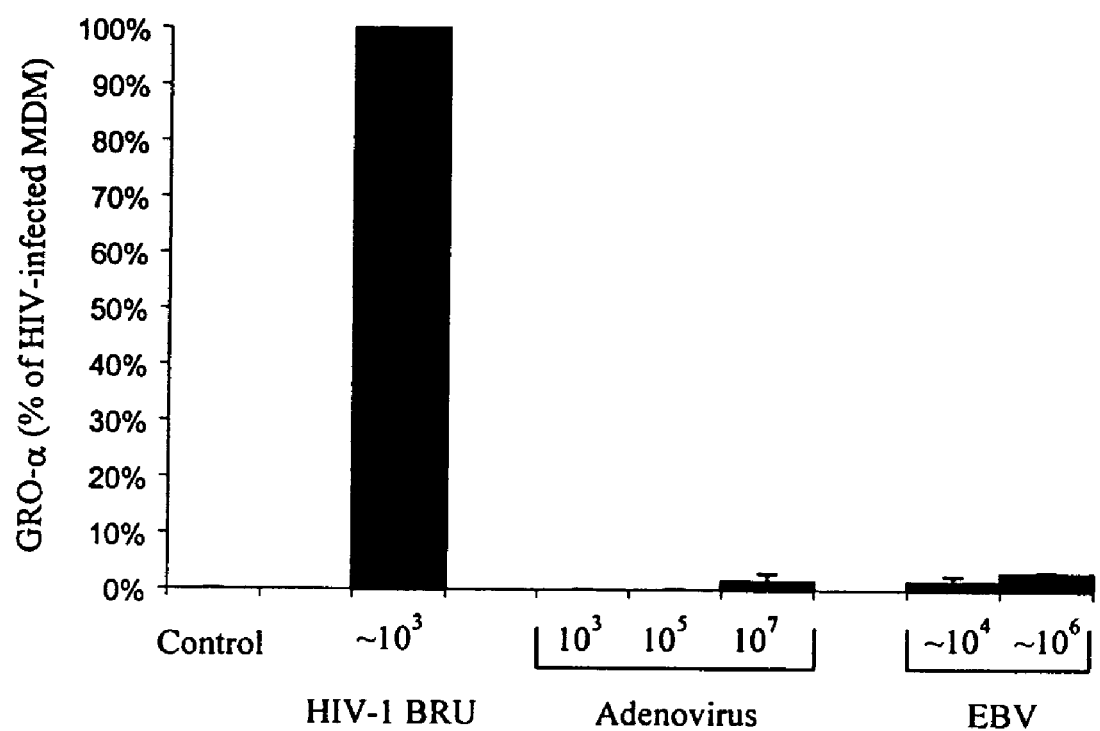
Figure 24A:
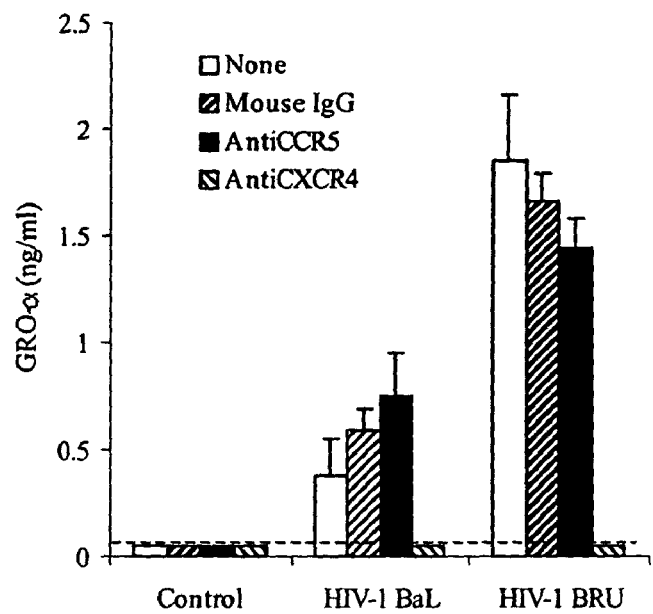
Figure 24B:
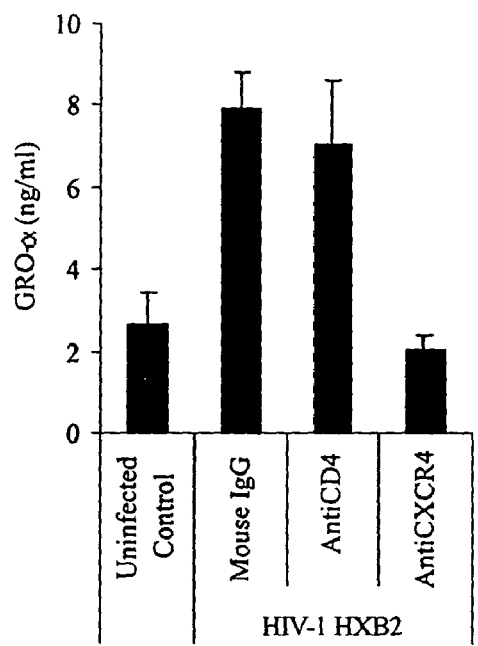

FIG. 18A. KSHV-infected HDMEC stimulate angiogenesis in SCID mice. HDMEC or KSHV-infected HDMEC ($1\times10^6$) were seeded in a PLA sponge and implanted into the flank of SCID mice in duplicate. After 14 days, implanted sponges were removed from mice and photographs were taken using a Nikon anatomy scope (magnification: 1.5–2×). The sponges photographed in each panel are HDMEC (A), HDMEC infected with BCBL-1 lysate (B), HDMEC infected with 24 h PMA-treated BCBL-1 lysate (C), and HDMEC infected with 48 h PMA-treated BCBL-1 lysate (D);

FIG. 18B. Immunostaining of transplanted KSHV-infected tissue reveals new vessel formation. KSHV-infected HDMEC ($1\times10^6$) were seeded in a PLA sponge and implanted into the flank of SCID mice in duplicate. After 14 days the sponges were retrieved and stained with a rat anti-mouse CD31 antibody at high power (400×) to visualize new vessel formation;

FIG. 18C. The number of CD31 positive blood vessels were counted in 10 random fields from 3 independent sponges for each condition;

FIG. 18D. IL-8 is a major inducer of angiogenesis in KSHV-infected HDMEC. HDMEC or 48 h PMA-treated BCBL-1 lysate-treated HDMEC ($1\times10^6$) were seeded in a PLA sponge with or without neutralizing antibodies to IL-8 or VEGF and implanted into the back of SCID mice in duplicate. The number of CD31 positive blood vessels were counted in 10 random fields from three independent PLA sponges for each condition;

FIG. 19A. Increased production of GRO-α by MDM following encounter with HIV-1 is independent of productive infection. MDM were infected with equal counts of reverse transcriptase (RT) activity of HIV-1$_{BaL}$ or HIV-1$_{BRU}$. Extracellular immunoreactive GRO-α was measured by ELISA;

FIG. 19B. HIV replication was determined by quantitating the RT activity (above the background activity in uninfected controls) present in the supernatants. A portion of the supernatant was collected at several timepoints as indicated, so that input virus was removed entirely from the cells by day 2, at which point fresh media was added, and a portion of the media (25%) was removed and replaced twice weekly. These experiments are representative of experiments performed with MDM from three different donors;

FIG. 19C. Exposure to X4 HIV (HIV-1$_{BRU}$) stimulates GRO-α production by MDM to a greater extent than exposure to R5 HIV (HIV-1$_{BAL}$). Shown are the results of ELISA for GRO-α performed on the supernatants collected one day after exposure of MDM from 11 different donors to HIV-1. Lines connect the values for control (No virus) and HIV-exposed MDM from each donor on this logarithmic scale. The horizontal black bars indicate the median values;

FIG. 20. HIV-1 increases GRO mRNA levels in MDM. Total cellular RNA was extracted from control MDM (−) and MDM exposed to HIV-1$_{BRU}$ (+) after 2 days. RNA from two different donors was then analyzed for GRO gene expression by northern (RNA) blot analysis using a GRO-specific probe (top panel). The total amount of RNA was determined by quantitating the intensity of the 28S and 18S rRNA bands (bottom panel). The amount of GRO mRNA was normalized to the amount of rRNA in each sample and the fold increase in HIV-exposed MDM relative to control MDM is indicated;

FIG. 21A. Intracellular GRO protein is present in monocytes exposed to HIV-1 and gp120. PBMC were treated with GolgiStop (Control) along with HIV-1$_{BaL}$, HIV-1$_{BRU}$, X4 gp120 (1 µg/ml, from HIV-1$_{IIIB}$), Tat (100 ng/ml), or TNF-α (100 ng/ml). PBMC were harvested after 6 hours and analyzed for intracellular GRO proteins by flow cytometry. Lymphocyte and monocyte subpopulations were gated according to the pattern of forward scatter and side scatter;

FIG. 21B. Background staining in lymphocytes and monocytes was determined by incubation with PE-mouse IgG, isotype control (Mouse IgG). The histograms show fluorescence intensity on a logarithmic scale along the x-axis and the number of events on the y-axis. The percentage of cells staining positive in each condition is indicated;

FIG. 21C. Staining of lymphocytes and monocytes with a PE-conjugated mouse anti-human GRO antibody (GRO-PE) for each treatment condition is shown. Data shown are representative of four independent experiments;

FIG. 22A. HIV-1 gp120 stimulates GRO-α production. MDM were exposed to HIV-1$_{BRU}$ or treated with recombinant gp120 (1 µg/ml) from isolates HIV-1$_{93TH975}$ (R5), HIV-1$_{CM235}$ (R5), HIV-1$_{IIIB}$ (X4), HIV-1$_{MN}$ (X4), or HIV-1 Tat (1 µg/ml), SDF-1α (0.5 µg/ml), RANTES (1.35 µg/ml), or LPS (1 µg/ml) as indicated. Supernatants were collected after 1 day and analyzed by ELISA for GRO-α. Data are shown on a logarithmic scale and are the mean (±SEM) of the results of 3 to 13 independent experiments for each treatment. Data and data labels are fold increase relative to untreated controls;

FIG. 22B. Pseudotyped, replication-incompetent HIV-1 was prepared by co-transfection of 293 cells with an env(−) HXB2-based HIV-1 provirus and either the vesicular stomatitis virus glycoprotein (VSV-G) or gp120 from HIV-1$_{HXB2}$ (X4 gp120). MDM were treated with 50% cell-free supernatants from transfected or mock-transfected 293 cells. ELISA was performed on supernatants collected 2 days after treatment. Data shown are representative of three experiments;

FIG. 23. MDM produce GRO-α in response to HIV-1, but not adenovirus or Epstein-Barr virus (EBV), type 1. The approximate number of viral particles added to $10^5$ MDM is indicated. Data are the mean values of multiple wells of MDM from two donors;

FIG. 24A. GRO-α production is mediated by interaction of HIV-1 with CXCR4. MDM were pre-incubated with antibodies (20 µg/ml) to CCR5 (2D7) or CXCR4 (12G5), each of which is known to neutralize HIV infection, or mouse IgG (20 µg/ml) or no antibody as controls, and then exposed to either HIV-1$_{BaL}$ or HIV-1$_{BRU}$. Supernatants were collected after 24 hours and analyzed by ELISA. Several values fell below the limit of detection (dashed line);

FIG. 24B. MDM were pre-incubated with (20 µg/ml) antibodies to CCR5 (2D7) or CXCR4 (12G5) or with anti-CD4 (15 µg/ml) before exposure to the X4 isolate HIV-1$_{HXB2}$. Data shown are representative of five independent experiments.

Figure 25:
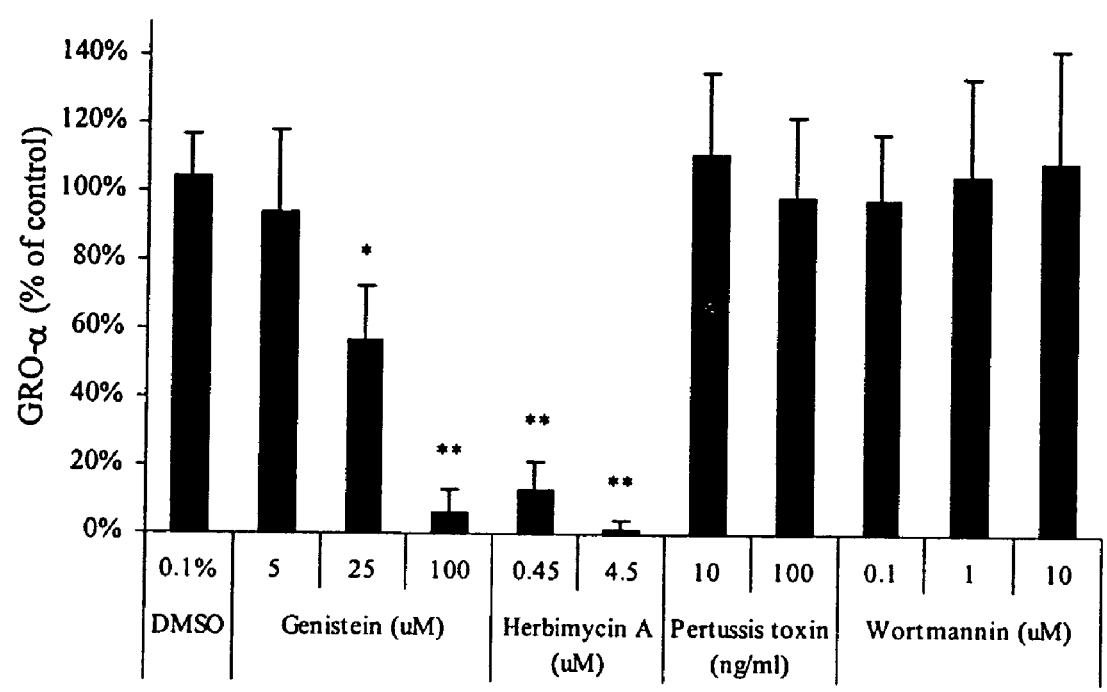
Figure 26A:
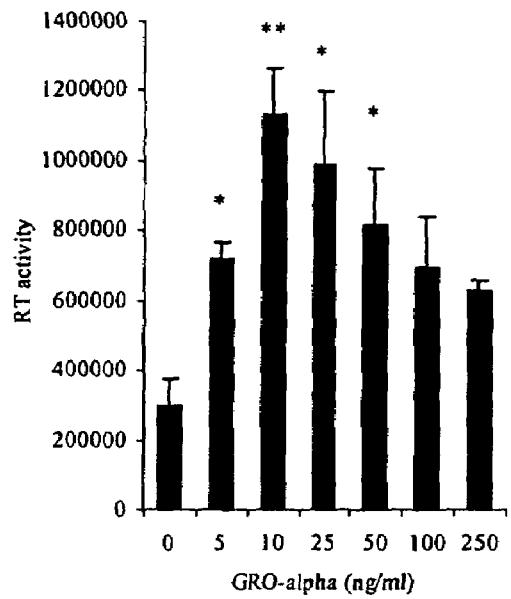
Figure 26B:
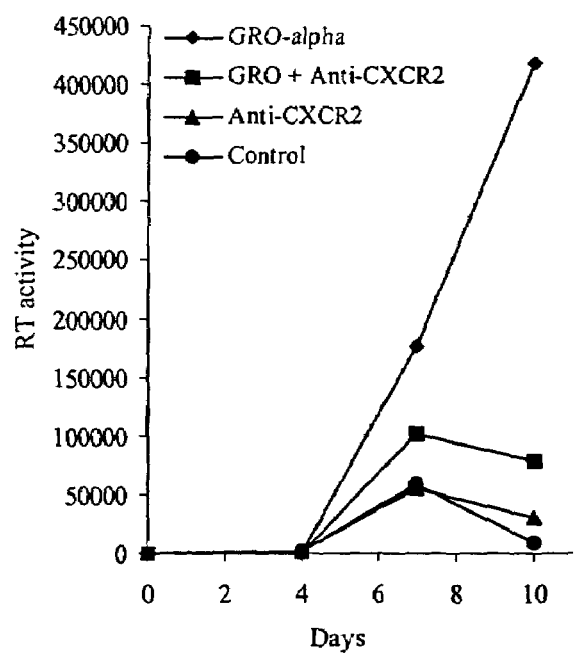
Figure 26C:
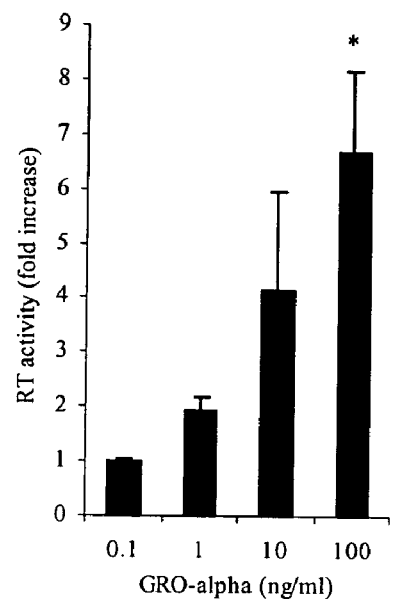
Figure 26D:
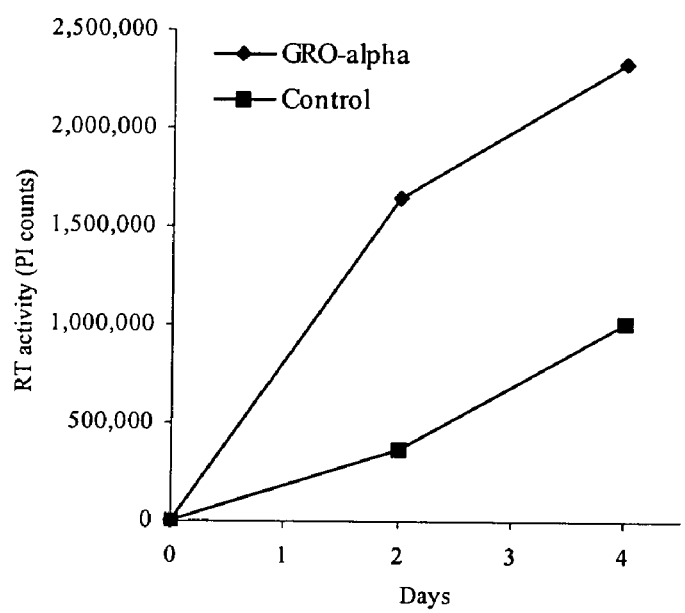
Figure 27:
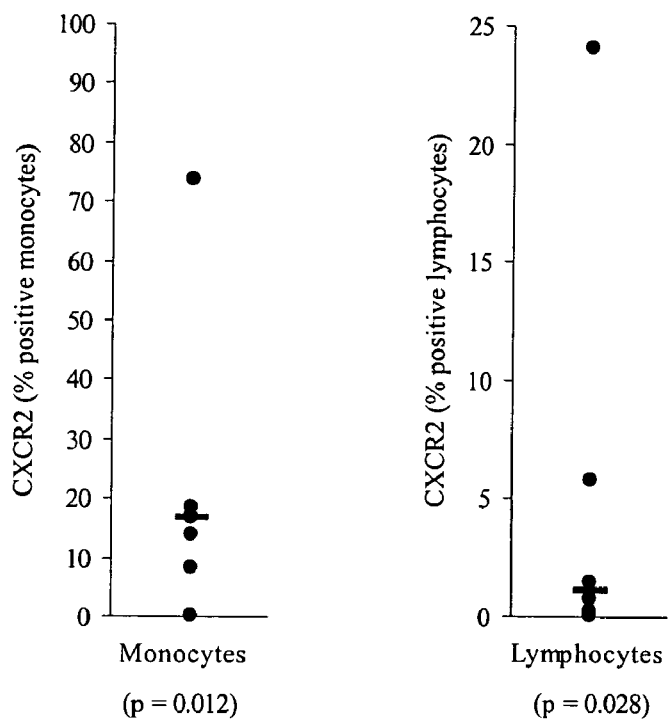
Figure 28:
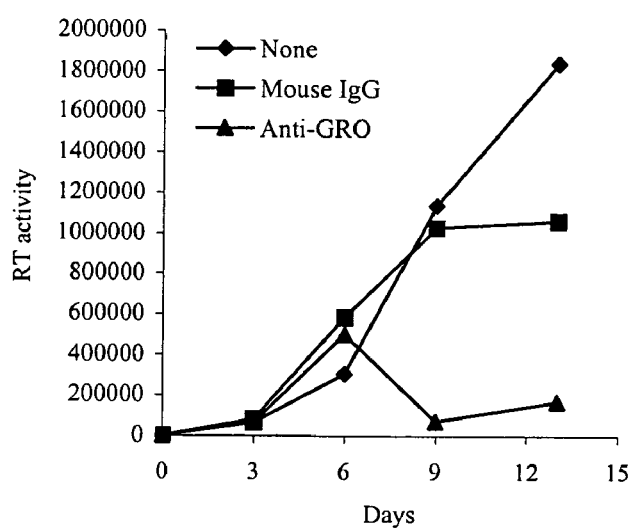
Figure 29A:
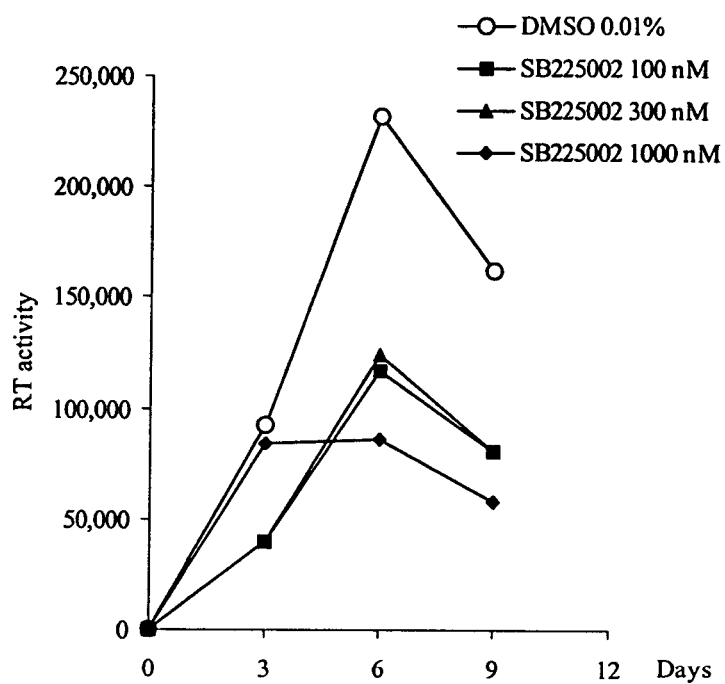
Figure 29B:
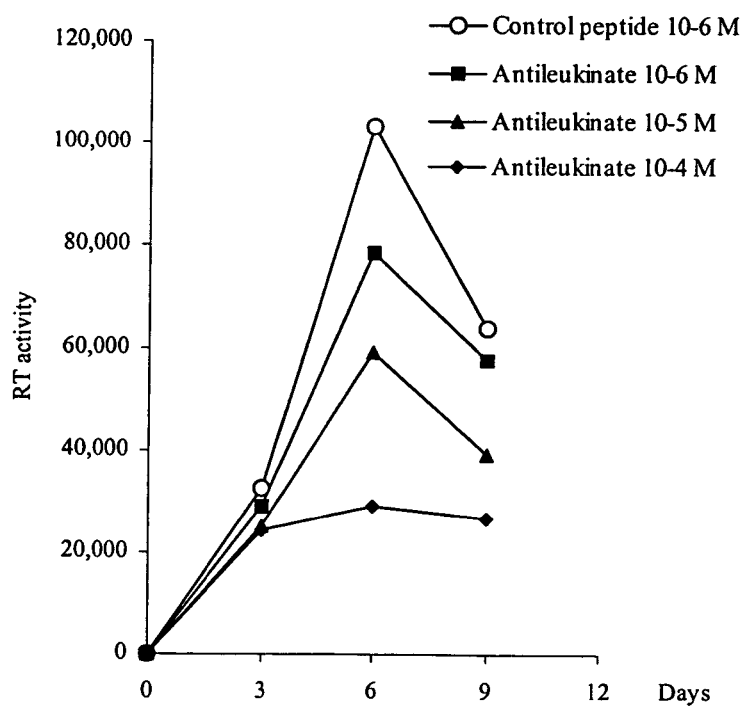

FIG. 25. HIV-1$_{BRU}$-induced GRO-α production by MDM is sensitive to the PTK inhibitors genistein and herbimycin A, and not to pertussis toxin or the PI3K inhibitor wortmannin. Supernatants were collected 20 hours after exposure to virus and analyzed for GRO-α production by ELISA. Data shown are the mean of the results of three independent experiments performed in triplicate and are representative of at least three experiments for each inhibitor. DMSO (0.1%) was used as a negative treatment control. The inhibitor treatments shown did not negatively affect cellular viability and activation as determined by MTT assay (Boehringer Mannheim, Mannheim, Germany). Reductions in GRO-α production by concentrations of inhibitors that reduced viability by >25% were attributed to toxicity and not included;

FIG. 26A. GRO-α stimulates HIV-1 replication in MDM and PBL. MDM were treated with GRO-α at the indicated concentrations for 16 hours before infection with HIV-$1_{BaL}$. Supernatants were analyzed for RT activity 8 days after infection;

FIG. 26B. MDM were treated twice weekly with GRO-α (25 ng/ml) and/or anti-CXCR2 (20 μg/ml) starting one day before infection with HIV-$1_{BaL}$;

FIG. 26C. CD8-depleted PBL were treated with GRO-α at the doses indicated one day before and two days after infection with HIV-$1_{BaL}$. RT activity was assayed on day 5;

FIG. 26D. PBL were treated with GRO-α (25 ng/ml) one day before and one and four days after infection with HIV-$1_{BRU}$. These experiments are representative of infections of cells from five (A), three (B), six (C), and seven (D) different donors;

FIG. 27. CXCR2 is expressed on monocytes and lymphocytes. PBMC were analyzed for CXCR2 expression by flow cytometry after 2 days. Monocytes (left panel) and lymphocytes (right panel) were gated according to forward and side scatter, and in some experiments, by the presence of CD4 or CD14. Data are presented as the percentage of cells staining positive with the anti-CXCR2 antibody minus the percentage of cells staining positive with the mouse $IgG_{2a}$ isotype control. Each point represents the value for a different donor (monocytes, n=8; lymphocytes, n=6). The horizontal black bars indicate the median values, which are 17.0% and 1.2% respectively. Data were found to be statistically significant using the Wilcoxon signed ranks test; p values are indicated below the data labels;

FIG. 28. Neutralization of endogenous, HIV-induced GRO reduces HIV-$1_{BaL}$ replication in MDM. MDM were treated with no antibody (None), mouse $IgG_1$, or anti-GRO (20 μg/ml) every three days starting one day before infection with HIV-$1_{BaL}$. Media was collected and replenished every 3 days. This experiment is representative of infections of cells from four different donors;

FIG. 29A. Inhibition of HIV-1 replication by CXCR2 inhibitors. The small molecular weight inhibitor SB225002 decreases HIV-1 replication in T lymphocytes. PHA-activated PBL were left untreated or treated with the indicated doses of SB225002 every three days beginning one day before infection with HIV-$1_{BRU}$, and HIV-1 replication was assayed by measuring the amount of RT activity in the supernatants on days 3, 6, and 9 after infection. This experiment is representative of three performed with PBL from different donors;

FIG. 29B. Inhibition of HIV-1 replication by CXCR2 inhibitors. The small molecular weight inhibitor SB225002 decreases HIV-1 replication in T lymphocytes. PHA-activated PBL were left untreated or treated with the indicated doses of SB225002 every three days beginning one day before infection with HIV-$1_{BRU}$, and HIV-1 replication was assayed by measuring the amount of RT activity in the supernatants on days 3, 6, and 9 after infection. This experiment is representative of three performed with PBL from different donors.

Figure 30A:
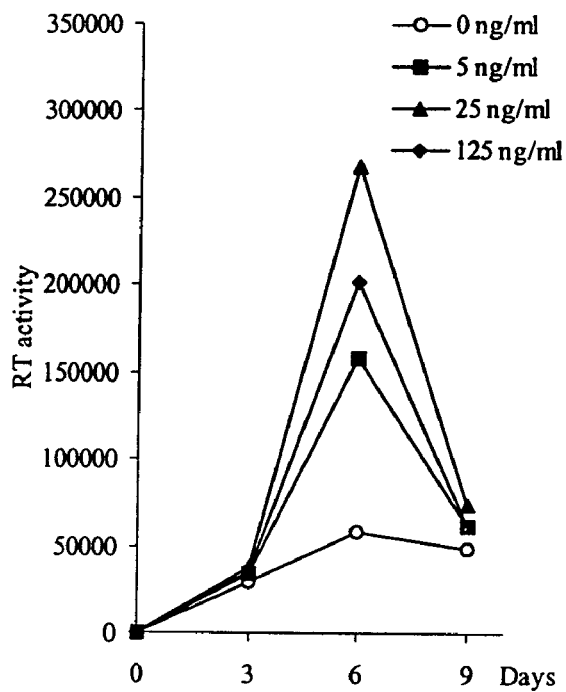

FIG. 30A is a graph showing the stimulation of HIV-$1_{BRU}$ replication in peripheral blood lymphocytes by the CXCR3 ligand 1P-10.

Figure 30B:
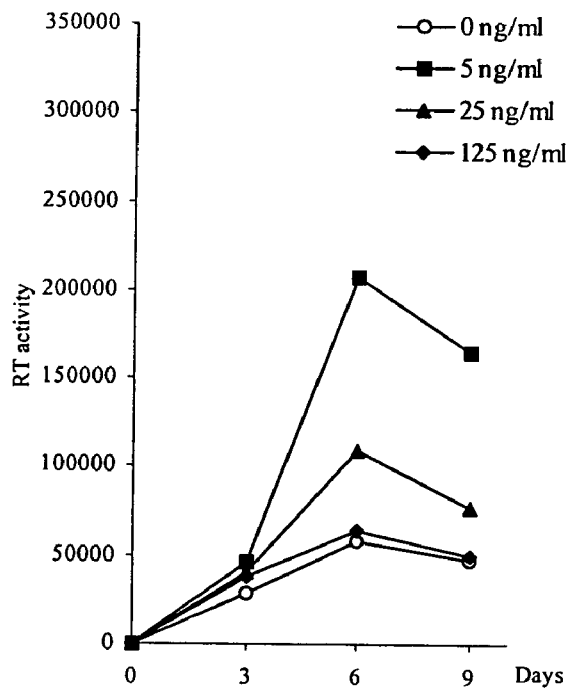
Figure 30C:
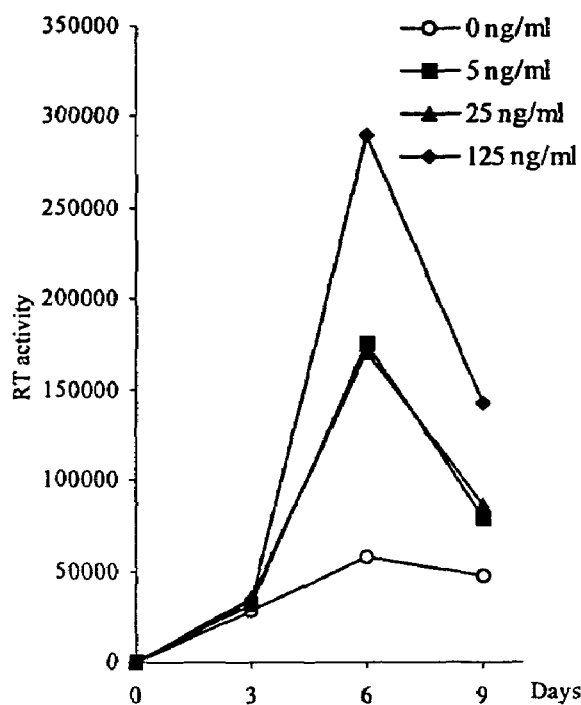
Figure 30D:
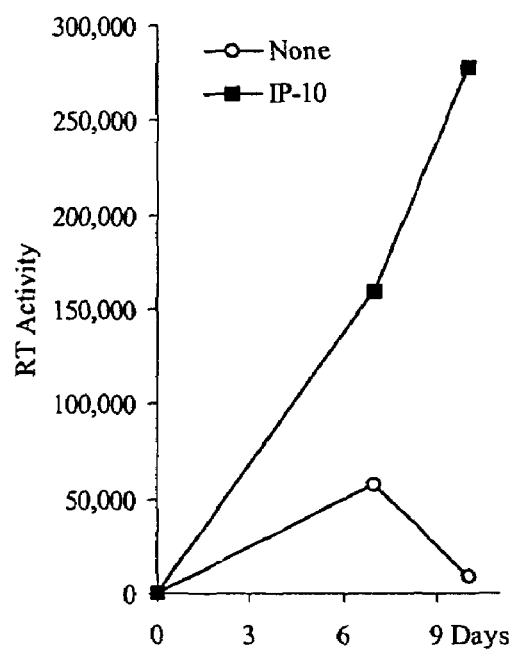
Figure 31A:
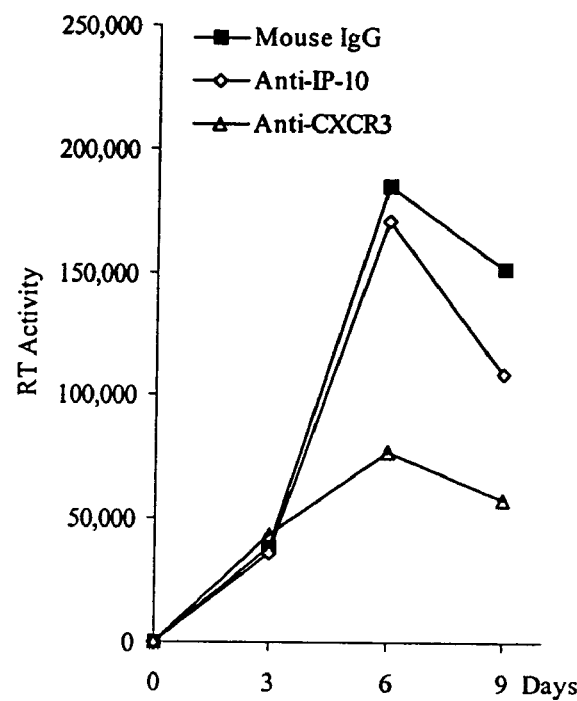

FIG. 30B is a graph showing the stimulation of HIV-$1_{BRU}$ replication in peripheral blood lymphocytes by the CXCR3 ligand MIG;

FIG. 30C is a graph showing the stimulation of HIV-$1_{BRU}$ replication in peripheral blood lymphocytes by the CXCR3 ligand I-TAC;

FIG. 30D is a graph showing the stimulation of HIV-$1_{BaL}$ replication in MDM by the CXCR3 ligand IP-10;

FIG. 31A. Depletion of endogenous IP-10 or blocking CXCR3 inhibits HIV-1 replication in PBL and MDM. PBL were treated with either mouse IgG, an antibody that prevents interaction with CXCR3, or an antibody that neutralizes IP-10 activity (each at 20 μg/ml) and infected with HIV-$1_{BRU}$. Media was collected for the RT assay and replenished every 2–3 days. Supernatants were analyzed for RT activity on the number of days after infection as indicated. The experiments shown are representative of at least three independent experiments.

Figure 31B:
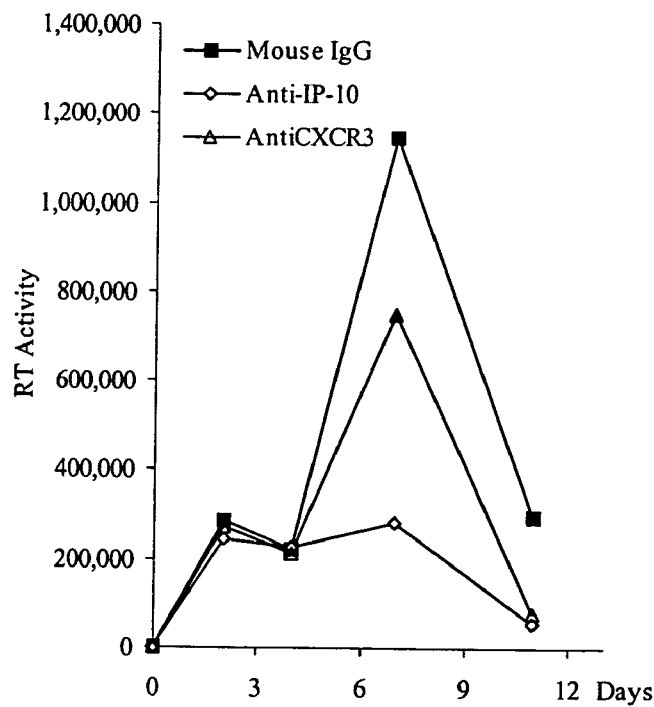

FIG. 31B. Depletion of endogenous IP-10 or blocking CXCR3 inhibits HIV-1 replication in PBL and MDM. PBL were treated with either mouse IgG, an antibody that prevents interaction with CXCR3, or an antibody that neutralizes IP-10 activity (each at 20 μg/ml) and infected with HIV-$1_{BRU}$. Media was collected for the RT assay and replenished every 2–3 days. Supernatants were analyzed for RT activity on the number of days after infection as indicated. The experiments shown are representative of at least three independent experiments.

Figure 31C:
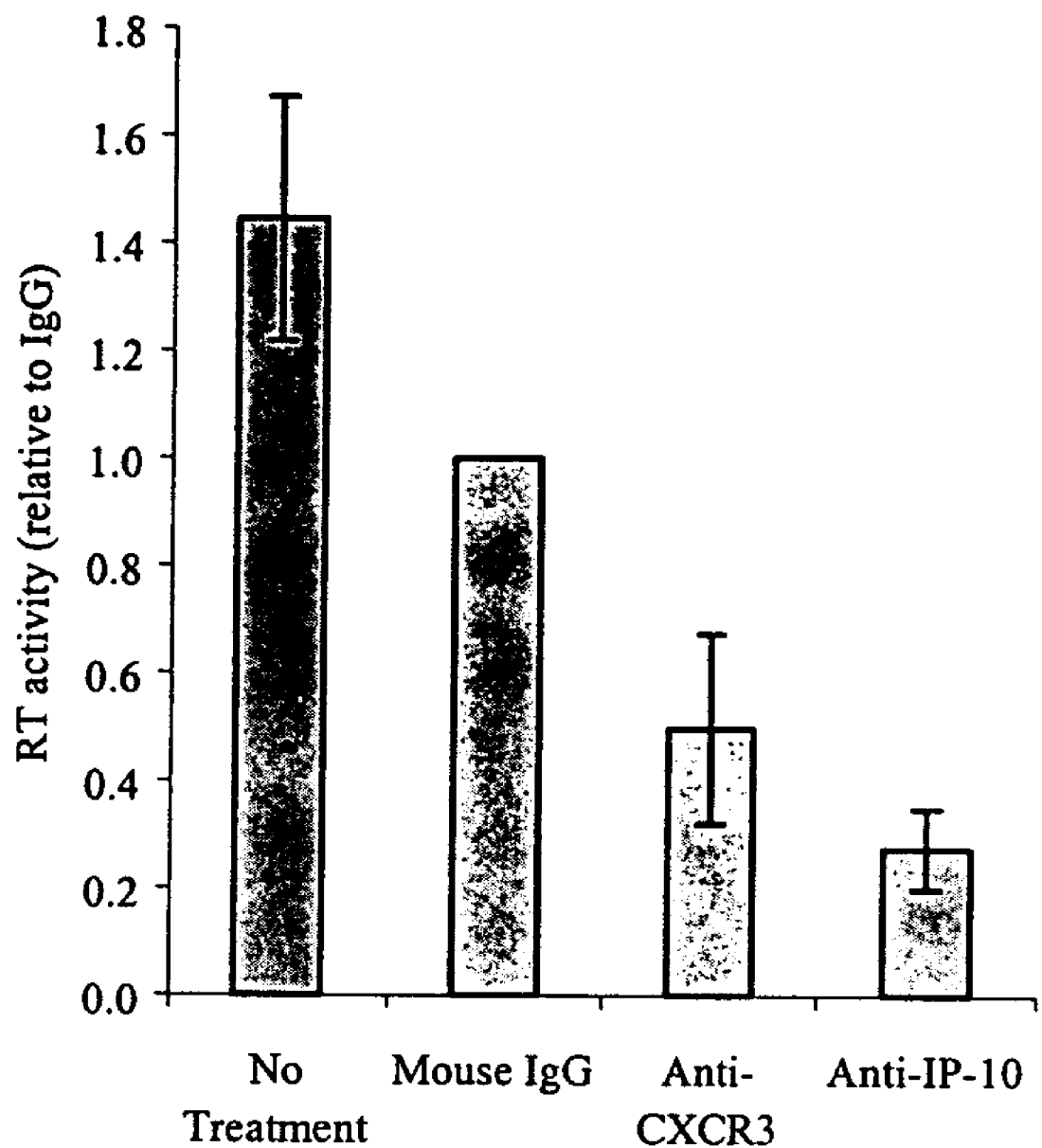
Figure 32:
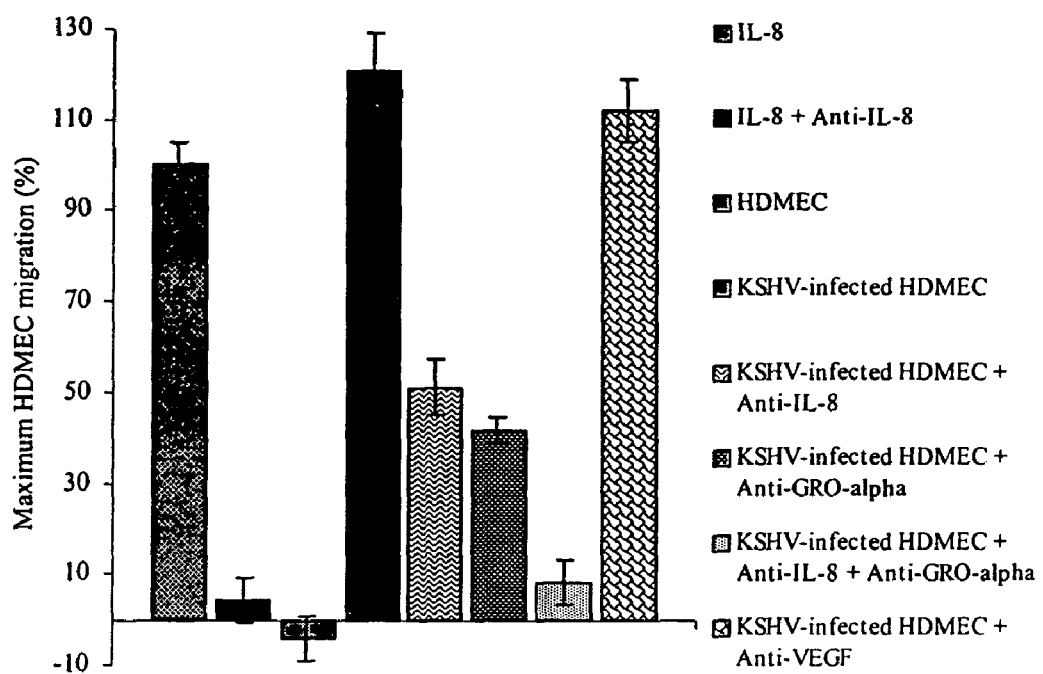
Figure 33:
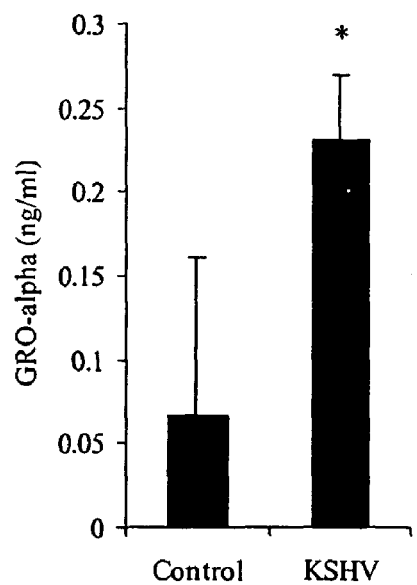
Figure 34A:
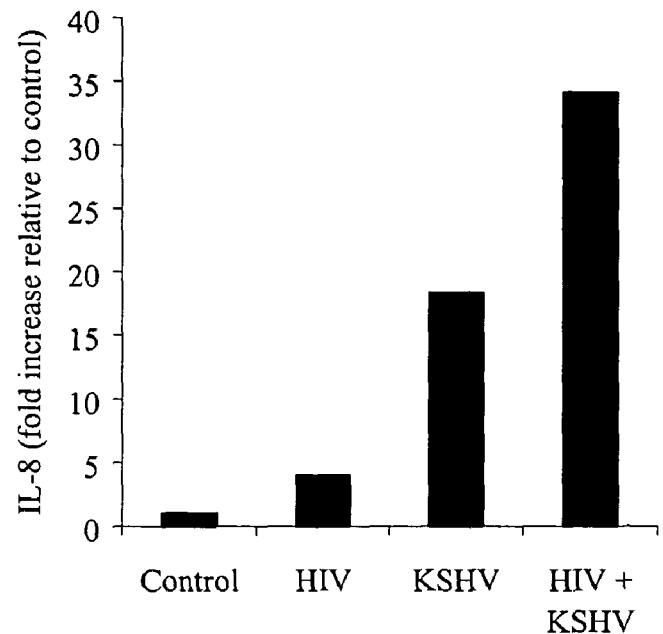
Figure 34B:
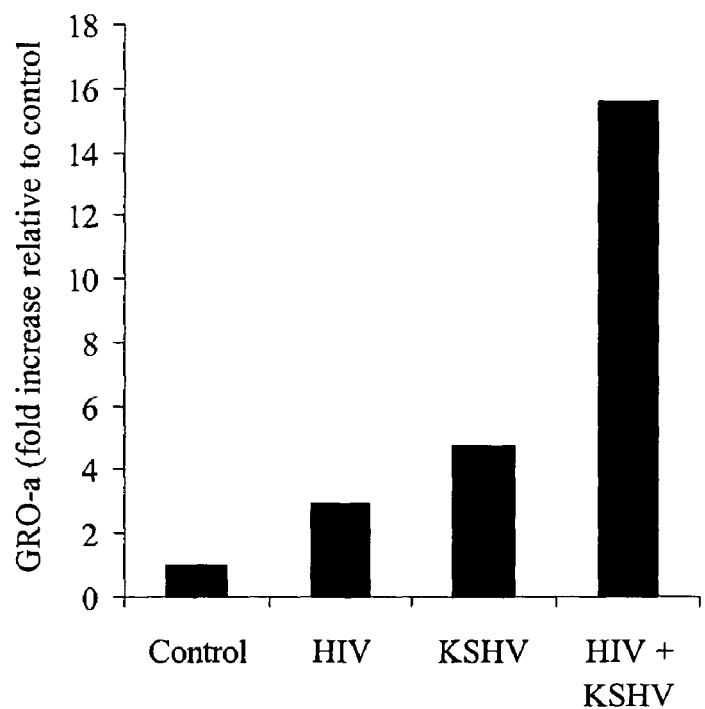

FIG. 31C. Depletion of endogenous IP-10 or blocking CXCR3 inhibits HIV-1 replication in PBL and MDM. PBL were treated with either mouse IgG, an antibody that prevents interaction with CXCR3, or an antibody that neutralizes IP-10 activity (each at 20 μg/ml) and infected with HIV-$1_{IIIB}$. Media was collected for the RT assay and replenished every 2–3 days. Supernatants were analyzed for RT activity on the number of days after infection as indicated. The experiments shown are representative of at least three independent experiments;

FIG. 32. IL-8 and GRO-α are major components of the angiogenic activity present in the conditioned media of KHSV-infected HDMEC. Conditioned media derived from uninfected or KSHV-infected HDMEC, with or without neutralizing antibodies to IL-8, GRO-α, or VEGF, were assayed for their ability to stimulate the chemotaxis of endothelial cells. Specific migration was determined by subtracting background migration (unstimulated control). Values are reported as a percentage (±SEM) of migration induced by recombinant IL-8;

FIG. 33. KSHV infection of human dermal microvascular endothelial cells (HDMEC) induces the release of GRO-α. HDMEC (80–95% confluent) were infected with KSHV from PMA-stimulated BCBL-1 and maintained in culture for one to four passages. Fresh media was added to the KSHV-infected HDMEC and supernatants were collected 24 hours later for analysis by ELISA. Results are the mean of four experiments (±S.D.);

FIG. 34A. HIV-1 and KSHV act synergistically on IL-8 production. PBM were obtained by culturing the adherent fraction of PBMC from a healthy volunteer for three days. These adherent MDM were then detached by EDTA treatment and then co-cultured with HDMEC just prior to treatment with no virus (Control), HIV-$1_{BRU}$, KSHV, or both viruses. Conditioned media were collected after 24 hours for analysis by ELISA; and FIG. 34B. HIV-1 and KSHV act synergistically on GRO-α production. PBM were obtained by culturing the adherent fraction of PBMC from a healthy volunteer for three days. These adherent MDM were then detached by EDTA treatment and then co-cultured with HDMEC just prior to treatment with no virus (Control), HIV-$1_{BRU}$, KSHV, or both viruses. Conditioned media were collected after 24 hours for analysis by ELISA.

DETAILED DESCRIPTION OF THE PREFERRED EMBODIMENTS

Methods for suppressing or inhibiting viral replication in infected host cells are provided. In one embodiment, a method of the present invention comprises treating the infected host cell with an inhibitor of C-X-C chemokines or C-X-C chemokine receptors. In a preferred embodiment, the host cell is infected with human immunodeficiency virus (HIV) or Kaposi's sarcoma herpesvirus (KSHV). In an alternate preferred embodiment, the host cell is either a monocyte or a T-cell.

Figure 1:
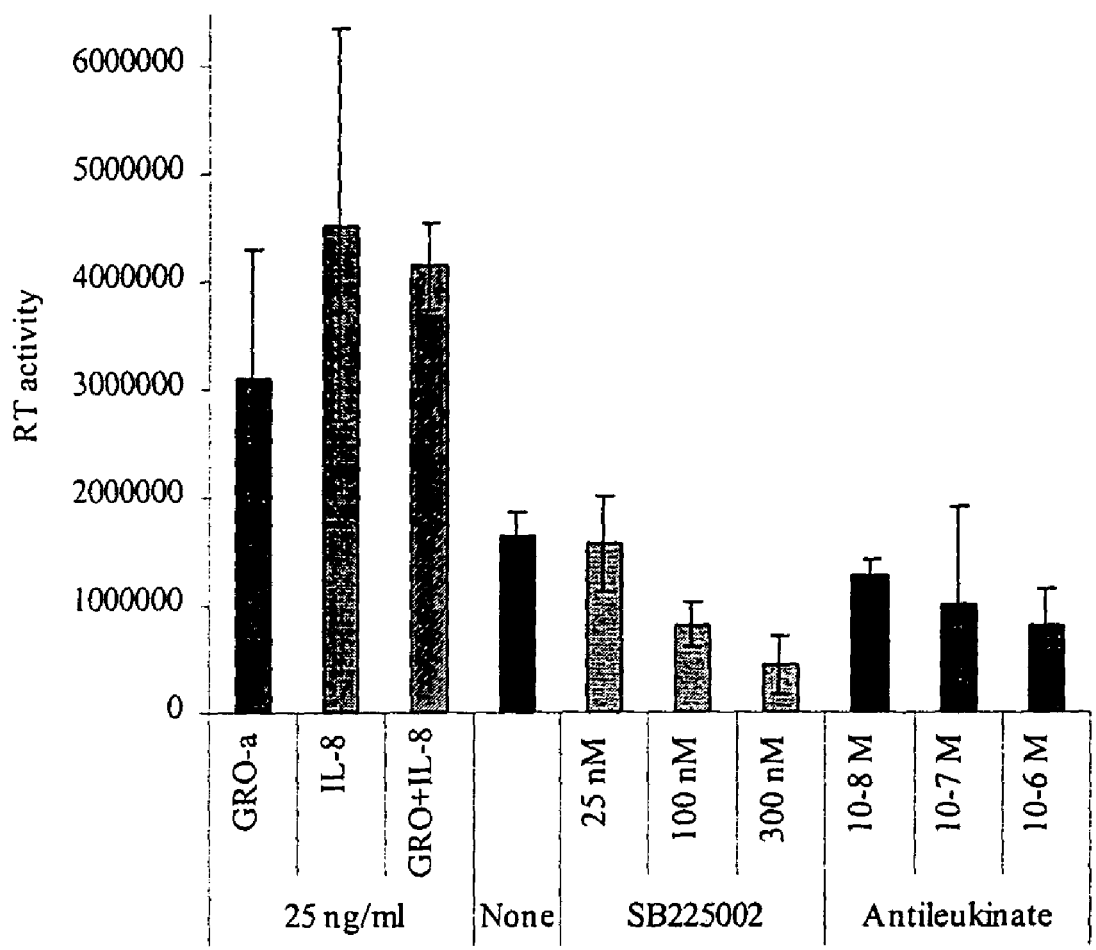
FIG. 1. GRO-$\alpha$ and IL-8 stimulate, while agents that interfere with their actions inhibit HIV-1 replication in monocyte-derived macrophages (MDM). MDM were treated with either GRO-$\alpha$ and IL-8 alone or in combination at 25 ng/ml, or SB225002 or antileukinate at the doses indicated. MDM were treated every three days beginning one day before infection. RT activity was measured in supernatants collected every three days. The data represent the mean of the RT activity present in triplicate wells at the peak of viral replication in this experiment (day 13) and are representative of three independent experiments with each inhibitor and at least ten with each chemokine.
Figure 8A:
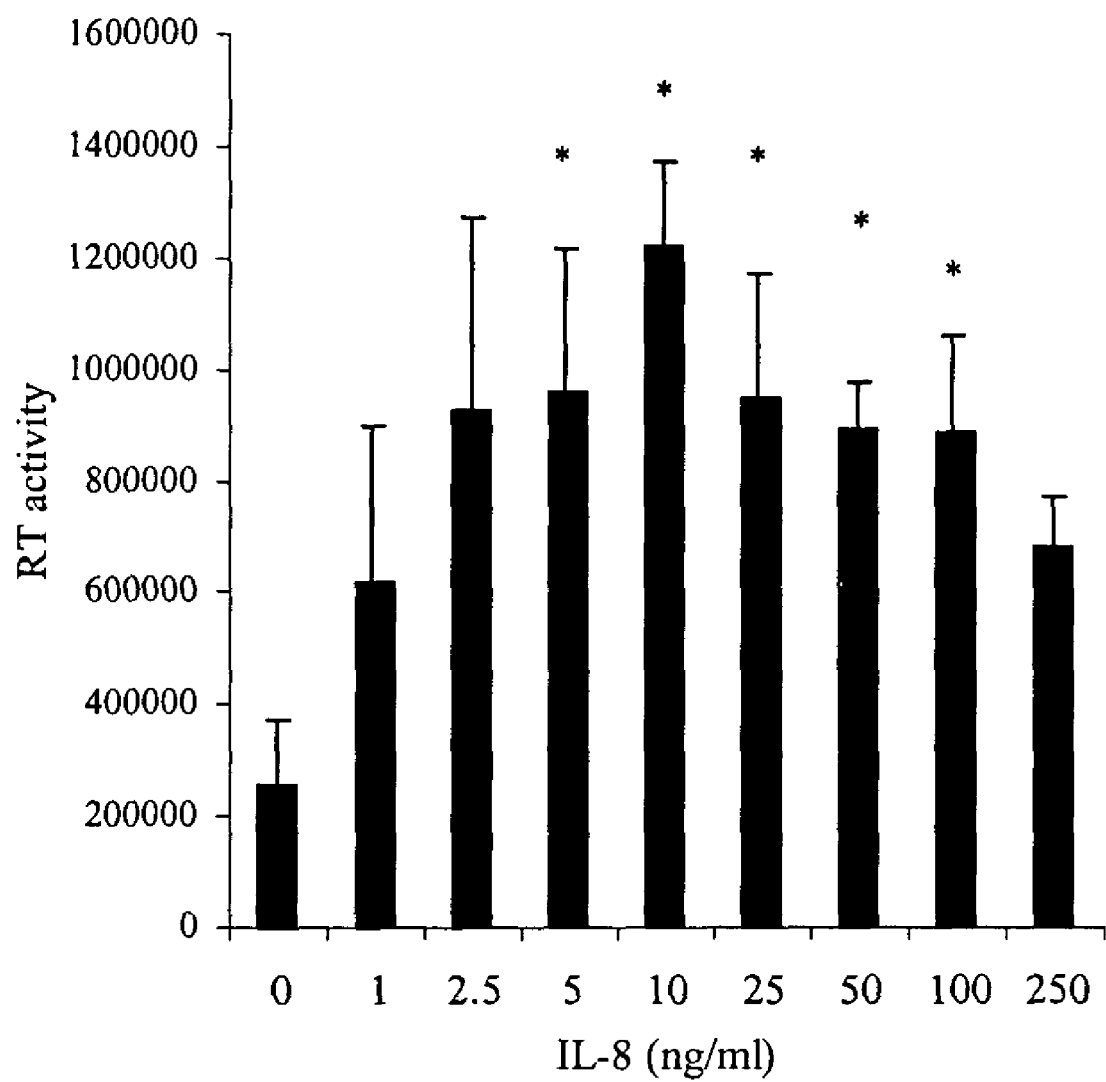
FIG. 8A. Exogenous IL-8 stimulates HIV-1 replication in MDM and CD8-depleted PBL. MDM were treated with IL-8 at the indicated concentrations beginning 16 hours before infection with HIV-$1_{BaL}$. Supernatants were analyzed for RT activity 8 days after infection.

C-X-C chemokines have been found to stimulate HIV and KSHV viral replication in host cells (FIGS. 1 and 8A). This result was surprising and unexpected in light of the prior art which taught that the C-X-C chemokine, IL-8, had either no effect or a modest inhibitory effect on HIV replication. Capobianchi, M. R. et al., *AIDS Res. Hum. Retroviruses* 14, 233–40 (1998); Mackewicz, C. E. et al., *Cell Immunol.* 153, 329–43 (1994); Nagira, M. et al., *Virology* 264, 422–6 (1999). In the present invention, inhibitors that interfere with the binding of C-X-C chemokines to their receptors actually suppress viral replication of HIV and KSHV.

C-X-C chemokines are chemokines in which the first two cysteine residues in the chemokine amino acid sequence are separated by an additional amino acid. Examples of C-X-C chemokines are, but not limited to, IL-8, IP-10, GRO-α, GRO-β, GRO-γ, GCP-2, ENA-78, NAP-2, ENA-78, I-TAC, MIG and BLC. Examples of C-X-C chemokine receptors are, but not limited to, CXCR1, CXCR2, CXCR3, CXCR4 and CXCR5. CXCR4 has been shown to be involved in the transport of viruses, specifically HIV, into the cell. It has been found in the present invention, however, that CXCR1, CXCR2, CXCR3 and CXCR5 are involved in viral replication. Blocking or interfering with the interaction of a C-X-C chemokine with its respective receptor suppresses viral replication. By way of non-limiting example, Table 1 lists several C-X-C chemokine receptors and their respective C-X-C chemokine ligands.

TABLE 1

| Receptor | Ligand |
|---|---|
| CXCR1 | IL-8, GCP-2 |
| CXCR2 | IL-8, GCP-2, GRO-α, GRO-β, GRO-γ, ENA-78, NAP-2 |
| CXCR3 | IP-10, 1-TAC, MIG |
| CXCR4 | SDF-1 |
| CXCR5 | BLC |

In one embodiment, the inhibitors used in the methods of the present invention are any compounds known to inhibit or interfere with binding of C-X-C chemokines to C-X-C chemokine receptors. Such compounds may be synthetic compounds, natural products, proteins or peptides, antibodies or nucleic acid molecules. Non-limiting examples of such inhibitors are N-(2-hydroxy-4-nitrophenyl)-N'-(2-bromophenyl)urea (SB225002), antileukinate, antibodies that neutralize chemokine activity and/or block receptor binding.

Figure 2:
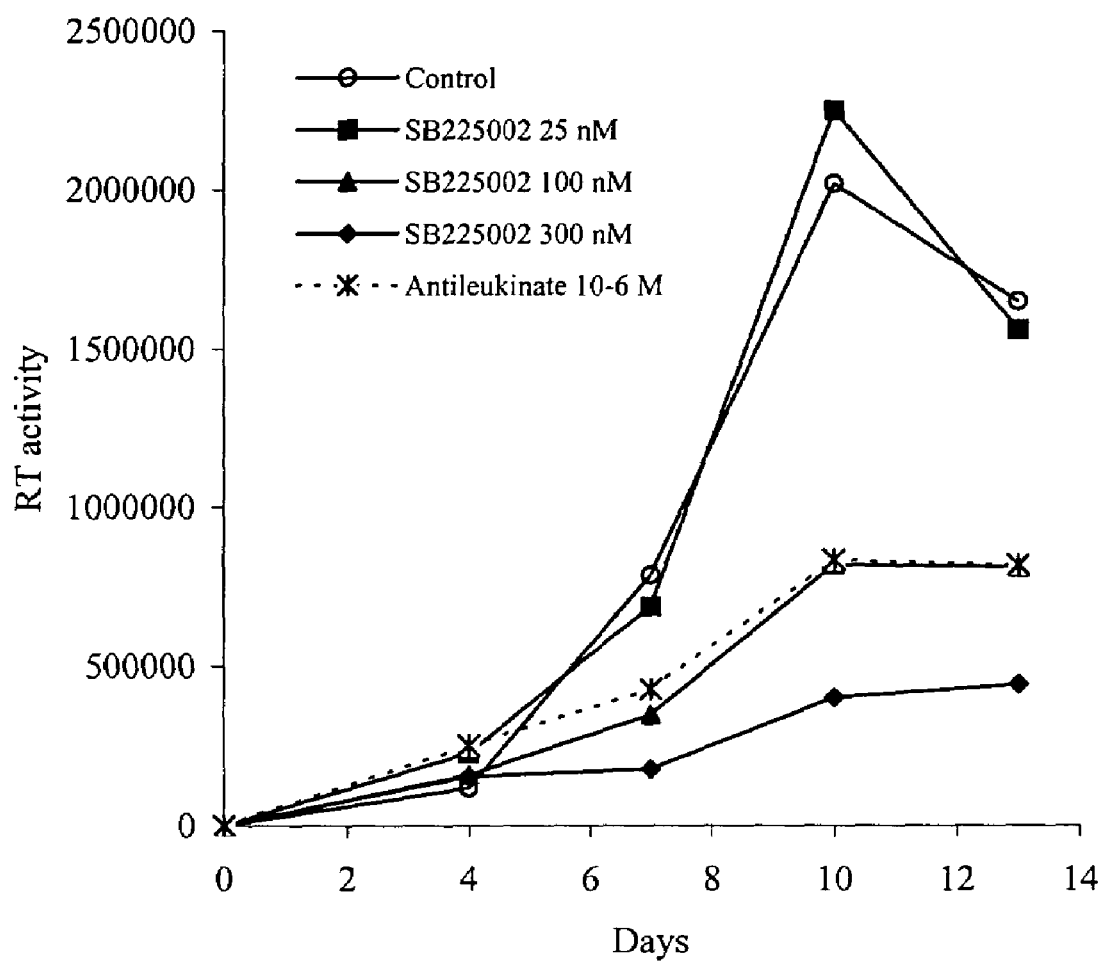
FIG. 2 is a graph showing the time course of HIV-1 replication in MDM treated with SB225002 [N-(2-hydroxy-4-nitrophenyl)-N'-(2-bromophenyl)urea] or antileukinate. MDM were treated with the inhibitors at the doses indicated every three days beginning one day before infection. The data shown are the mean of the RT activity present in triplicate wells measured on the days indicated.
Figure 3:
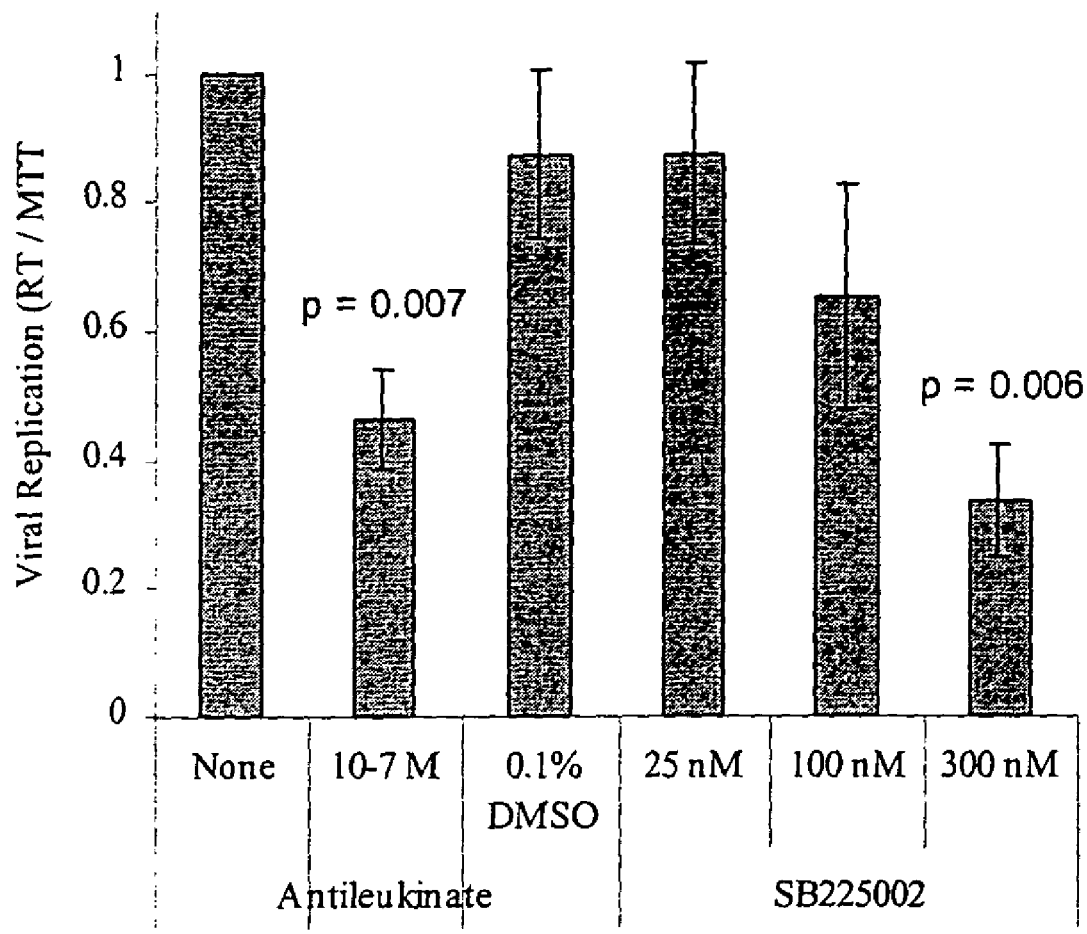
FIG. 3. Antileukinate and SB225002 significantly decrease HIV replication in MDM. MDM were treated as in FIGS. 1 and 2, and RT activity was measured every three to four days. MDM were also analyzed on day 13 by MTT assay (a measure of cellular viability, proliferation, and activation). Viability and activation was changed by less than 20% at all of the doses evaluated. For each treatment, viral replication was normalized against viability (RT activity/MTT assay) and then expressed relative to the control (no treatment). Data shown are the mean of three experiments.

In a preferred embodiment, the inhibitor is SB225002, a small molecular weight inhibitor that is an antagonist of IL-8 binding to CXCR2. In an alternate preferred embodiment, the inhibitor is antileukinate, a synthetic peptide inhibitor that interferes with both IL-8 and GRO-α binding to receptors. Both SB225002 and antileukinate effectively suppressed HIV replication in monocyte-derived macrophages and T-cells. Infection of PBL with HIV-1$_{BRU}$ was inhibited by both the small molecule inhibitor, SB225002 (FIG. 29A), and the peptide, antileukinate (FIG. 29B). In experiments with T cells from three different donors, antileukinate significantly decreased HIV replication (3.6±1.4-fold; p=0.034). Both inhibitors also reduced HIV-1$_{BaL}$ replication in MDM (FIGS. 1–3). Cellular viability, proliferation, and activation were also analyzed in the infected cells by performing an MTT assay. The doses of SB225002 used did not negatively affect cellular viability in T cells or MDM, indicating a lack of toxicity. Similarly, doses of antileukinate up to $10^{-4}$ M in PBL and $10^{-6}$ M in MDM reduced cellular viability by not more than 20%, and doses as low as $10^{-8}$ M were effective at inhibiting HIV-1 replication. Importantly, both inhibitors reduced HIV-1 replication in every donor tested, and these differences were statistically significant. The mean decreases in HIV-1$_{BaL}$ replication in MDM were 4.0±1.3 for 1000 nM SB225002 (p=0.019) and 2.6±0.6 for $10^{-6}$ M antileukinate (p=0.002) relative to controls.

In yet another preferred embodiment, the inhibitor is an antibody that neutralizes chemokine activity, such as, but not limited to anti-GRO-α, anti-IL-8, and anti-IP-10 and antibodies that block receptor binding such as, but not limited to, anti-CXCR1, anti-CXCR2 and anti-CXCR3. Antibodies to C-X-C chemokines and their receptors are potent inhibitors of HIV replication (FIGS. 10A–B, 28 and 31A–C). It will be appreciated by those skilled in the art that a combination of inhibitors may be used to suppress or inhibit viral replication.

In an alternate embodiment, the method of the present invention comprises treating a virus-infected host cell with a molecule that inhibits or suppresses the expression of C-X-C chemokines or C-X-C chemokine receptors. By way of non-limiting example, the infected host cell may be treated with antisense nucleic acid molecules specific for the gene encoding at least one C-X-C chemokine or at least one C-X-C chemokine receptor. Preferably, the chemokine is IL-8, GRO-α or IP-10. Alternatively, the preferred C-X-C receptor is CXCR1, CXCR2, CXCR3 or CXCR5. Inhibition or suppression of expression of C-X-C chemokines and/or C-X-C chemokine receptors will then suppress or inhibit viral replication.

In a further embodiment, a method is provided for treating viral infections comprising administering to a patient diagnosed with a viral infection, a therapeutically effective amount of an inhibitor that blocks or interferes with the interaction of C-X-C chemokines with C-X-C chemokine receptors. Treatment of the viral infected cells in the viral infection with such an inhibitor or inhibitors results in suppression of viral replication. Suppression of viral replication with the method of the present invention may result in suppression or a slowing down of the development of the disease. Treatment can also provide a decrease of any symptoms of the viral infection that are present. The methods of the present invention are particularly useful in treating patients suffering from HIV infection to prevent the development of full blown AIDS. The methods of the present invention are also useful for treating a patient having AIDS. The methods of the present invention are also useful for treating patients suffering from Kaposi's Sarcoma. Kaposi's Sarcoma is an opportunistic tumor that often affects patients having an HIV infection. The methods of the present invention are particularly useful for treating patients having both an HIV infection and Kaposi's Sarcoma.

As used herein, the term "inhibitors of C-X-C chemokines" preferably mean any compound or substance which inhibits the action of the chemokines, preferably by inhibiting, blocking, or interfering with the binding of a chemokine to its respective receptor. The term "inhibitors of C-X-C chemokine receptors" preferably mean any compound or substance which inhibits or interferes with the binding of the C-X-C chemokine to the receptor by acting on the receptor. It is contemplated that the inhibitors of the present invention are directed either toward a C-X-C chemokine or a C-X-C chemokine receptor to inhibit or interfere with the productive binding of the chemokine to its receptor. The inhibitors may be, but are not limited to, small molecules, peptides, proteins, antibodies and nucleic acids.

As used herein, the terms "therapeutically effective amount" and a "therapeutically effective duration" preferably mean the total amount of each active component of the pharmaceutical composition and a duration of treatment that is sufficient to show a meaningful patient benefit, i.e., treatment, healing, prevention or amelioration of the relevant medical condition, or an increase in rate of treatment, healing, prevention or amelioration of such conditions without undue adverse physiological effects or side effects. The term "therapeutically effective amount," when applied to an individual active ingredient, administered alone, the term refers to that ingredient alone. When applied to a combination, the term refers to combined amounts of the active ingredients, e.g., C-X-C chemokine inhibitors, C-X-C chemokine receptor inhibitors or a combination of both, that result in the therapeutic effect, whether administered in combination, serially or simultaneously.

An inhibitor of C-X-C chemokines or chemokine receptors of the present invention may thus be used in a pharmaceutical composition when combined with a pharmaceutically acceptable carrier. Such a composition may also contain (in addition to inhibitors of C-X-C chemokines or chemokine receptors and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s).

In practicing the method of treatment or use of the present invention, a therapeutically effective amount of inhibitors of C-X-C chemokines or chemokine receptors of the present invention are administered to a patient having a condition to be treated, e.g., HIV infection. Inhibitors of C-X-C chemokines or chemokine receptors of the present invention may be administered in accordance with the method of the invention either alone or in combination, including in combination with other conventional therapies. For example, inhibitors of C-X-C chemokines or chemokine receptors can be used as part of a multidrug regime.

Administration of inhibitors of C-X-C chemokines or chemokine receptors of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection.

When a therapeutically effective amount of an inhibitor of C-X-C chemokines or chemokine receptors of the present invention is administered orally, the inhibitor of C-X-C chemokines or chemokine receptors of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% C-X-C chemokines or chemokine receptors inhibitors of the present invention, and preferably from about 25 to 90% inhibitors of C-X-C chemokines or chemokine receptors of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical compositions may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of inhibitors of C-X-C chemokines or chemokine receptors of the present invention and preferably from about 1 to 50% inhibitors of C-X-C chemokines or chemokine receptors of the present invention.

When a therapeutically effective amount of an inhibitor of C-X-C chemokines or chemokine receptors of the present invention is administered by intravenous, cutaneous or subcutaneous injection, the inhibitor will be in the form of a pyrogen-free, parenterally acceptable aqueous solution. The preparation of such parenterally acceptable C-X-C chemokines or chemokine receptors inhibitor solutions, having due regard to pH, isotonicity, stability, and the like, is within the skill in the art. A preferred pharmaceutical composition for intravenous, cutaneous, or subcutaneous injection should contain, in addition to inhibitors of C-X-C chemokines or chemokine receptors, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of inhibitors of C-X-C chemokines or chemokine receptors of the present invention in the pharmaceutical composition of the present invention will depend upon the nature and severity of the condition being treated, and on the nature of prior treatments which the patient has undergone. Ultimately, the attending physician will decide the amount of inhibitors of C-X-C chemokines or chemokine receptors of the present invention with which to treat each individual patient. Initially, the attending physician will administer low doses of inhibitors of C-X-C chemokines or chemokine receptors and observe the patient's response. Larger doses of inhibitors of C-X-C chemokines or chemokine receptors may be administered until the optimal therapeutic effect is obtained for the patient, and at that point the dosage is not increased further.

It must be noted that, as used in this specification and the amended claims, the singular forms "a", "an", and "the" include plural referents unless context clearly dictates. Thus, for example, a reference to "an inhibitor of C-X-C chemokines or chemokine receptors" includes mixtures of such inhibitors.

examples, which are presented for purposes of illustration and not by way of The foregoing may be better understood in connection with the following limitation.

SPECIFIC EXAMPLE I

IL-8 Stimulates HIV Replication

Results

Figure 4A:
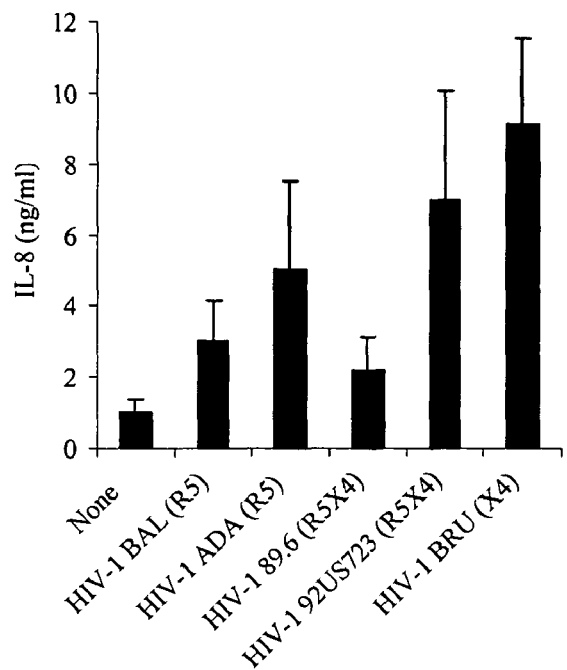
FIG. 4A. Exposure to HIV-1 stimulates IL-8 production by MDM. Production of IL-8 by MDM following encounter with HIV-1 is independent of coreceptor usage. MDM were exposed to the R5 isolates HIV-1$_{BaL}$ and HIV-1$_{ADA}$; the R5X4 isolates HIV-1$_{89.6}$ and HIV-1$_{92US723}$; and the X4 isolate HIV-1$_{BRU}$. Supernatants were collected 2 days after infection and stored at $-70°$ C. until analysis. Extracellular immunoreactive IL-8 was measured by ELISA. Data are the mean ($\pm$SEM) of three independent experiments.
Figure 4B:
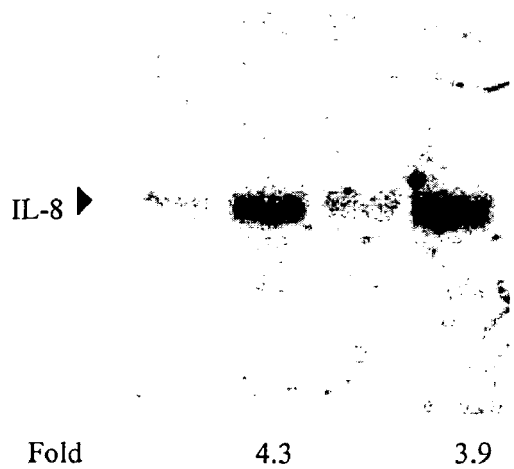
FIG. 4B. Total cellular RNA was extracted from control MDM ($-$) and MDM exposed to HIV-1$_{BRU}$ ($+$) after 2 days. RNA from two different donors was then analyzed for IL-8 gene expression by northern (RNA) blot analysis using an IL-8-specific probe. The amount of IL-8 mRNA was normalized to the amount of rRNA in each sample and the fold increase in HIV-exposed MDM relative to control MDM is indicated.
Figure 5:
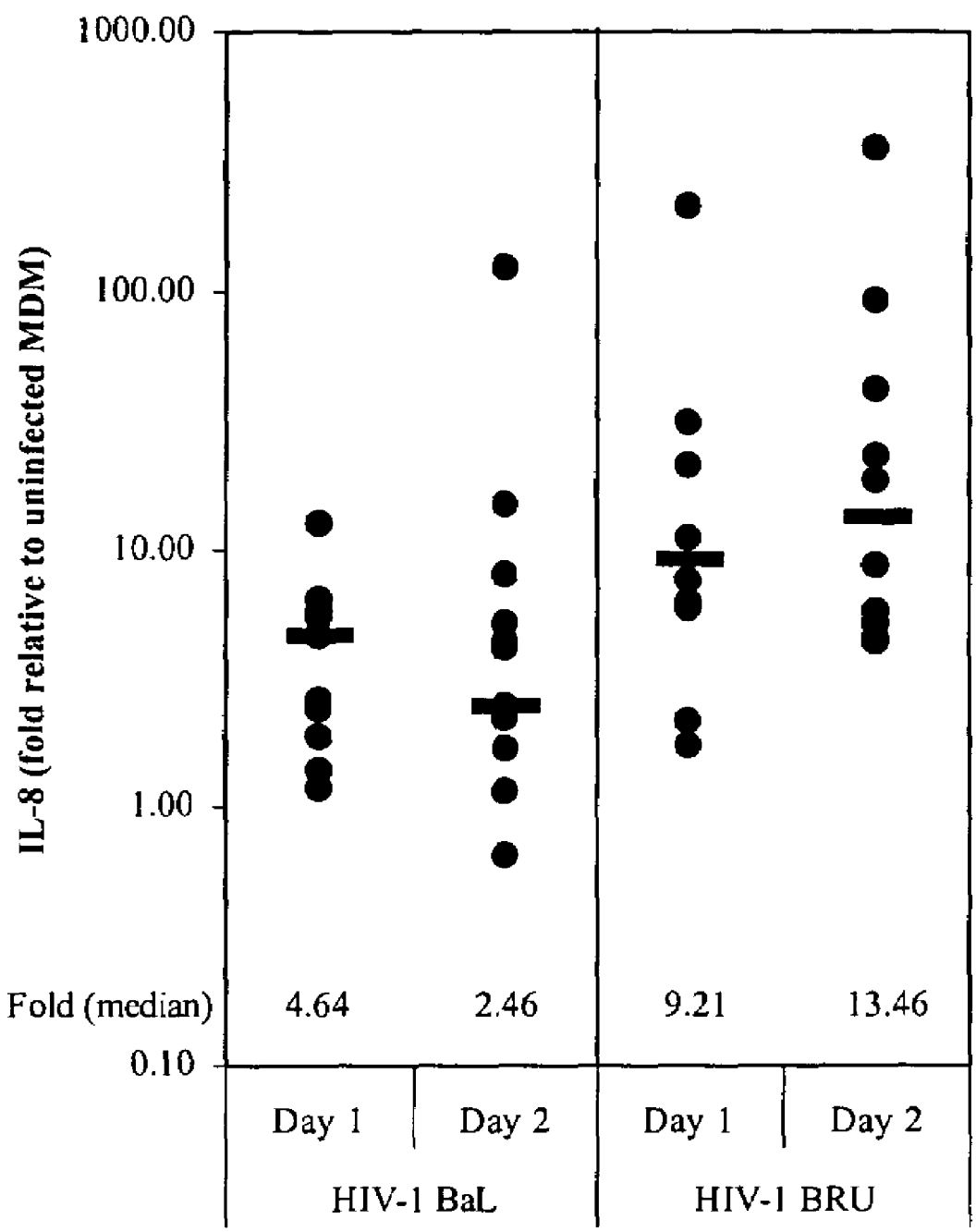
FIG. 5. Exposure to R5 HIV (HIV-1$_{BaL}$) and X4 HIV (HIV-1$_{BRU}$) stimulates IL-8 production by MDM. Data shown are the results of ELISA for IL-8 performed on the supernatants collected 1 and 2 days after exposure of MDM from at least 10 different donors to HIV-1. Each point on this logarithmic scale indicates the fold increase relative to uninfected MDM for one donor. The horizontal bars and data labels indicate the median values.

Production of IL-8 by Monocyte-Derived Macrophages (MDM) Exposed to HIV-1: Encounter with HIV-1 virions or the viral envelope glycoprotein gp120 stimulates the production of TNF-α, by binding to CD4, and GRO-α, via interaction with the chemokine receptor CXCR4. Merrill, J. E. et al., *J Virol* 63, 4404–8 (1989). Isolates of HIV-1 that use CXCR4 as an entry cofactor (X4 HIV) stimulate far greater production of GRO-α than those that use CCR5 (R5 HIV). In contrast, when IL-8 production by MDM was examined following encounter with several isolates of HIV-1, an increase in levels of IL-8 was found independent of coreceptor usage (FIG. 4A). In experiments with MDM from 11 different donors, the stimulation of IL-8 production was similar after encounter with either a prototypical R5 HIV isolate, HIV-$1_{BaL}$ (median increase: 4.64 fold), or an X4 HIV isolate, HIV-$1_{BRU}$ (median increase: 9.21 fold) (FIG. 5). Northern blot analysis of MDM exposed to HIV-$1_{BRU}$ indicated a nearly four-fold increase in the steady state RNA level of IL-8 (FIG. 4B). This change in mRNA is consistent with the increase detected at the protein level by ELISA, indicating that the increase in IL-8 levels is largely due to an activation of transcription. These data indicate that exposure of both lymphocytes and monocytes to HIV-1 increases IL-8 production and unlike the case of GRO-α increased IL-8 production is not a response specific to encounter with isolates of HIV-1 that bind to CXCR4.

Figure 6:
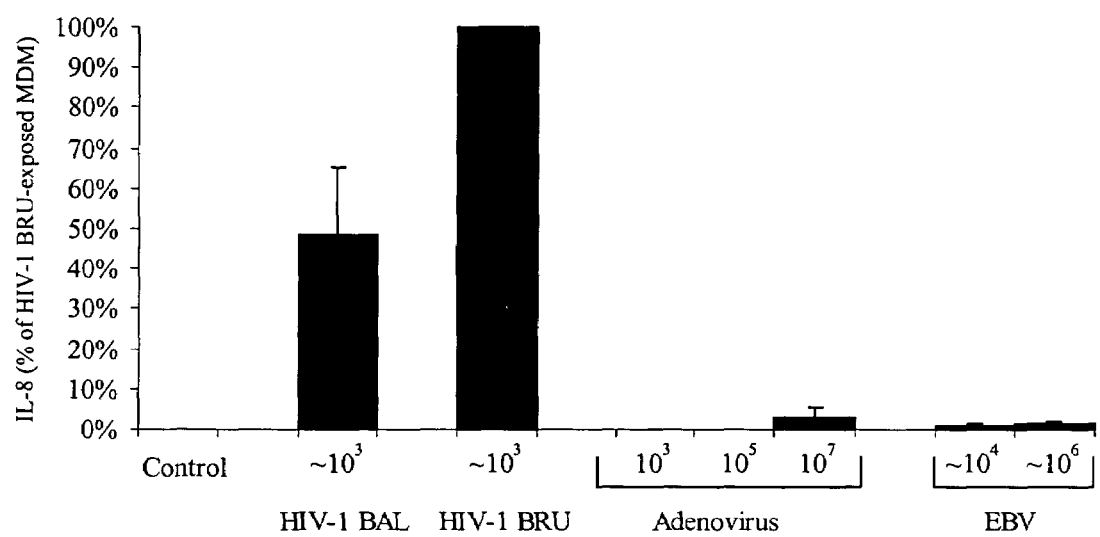
FIG. 6. MDM produce IL-8 in response to HIV-1, but not to adenovirus or Epstein-Barr virus (EBV), Type I. The number of viral particles added to $\sim 10^5$ MDM is indicated. Data are the mean values of multiple wells of MDM from two donors$\pm$standard deviation.

The specificity of the production of IL-8 by MDM following interaction with HIV-1 was further investigated. Assays of viral stocks showed that they contained virtually no lipopolysaccharide (LPS, <0.016 EU/100 μl) and polymixin B did not prevent the HIV-induced increase in IL-8 production. MDM exposed to neither adenovirus nor Epstein-Barr virus (EBV) produced increased amounts of IL-8 (FIG. 6). Thus, IL-8 is not produced simply because MDM are activated non-specifically by viral antigens or by LPS in the preparations of virus. Rather, these data indicate that MDM produce IL-8 specifically in response to encounter with HIV-1.

IL-8 Production by Peripheral Blood Mononuclear Cells (PBMC): In order to analyze the production of IL-8 by individual cells, the presence of IL-8 in PBMC following encounter with HIV-1 was observed by flow cytometry. Fresh PBMC were cultured overnight without PHA stimulation and then exposed to small numbers of HIV-$1_{BaL}$ or HIV-$1_{BRU}$ virions or TNF-α. Staining after 6 hours revealed that IL-8 was present in >90% of CD14+ monocytes treated with either HIV-$1_{BRU}$ or TNF-α, in 57% of CD14+ monocytes treated with HIV-$1_{BaL}$, and in 10% of control monocytes (FIGS. 7A–C). IL-8 staining was detected in less than 5% of CD4+ lymphocytes in all conditions (FIGS. 7A–C). Similarly, while PHA-activated PBL constitutively produce appreciable levels of IL-8, HIV does not greatly stimulate IL-8 production by PBL above this endogenous level (Table 2). Therefore, the major cellular target of HIV induction of IL-8 production are mononuclear phagocytes.

TABLE 2

IL-8 production by PHA-activated PBL.

| | | IL-8 (ng/ml) | |
|---|---|---|---|
| | Days after infection | Uninfected | HIV-$1_{BaL}$ |
| Donor 1 | 2 | 2.3 | 9.6 |
| Donor 2 | 2 | 0.10 | 2.2 |
| Donor 3 | 7 | 5.1 | 7.7 |
| Donor 4 | 7 | 0.289 | 0.453 |
| Donor 5 | 10 | 0.57 | 0.54 |
| Donor 6 | 10 | 1.1 | 2.3 |

Figure 8B:
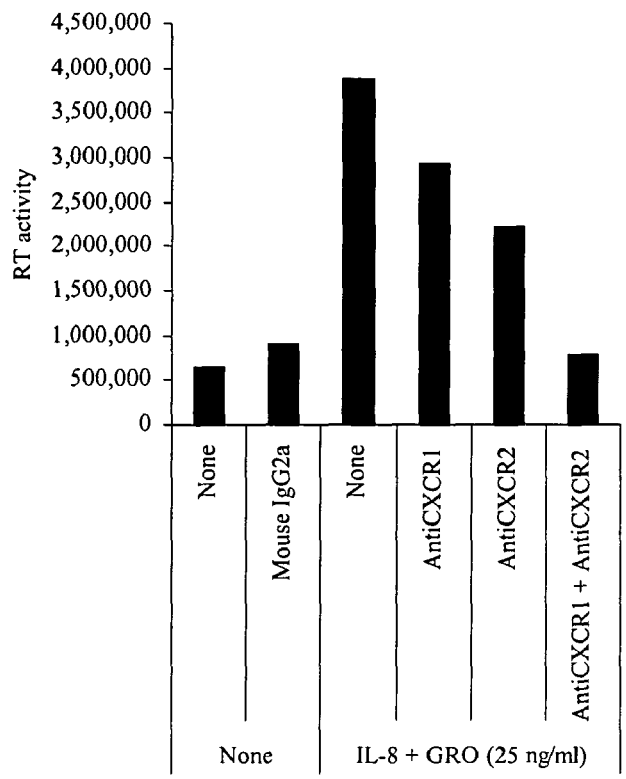
FIG. 8B. Antibodies to CXCR1 and CXCR2 block the ability of IL-8 and GRO-α (each at 25 ng/ml) to stimulate HIV-$1_{BaL}$ replication. Supernatants were analyzed for RT activity 19 days after infection.

Exogenous and Endogenous IL-8 Stimulates HIV-1 Replication in MDM and CD8: Previous studies have found increased IL-8 in the serum and tissue of HIV-infected individuals, but none have implicated IL-8 in HIV pathogenesis Capobianchi, M. R. et al., *AIDS Res Hum Retroviruses* 14, 233–40 (1998); Denis, M. et al., *AIDS Res Hum Retroviruses* 10, 1619–27 (1994); Lafrenie, R. M. et al., *J Immunol* 159, 4077–83 (1997); Matsumoto, T. et al., *Clin Exp Immunol* 93, 149–51 (1993); Ott, M. et al., *J Immunol* 160, 2872–80 (1998). As certain chemokines (RANTES, MIP-1α, MIP-1β, SDF-1α) have been demonstrated to play important roles in HIV-1 pathogenesis, mainly as inhibitors of viral entry (Bleul, C. C. et al., *Nature* 382, 829–33 (1996); Bleul, C. C. et al., *J Exp Med* 184, 1101–9 (1996); Cocchi, F. et al., *Science* 270, 1811–1815 (1995); Oberlin, E. et al., *Nature* 382, 833–835 (1996)), the effect of IL-8, and signaling through its receptors CXCR1 and CXCR2, on HIV replication in MDM and T lymphocytes was studied. Replication of the macrophage-tropic R5 isolate HIV-$1_{BaL}$ in MDM was augmented by the addition of exogenous IL-8 (FIG. 8A). In experiments performed with MDM from 17 different donors, IL-8 increased HIV-1 replication in 15 of the 17 donors (mean: 6.2-fold; range: 0.5- to 50-fold). The stimulatory effect of IL-8 on HIV-1 replication was additive to that of GRO-α, and the effects of IL-8 and GRO-α on HIV-1 replication were blocked by a combination of antibodies that prevent interaction with CXCR1 and CXCR2 (FIG. 8B). Importantly, no viral replication was detected when MDM from multiple donors were infected with HIV-$1_{BRU}$ in the presence or absence of exogenous IL-8, indicating that IL-8 does not confer susceptibility to productive infection with X4 HIV on MDM. These data indicate that, in addition to the stimulatory effect of HIV-1 on IL-8 production, IL-8, acting through its receptors (CXCR1 and CXCR2) can also enhance HIV-1 replication in primary human MDM.

Figure 8C:
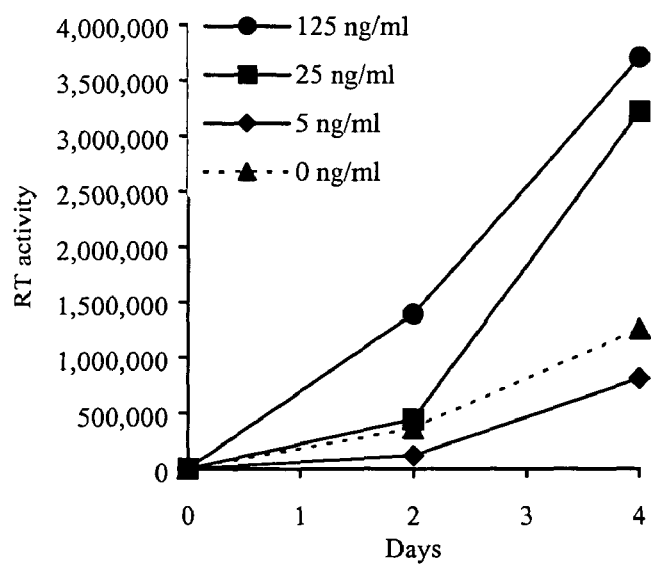
FIG. 8C. CD8-depleted PBL were treated with the indicated concentrations of IL-8 and infected with HIV-$1_{BRU}$. Data shown are representative of at least five experiments.
Figure 9:
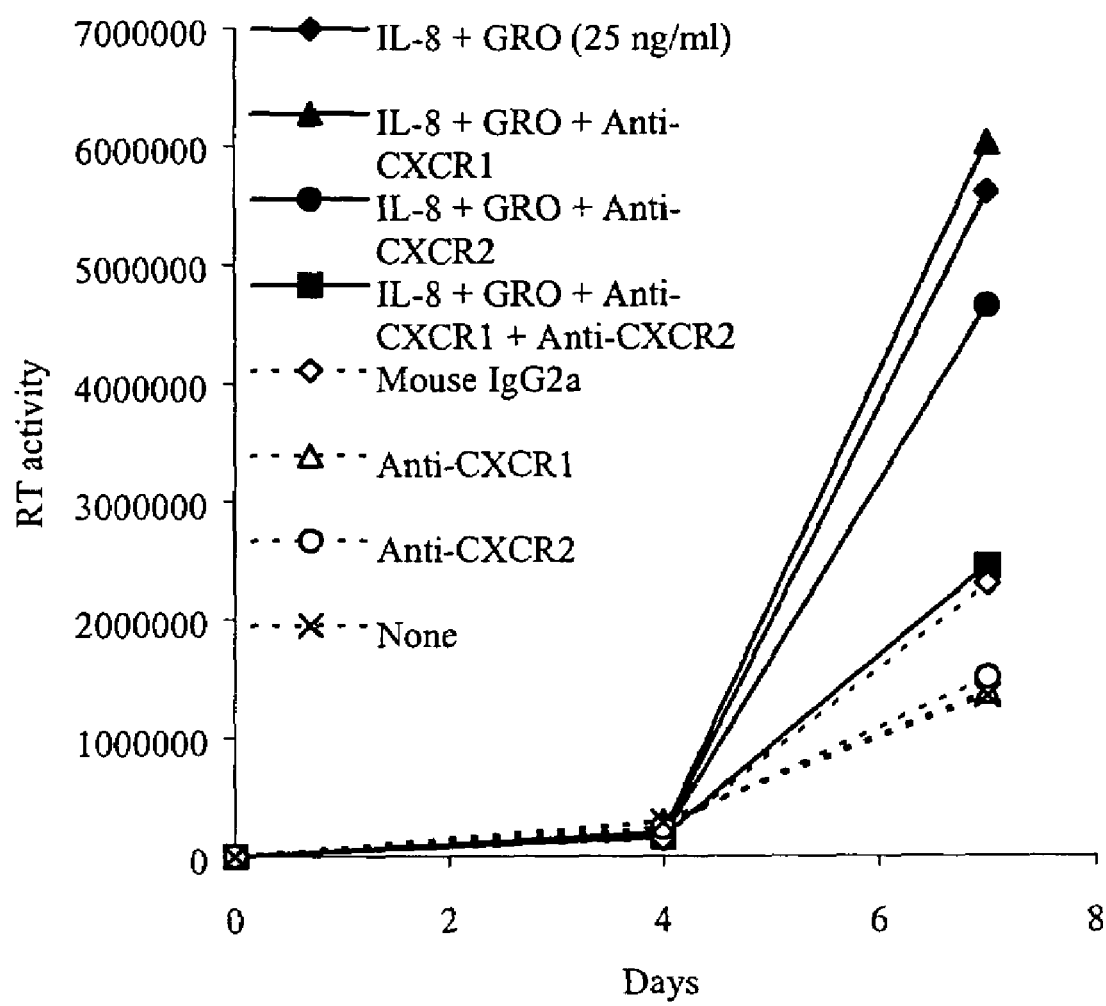
FIG. 9. Antibodies to CXCR1 and CXCR2 (20 µg/ml) block the ability of IL-8 and GRO (each at 25 ng/ml) to stimulate HIV-$1_{BaL}$ replication in CD8-depleted PBL. Media was collected and replenished twice weekly. Supernatants were analyzed for RT activity four and seven days after infection.

The effect of IL-8 on HIV-1 replication in CD4+ T lymphocytes was then investigated. Addition of IL-8 in doses exceeding 5 ng/ml stimulated viral replication in PHA-activated, CD8-depleted PBL (FIG. 8C). HIV-$1_{BRU}$ replication was increased in all 5 donors tested (mean: 1.7-fold; range: 1.1- to 3.0-fold). Replication of the R5 isolate HIV-$1_{BaL}$ in activated PBL was stimulated in 10 of the 11 donors tested (mean: 4.8-fold; range: 0.8- to 19-fold) by the addition of IL-8. In fact, IL-8 stimulated the replication of all other isolates tested, including both R5 and X4 isolates of HIV-1 and HIV-2. As observed with infection of MDM, the stimulatory effect of IL-8 is mediated through both CXCR1 and CXCR2, as anti-CXCR1 alone partially reduced, and anti-CXCR2 in combination with anti-CXCR1, completely reversed the stimulation of HIV-$1_{BaL}$ replication (FIG. 9).

Figure 10A:
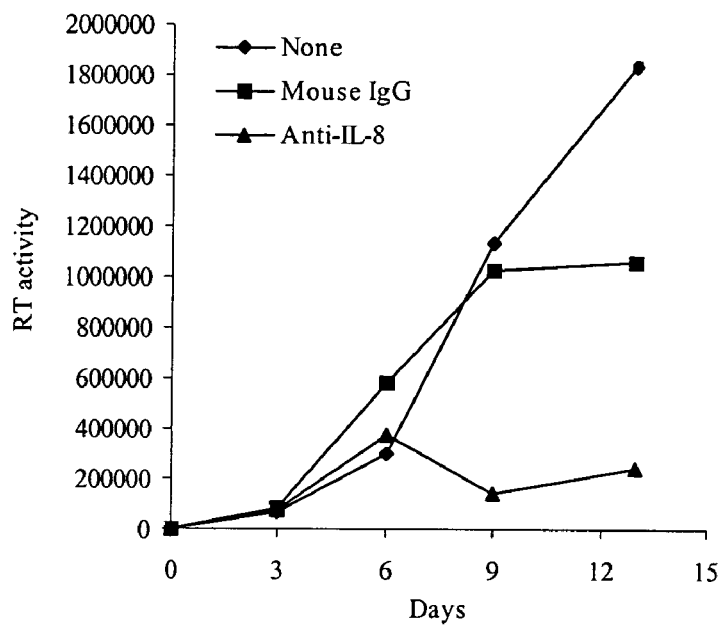
FIG. 10A. Depletion of endogenous IL-8 inhibits HIV-1 replication in MDM. MDM were treated with either mouse $IgG_1$ or an antibody that neutralizes IL-8 activity (each at 20 µg/ml) and infected with HIV-$1_{BaL}$. Media was collected for the RT assay and replenished twice weekly.
Figure 10B:
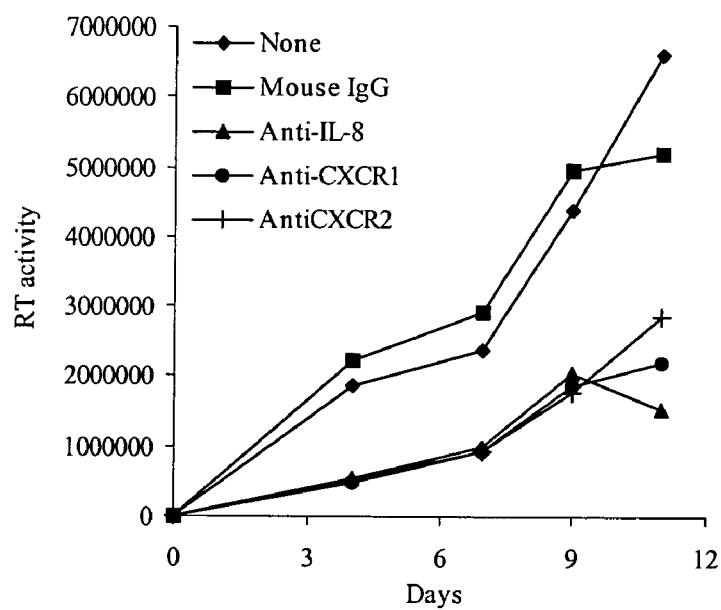
FIG. 10B. Immunodepletion of IL-8 or blocking the IL-8 receptors CXCR1 and CXCR2 suppresses HIV-1 replication in CD8-depleted PBL. CD8-depleted PBL were treated with the indicated antibodies (20 µg/ml) and infected with HIV-$1_{BRU}$. Media was collected and replenished twice weekly. Supernatants were analyzed for RT activity on the number of days after infection as indicated.

The dose-response studies indicated that smaller amounts of IL-8 (5 to 125 ng/ml) stimulated HIV replication, while higher levels did not have a significant effect (FIG. 8A). These amounts of IL-8 are similar to those induced by exposure of MDM to HIV and produced constitutively by activated PBL (FIGS. 4A–B), indicating that endogenous IL-8 may control HIV replication in MDM and PBL. In order to test this hypothesis, HIV-infected cells were incubated with antibodies known to antagonize IL-8 function. Addition of an antibody that neutralizes the activity of IL-8 (anti-IL-8) markedly reduced HIV-1$_{BaL}$ replication in MDM (FIG. 10A). Thus, in addition to the stimulatory effect of exogenous IL-8, endogenous IL-8 is essential to HIV-1 replication in MDM. Furthermore, when anti-IL-8, or antibodies that prevent interaction with the IL-8 receptors (anti-CXCR1, anti-CXCR2), were added to HIV-1$_{BRU}$-infected PBL, viral replication was reduced considerably (FIG. 10B). These data suggest that endogenous IL-8 production and signaling through CXCR1 and CXCR2 play stimulatory roles in HIV-1 replication in the two major targets of infection and point to the existence of an autocrine/paracrine loop involving IL-8 and HIV-1 replication.

Figure 11:
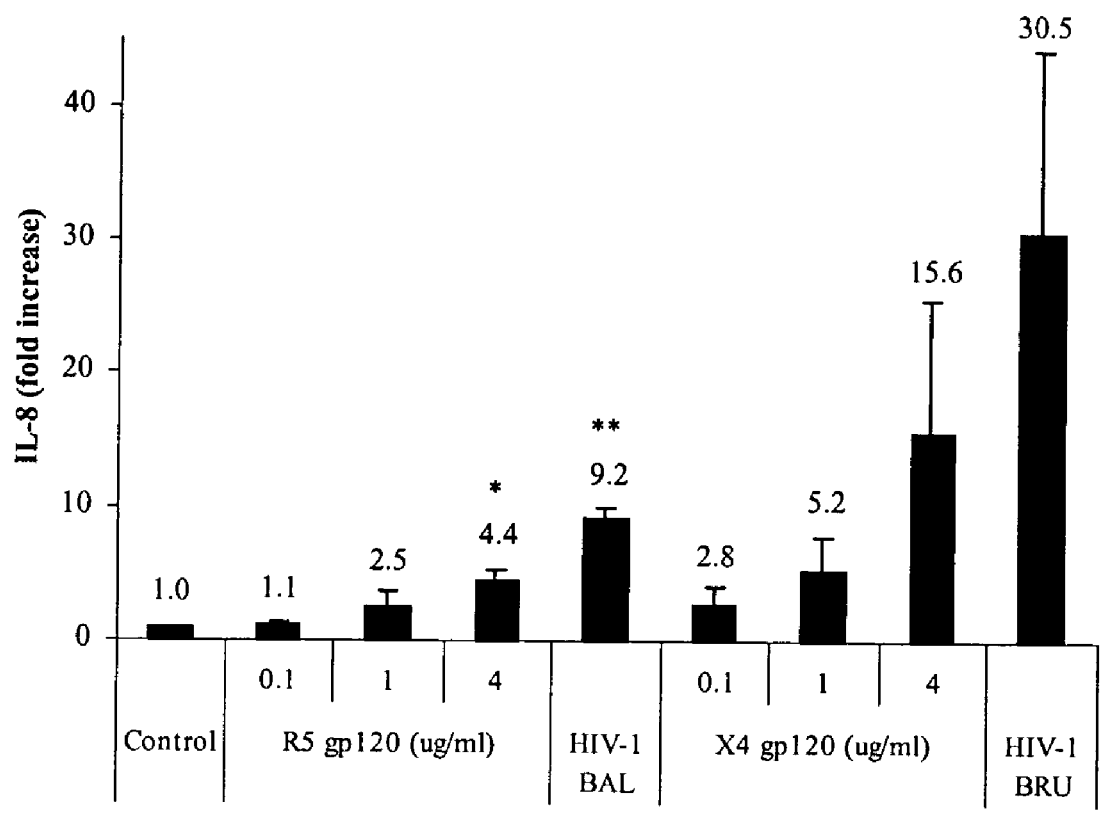
FIG. 11. HIV-1 gp120 stimulates IL-8 production by MDM. Supernatants were collected 2 days after treatment of triplicate cultures with either R5 gp120 (from HIV-$1_{93TH975}$), HIV-$1_{BaL}$, X4 gp120 (from HIV-$1_{IIIB}$), or HIV-$1_{BRU}$ as indicated. ELISA data shown are the mean values of three experiments (±standard deviation)

HIV-1 gp120 Stimulates IL-8 Production by MDM: It has previously been demonstrated that cytokine production by MDM is initiated by gp120 ligation of CD4 and CXCR4. Merrill, J. E. et al., *J Virol* 63, 4404–8 (1989). To determine whether a similar mechanism is responsible for the production of IL-8, MDM was incubated with soluble HIV-1 gp120 from R5 HIV and X4 HIV (FIG. 11). Both R5 and X4 gp120 stimulated IL-8 production, but not to the same extent as treatment with whole virus. Preparations of recombinant viral proteins were all found to have <1.6 EU LPS/μg protein. While this small amount of LPS was sufficient to stimulate some IL-8 production by MDM, treatment with polymixin B (10 μg/ml) prevented the LPS-mediated activity. In contrast, treatment with polymixin B did not prevent the increases in IL-8 stimulated by gp120 or Tat indicating that IL-8 production was not due to LPS contamination.

Figure 12:
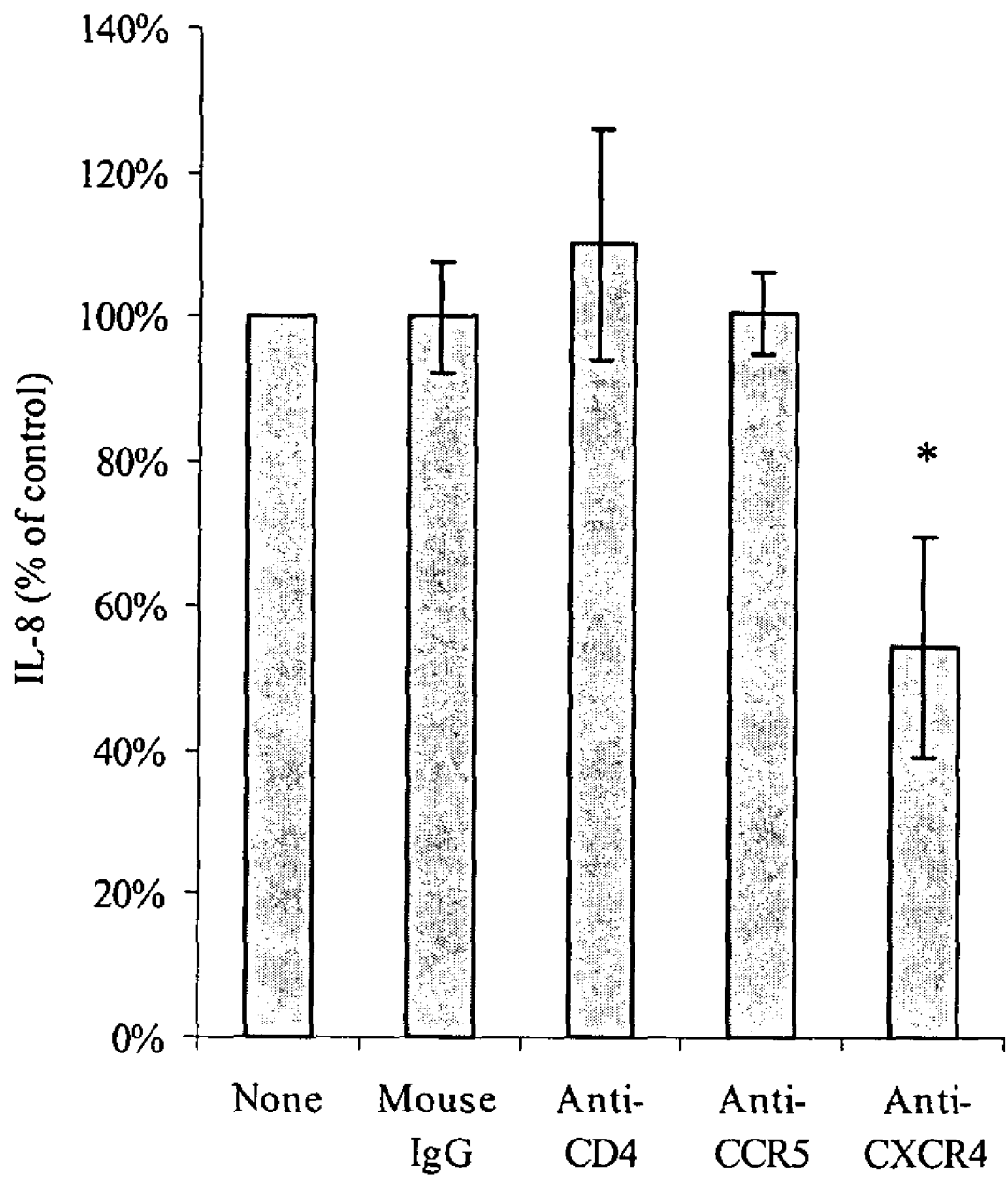
FIG. 12 is a graph showing the effect on IL-8 stimulation in MDM exposed to HIV-1 by antibodies to CD4, CCR5 and CXCR4.

In order to evaluate whether the induction of IL-8 by HIV was due to gp120 ligation of its receptors, MDM were incubated with antibodies that prevent interaction with either CD4, CCR5, or CXCR4, prior to exposure to HIV. Anti-CXCR4 attenuated the increase in IL-8 production with HIV-1$_{BRU}$ in part, while anti-CD4 and anti-CCR5 had no effect on IL-8 production stimulated by either HIV-1$_{BRU}$ or HIV-1$_{BaL}$ (FIG. 12). These data indicate that, contrary to the findings with GRO-α, while stimulation of MDM with HIV-1 gp120 leads to the production of IL-8, this can not be the only mechanism by which HIV-1 augments IL-8 production.

Figure 13A:
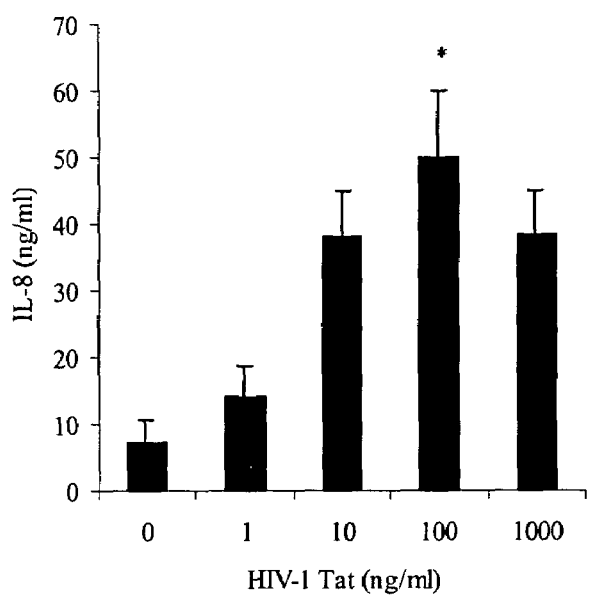
FIG. 13A. HIV-1 Tat triggers IL-8 production by MDM. Supernatants were collected 24 to 48 hours after infection and analyzed for IL-8 by ELISA. Dose response curve for HIV-1 Tat (1 to 1000 ng/ml). ELISA data are plotted as the mean of multiple wells from 2 experiments (±deviation). Statistical significance (*, p<0.05) was determined using a paired samples t test.
Figure 13B:
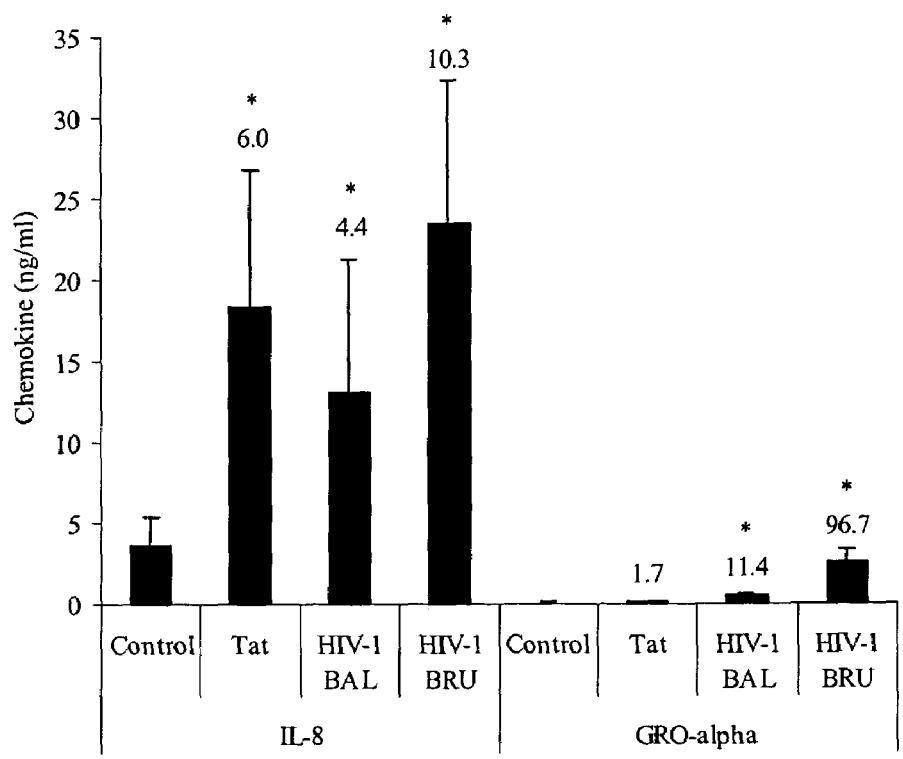
FIG. 13B. HIV-1 Tat triggers IL-8 production by MDM. Supernatants were collected 24 to 48 hours after infection and analyzed for IL-8 by ELISA. Recombinant HIV-1 Tat stimulates IL-8 and not GRO-α production by MDM as determined by ELISA. MDM were treated with either HIV-1 Tat (10 ng/ml), HIV-$1_{BaL}$, or HIV-$1_{BRU}$. Data shown are the mean of 5 experiments (±SEM). The mean increase relative to control is indicated above each bar. Statistical significance (*, p<0.05) was determined using the Wilcoxon signed ranks test for non-parametric data.

HIV-1 Tat and TNF-α Together Induce IL-8 Production by MDM: Previous studies have found that HIV-1 Tat, in concert with co-stimulatory signals, can stimulate IL-8 production in PBL and endothelial cells. Hofman, F. M. et al., *J Neuroimmunol* 94 28–39 (1999); Ott, M. et al., *J Immunol* 160, 2872–80 (1998). Therefore, whether Tat, and the inflammatory cytokines that are themselves regulated by HIV (Herbein, G. et al., *Clin Exp Immunol* 95, 442–9 (1994); Merrill, J. E. et al., *J Virol* 63, 4404–8 (1989); Poli, G. et al., *Cambridge, Mass.: Blackwell Scientific*, pp. 421–449 (1995)), might be involved in the stimulation of IL-8 production by MDM exposed to HIV-1 was investigated. Tat induced IL-8 production by MDM in a dose-dependent manner, with peak activity at 100 ng/ml (FIG. 13A). Indeed, recombinant HIV-1 Tat caused increases in IL-8 comparable to exposure to whole virus (FIG. 13B). In contrast, GRO-α production was not affected by Tat treatment, but was significantly stimulated by exposure to either HIV-1$_{BaL}$ or HIV-1$_{BRU}$ (FIG. 13B).

Figure 13C:
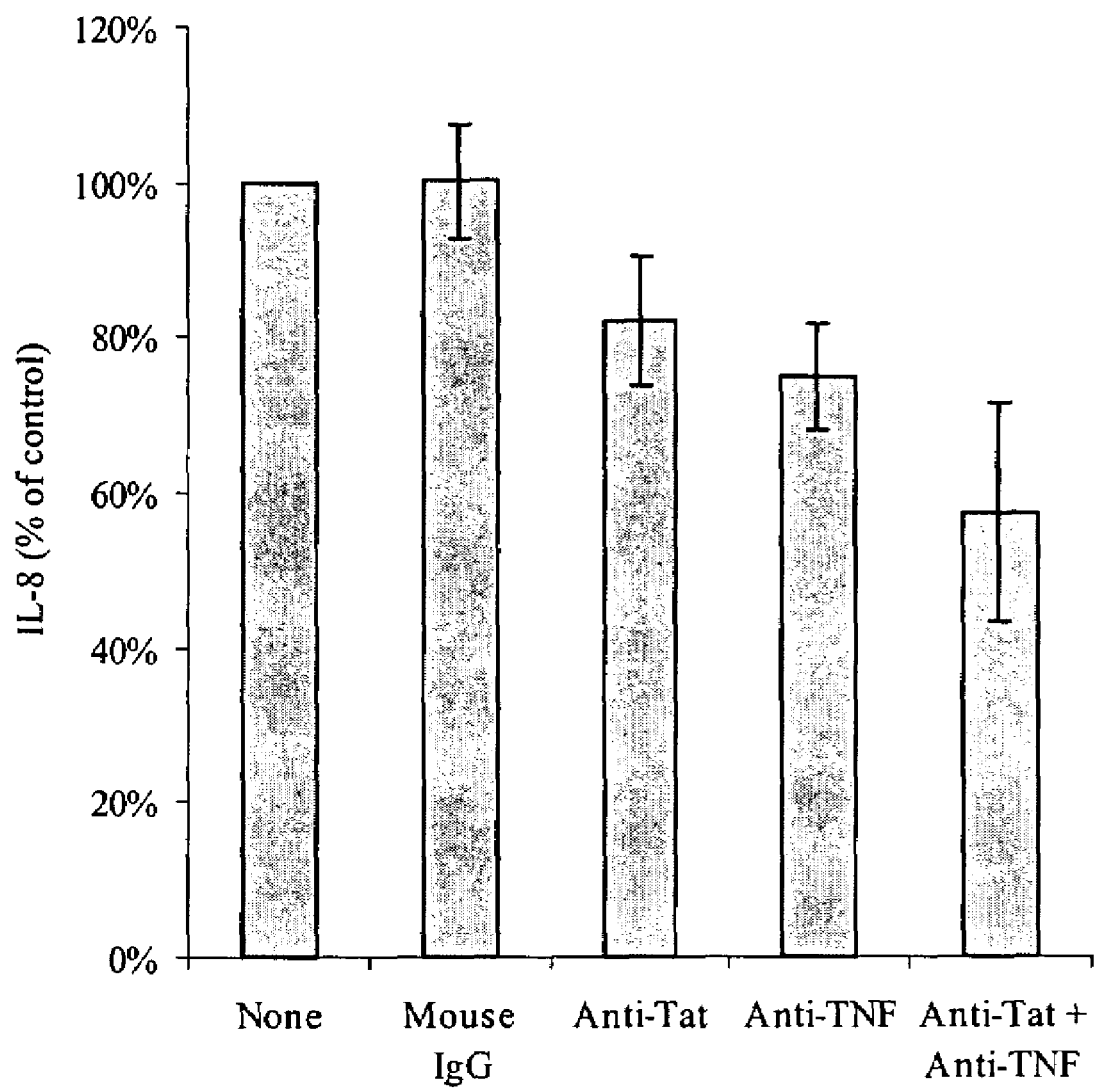
FIG. 13C. HIV-1 Tat triggers IL-8 production by MDM. Supernatants were collected 24 to 48 hours after infection and analyzed for IL-8 by ELISA. MDM were treated with antibodies (25 µg/ml) to Tat and TNF-α alone or in combination just prior to exposure to HIV-$1_{BRU}$. Data shown are the mean±SEM of two to five independent experiments for each antibody treatment, FIG. 14. HIV-1 Tat stimulates the IL-8 promoter in the presence of TNF-α.

In order to test whether Tat was responsible for the HIV-mediated increase in IL-8, MDM were incubated with antibodies known to neutralize Tat and the known inflammatory mediators TNF-α, IL-1, and IFN-γ prior to exposure to HIV-1. While immunodepletion of these cytokines did not significantly affect GRO-α production, these cytokines, and mainly TNF-α, regulate IL-8 production by HIV-1 (FIG. 13C). Anti-TNF-α significantly reduced IL-8 production alone and in combination with anti-Tat relative to control MDM (FIG. 13C). There was a trend toward decreased IL-8 following treatment with anti-Tat alone relative to control, and a significant decrease in IL-8 when anti-Tat was combined with anti-TNF-α relative to anti-TNF-α alone. These data suggest that the increase in IL-8 production by MDM in response to HIV-1 is mediated not only by gp120, but also by both TNF-α and Tat.

Figure 14:
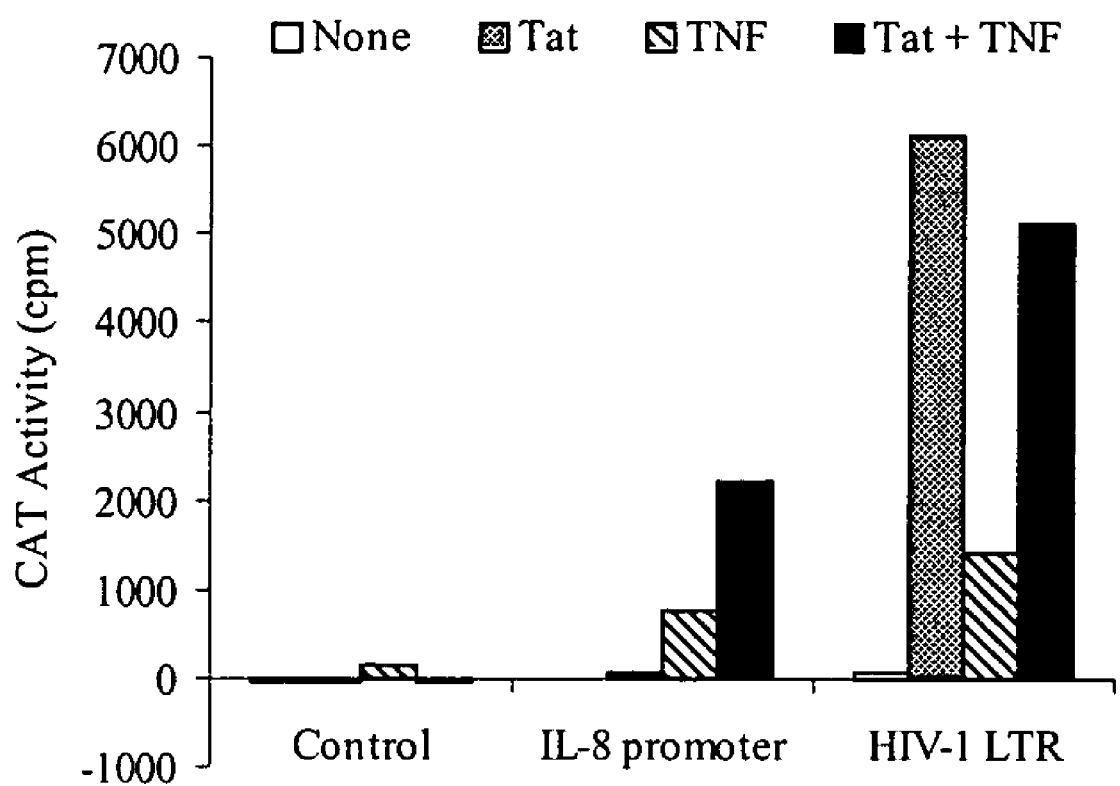

As HIV-1 Tat has been reported to act extracellularly by binding to integrin receptors, in addition to its intracellular effects on transcriptional elements, the mechanism by which Tat augments IL-8 production was investigated. Barillari, G. et al., *Proc Natl Acad Sci USA* 90, 7941–5 (1993); Ensoli, B. et al., *Nature* 345, 84–6 (1990); Ensoli, B. et al., *J Virol* 67, 277–87 (1993). The findings that IL-8 mRNA was elevated by HIV infection, and that IL-8 was regulated by Tat and TNF-α suggested the possibility that Tat might transactivate the IL-8 promoter. Therefore, transfection experiments using a construct containing the IL-8 promoter fused to a CAT reporter gene into the promonocyte cell line U937 were performed (FIG. 14). An HIV-1-LTR-CAT construct used previously to study transcriptional regulation of the HIV-1 LTR was used as a positive control for Tat activity Markovitz, D. M. et al., *J Virol* 66, 3961–5 (1992). While cotransfection of HIV-1 Tat alone increased the activity of the HIV-1-LTR, the IL-8 promoter was not affected. In contrast, the IL-8 promoter was activated when U937 cells were stimulated with a small concentration of TNF-α (1 ng/ml), and co-stimulation with Tat produced a three-fold increase in CAT activity above that produced by TNF-α stimulation alone. These data showing that stimulation of monocytic cells is required to see a Tat effect on the IL-8 promoter are in good agreement with findings indicating that, in T cells, the IL-8 promoter was responsive to Tat only after co-stimulation with CD3 and CD28 Ott, M. et al., *J Immunol* 160, 2872–80 (1998). The three-fold increase in IL-8 promoter activity in a monocytic cell line is similar to the increases detected at the level of IL-8 mRNA and protein in MDM. In contrast, the GRO promoter is not activated by Tat in the presence or absence of TNF-α, further confirming that Tat does not control GRO gene expression. Taken together, these experiments demonstrate that both Tat and TNF-α are necessary for the induction of IL-8 by HIV in monocytic cells.

Discussion

Elevated levels of IL-8 have been found previously in both the serum and tissues of individuals infected with HIV. Denis, M. et al., *AIDS Res Hum Retroviruses* 10, 1619–27 (1994); Matsumoto, T. et al., *Clin Exp Immunol* 93, 149–51 (1993). The HIV-1 Tat protein in isolation has been demonstrated to stimulate the release of IL-8 by PBL, brain-derived endothelial cells, and MDM, and HIV infection of MDM enhances IL-8 production. Esser, R. et al., *Blood* 91, 4752–60 (1998); Esser, R. et al., *Blood* 88, 3474–81 (1996);

Hofman, F. M. et al., *J Neuroimmunol* 94 28–39 (1999); Lafrenie, R. M. et al., *J Immunol* 159, 4077–83 (1997); Ott, M. et al., *J Immunol* 160, 2872–80 (1998). The data presented herein confirm earlier findings indicating that HIV triggers IL-8 release by MDM, and extend these findings by demonstrating that this effect is mediated by the viral proteins gp120 and Tat.

The presence of elevated levels of IL-8 in individuals infected with HIV has led several groups to suggest that IL-8 plays a role in HIV pathogenesis, but no prior evidence has been found to support these claims. Lafrenie, R. M. et al., *J Immunol* 159, 4077–83 (1997). Previous investigations of chemokine regulation of viral replication have found that IL-8 has either no effect or a modest inhibitory effect on HIV-1 replication Capobianchi, M. R. et al., *AIDS Res Hum Retroviruses* 14, 233–40 (1998); Mackewicz, C. E. et al., *Cell Immunol* 153, 329–43 (1994); Nagira, M. et al., *Virology* 264, 422–6 (1999). It is demonstrated herein that IL-8 stimulates viral replication in both MDM and activated T lymphocytes, findings that are somewhat at odds with those of previous investigators. In contrast to these previous studies, these experiments were performed with primary human macrophages and lymphocytes from a large number of individuals (n=17), and found an effect with amounts of IL-8 that are similar to the amounts of IL-8 found in the serum and tissues of HIV-infected individuals. The other investigators most likely did not detect an effect of IL-8 because the doses used were well above the optimal dose for IL-8 (5 to 125 ng/ml). That the concentrations used herein are the ones which are biologically relevant is confirmed by our finding that depletion of endogenous IL-8 markedly reduces HIV-1 replication. Therefore, it is now demonstrated for the first time a stimulatory effect of the chemokine IL-8 on HIV-1 replication in two important target cells of infection-lymphocytes and macrophages. Thus, HIV infection leads to elevated production of IL-8, which then completes a "vicious cycle" by in turn increasing HIV replication. This loop presents an attractive target for antiretroviral therapy.

The mechanisms by which HIV induces IL-8 production by MDM have now been further characterized. Previous findings with the C-X-C chemokine GRO-α suggested that HIV-1 may stimulate the release of IL-8 by engagement of CXCR4. Treatment of MDM with recombinant gp120 from either X4 HIV or R5 HIV enhances IL-8 production (FIG. 8A). However, while gp120 indeed induces IL-8 production, it cannot be the sole mechanism by which HIV acts. Antibodies that prevent gp120 interaction with the HIV coreceptor CXCR4 and inhibitors of CXCR4 signaling only diminish the stimulation of IL-8 seen with whole virus, while blocking CCR5 or CD4 have no effect.

Previous investigators have addressed the ability of HIV-1 Tat to stimulate IL-8 production by lymphocytes, endothelial cells, and MDM. Hofman, F. M. et al., *J Neuroimmunol* 94 28–39 (1999); Lafrenie, R. M. et al., J Immunol 159, 4077–83 (1997); Ott, M. et al., *J Immunol* 160, 2872–80 (1998). The experiments presented herein add that Tat induces IL-8 promoter activity in monocytic cells, but only in combination with TNF-α activation. The finding that stimulation of monocytic cells with TNF-α is required to see a Tat effect on the IL-8 promoter is novel and agrees with others' findings that, in T cells, the IL-8 promoter is responsive to Tat only after co-stimulation with CD3 and CD28. Ott, M. et al., *J Immunol* 160, 2872–80 (1998). The relevance of the Tat- and TNF-α-mediated induction of IL-8 was confirmed by immunodepletion experiments; antibodies that neutralize Tat and TNF-α significantly reduce IL-8 levels.

Methods

Reagents: Recombinant human IL-8, polyclonal antibodies to IL-8, IFN-γ, IL-1, and monoclonal antibodies to CXCR1, CXCR2, IL-8, and GRO-α were obtained from R&D Systems (Minneapolis, Minn.) and added as indicated in the figure legends. Neutralizing antibodies to TNF-α were used at a dilution of 1:200. Kasahara, K. et al., *J Leukoc Biol* 50 287–95 (1991). Lipopolysaccharide (LPS) from *E. coli* strain O55:B5 and all other chemicals were obtained from Sigma (St. Louis, Mo.).

Cell Lines: The promonocyte cell line U937 was cultured in RPMI+10% fetal bovine serum (FBS, GibcoBRL, Gaithersberg, Md.). Human Dermal Microvascular Endothelial Cells (HDMEC) were purchased from Clonetics (Walkersville, Md.) and Cell Systems Corp. (Kirkland, Wash.). HDMEC were plated on tissue culture flasks (Corning Inc., Corning, N.Y.) coated with 0.01% gelatin and were maintained in microvascular endothelial cell specific growth media (EGM-MV, Clonetics). BCBL-1, a body cavity based lymphoma cell line infected with KSHV/HHV8, was maintained in RPMI-1640+10% FBS and was used to propagate KSHV/HHV8 as described previously by Renne, R. et al., *Nat Med* 2, 342–6 (1996).

Isolation and Preparation of Human Monocyte-Derived Macrophages (MDM): MDM were prepared as described by Lane, B. R. et al., *Immunol* 163, 3653–3661 (1999). Briefly, heparinized venous blood was collected from healthy volunteers, and peripheral blood mononuclear cells (PBMC) were separated by Ficoll-Hypaque (Pharmacia Biotech AB, Uppsala, Sweden) density gradient centrifugation. MDM were purified by adherence to plastic for 2 h at 37° C. at a concentration of $5\times10^5$/ml. Adherent cells were consistently >90% monocytes as determined by Diff-Quik analysis and >85% CD14+ by flow cytometric staining with a PE-conjugated mouse anti-human monoclonal antibody to CD14 (M5E2; PharMingen, San Diego, Calif.), as well as >99% viable as determined by Trypan blue exclusion. MDM were cultured in DMEM supplemented with 10% FBS, 2 mM glutamine, 100 U/ml penicillin, and 100 µg/ml streptomycin for up to two weeks (typically 3 days) prior to infection with HIV-1. Peripheral blood lymphocytes (PBL) did not adhere to plastic and were collected from PBMC cultures. PBL were cultured at $1-2\times10^6$/ml in RPMI 1640 supplemented with 10% FBS, 2 mM glutamine, 100 U/ml penicillin, and 100 µg/ml streptomycin. PBL were stimulated with PHA (Sigma; 5 µg/ml) for 1 to 3 days and PHA-activated PBL were maintained in IL-2 (Hoffmann-La Roche, Nutley, N.J.; 40 U/ml) for the remainder of the time in culture.

Preparation of HIV-1 Stocks: All of the HIV-1 isolates used in this report were originally obtained from the NIH AIDS Reagent Program. Stocks of HIV-$1_{BaL}$ and HIV-$1_{ADA}$ were prepared by infection of HOS-CD4-CCR5 cells and of HIV-$1_{BRU}$ by infection of CEM-SS cells. For some experiments, viral stocks were prepared by infection of PHA-activated, CD8-depleted PBL; results were identical to those obtained using the cell line-derived viral isolates. Other viral stocks were used directly as provided by the NIH AIDS Reagent Program.

HIV-1 Infection of MDM and PBL: For each experiment, multiple wells of MDM or PBL were infected with equal RT counts of HIV-1 ($30-300\times10^6$ CPM of RT used per $10^5$ cells). This amount of CPM of RT activity per cell corresponds to a multiplicity of infection (MOI) of between 0.01 and 0.1 as determined by titration on HOS-CD4-CCR5 and CEM-SS cell lines and quantitation of proviral DNA in PBMC 24 h after infection. MDM were cultured for 3 d prior to infection, washed after an overnight incubation with the virus, and cultured in DME+10% FBS. PHA-activated PBL were washed and incubated in RPMI+10% FBS+IL-2 (40 U/ml) overnight. CD8+cells were depleted with magnetic Dynabeads® M-450 CD8 according to the manufacturer's instructions (Dynal, Lake Success, N.Y.). CD8-depleted PBL were then incubated with HIV-1 for 4 h, washed and incubated in media +IL-2. A portion of the media (25%) was removed from the MDM and PBL supernatants and replaced twice weekly.

Cytokine ELISAs: Cellular supernatants were collected and stored at −70° C. until analysis. Extracellular immunoreactive IL-8 and GRO-α were measured using a sandwich-type immunoassay (ELISA) with capture and biotinylated detection antibodies according to the manufacturer's instructions (R&D Systems). The lower limit of detection for these assays is 32 pg/ml. IL-8 was also evaluated using an in-house ELISA protocol as previously described. Evanoff, H. L. et al., *Immunol Invest* 21, 39–45 (1992); Lane, B. R. et al., *Immunol* 163, 3653–3661 (1999). This ELISA method consistently detected cytokine levels >50 pg/ml.

Reverse Transcriptase (RT) Assay: HIV replication was determined by quantification of the RT activity present in the supernatants using a poly(A)-oligo(dT) template primer as previously described. Potts, B. J. et al., *Virology* 175, 465–76 (1990). RT activity was assayed using $^{32}$P-labeled deoxythymidine triphosphate incorporated in DNA bound to DE81 paper (Whatman) and quantified using either the Series 400 PhosphorImager and ImageQuant® software (Molecular Dynamics, Sunnyvale, Calif.) or a Betascope radioisotope imaging system. RT activity is reported as phosphoimager counts except when labeled "counts" to signify beta counts. The absolute values varied between experiments, but peak activity consistently occurred 7 to 14 d post-infection of MDM and 4 to 7 d after infection of CD8-depleted PBL.

Evaluation of Lipopolysaccharide Content: LPS content was evaluated using the limulus amebocyte lysate test (Sigma) and found to be less than 0.16 EU/100 µl of the viral stocks, less than 0.016 EU/µg for recombinant HIV-1 Tat, and less than 0.23, 0.54, 1.6, and 1.6 EU/µg for recombinant gp120 from HIV-1 CM, 93TH975, LAV, and MN respectively.

Northern Blot Analysis of IL-8 mRNA: Total cellular RNA was extracted from uninfected and HIV-1$_{BRU}$-infected MDM with TRIzol (GibcoBRL) according to the manufacturer's instructions. Equal amounts of RNA were then analyzed for IL-8 gene expression by northern (RNA) blot analysis. Ethidium bromide-stained gels were photographed to demonstrate equivalent amounts of 28S and 18S rRNA in each sample. The IL-8 oligonucleotide probe was end-labeled by polynucleotide kinase with [γ-$^{32}$P] dATP. Strieter, R. M. et al., *Science* 243, 1467–9 (1989). Probe was annealed for 2.5 h at 68° C. in QuikHyb solution (Stratagene, La Jolla, Calif.). Hybridization and low-stringency wash were performed in accordance with the manufacturer's instructions. Quantitation of RNA was determined using a Series 400 PhosphorImager and ImageQuant® software.

Intracellular Cytokine Staining: PBMC were collected as described above and cultured in RPMI+10% FBS. The next day, PBMC were treated for 6 h with monensin (GolgiStop™, PharMingen) and incubated with virus or TNF-α. PBMC were then collected and stained for the presence of intracellular IL-8 and various cell surface markers according to the manufacturer's instructions (PharMingen). Adherent cells were collected by incubation in PBS+10 mM EDTA for 30 min at 4° C. PBMC (both adherent and non-adherent cells) were incubated in staining buffer (DPBS+1% FBS+ 0.09% sodium azide) with mouse IgG for 20 min at 4° C. to block non-specific binding of IgG to target cells. PBMC were then washed with staining buffer and stained for cell surface antigens for 30 min at 4° C. using R-phycoerythrin (PE)-conjugated mouse anti-human CD4 (PE-CD4) or CD14 (PE-CD14) monoclonal antibodies or PE-mouse IgG$_1$, κ isotype control immunoglobulin (PharMingen). After two washes with staining buffer, PBMC were fixed and permeabilized with Cytofix/Cytoperm (PharMingen). PBMC were washed twice in Perm/Wash solution and then stained with either fluorescein isothiocyanate (FITC)-conjugated mouse anti-human IL-8 monoclonal antibody or FITC-mouse IgG$_{2a}$, κ immunoglobulin isotype standard (PharMingen). Analysis of cell staining was performed using an EPICS Elite cell sorter (Beckman-Coulter, Fullerton, Calif.). The monocyte and lymphocyte subpopulations were gated first according to the pattern of forward scatter and side scatter and then by expression of CD14 (monocytes) or CD4 (lymphocytes).

Transfection of the U937 Promonocyte Cell Line: U937 cells were transfected by the DEAE-dextran method with 1 µg of HIV-1 Tat (pCG-Tat1) or control vector (pCG) and 10 µg of a plasmid containing the chloramphenicol acetyl transferase (CAT) reporter gene downstream of either sequence which lacks eukaryotic promoter and enhancer sequences (pCAT-Basic, Promega, Madison, Wis.), nucleotides −254 to +19 of the IL-8 promoter (pCAT-IL-8), or the HIV-1-LTR. The cells were either left untreated or treated with TNF-α (1 ng/ml) at 24 hours after transfection and harvested 48 hours after transfection. CAT activity was quantified and normalized for the amount of protein. Values near 6000 represent complete acetylation of chloramphenicol (100%).

Statistics: The data are representative of at least three experiments and are expressed as the mean of triplicate wells (±standard deviation) throughout unless otherwise noted. Statistical significance was evaluated by t-test for normally distributed data and by Wilcoxon signed ranks test for non-parametric data. A p value <0.05 (*) or <0.005 (**) was regarded as statistically significant.

SPECIFIC EXAMPLE 2

Effect of IL-8 on Kaposi's Sarcoma

Results

IL-8 Promotes Angiogenesis in an Animal Model of Kaposi's Sarcoma: The increase in production of IL-8, along with that of GRO-α, following HIV-1 infection of MDM led to the hypothesis that changes in the levels of these angiogenic, KSHV ORF 74-activating, C-X-C chemokines may create an angiogenic environment which would encourage the development and progression of KS in AIDS patients. In addition, HIV-1 Tat has long been known to be involved in the pathogenesis of Kaposi's sarcoma, and the present invention demonstrates that Tat stimulates IL-8 production by MDM. In order to investigate the prospective role of IL-8 in KS, an animal model of KS was developed in which human dermal microvascular endothelial cells (HDMEC) are infected with KSHV and then injected into the flank of SCID mice.

KSHV was harvested from the cell-free supernatants of PMA-stimulated BCBL-1 cells Friborg, J. Jr. et al., *J Virol* 72, 10073–82 (1998)) and used to infect HDMEC in vitro.

HDMEC cultured in endothelial cell specific growth media exhibit a typical cobblestone morphology (FIG. 15A, panel A). After incubation with lysates of either untreated or PMA-treated BCBL-1 cells, HDMEC display a spindle-shaped morphology, similar to that of the spindle cells present in KS lesions in vivo (FIG. 15A, panels B-D). BCBL-1 cell lysate-treated HDMEC became infected with KSHV and maintained viral genomes after multiple passages, as evidenced by PCR analysis of the 233 bp fragment (FIG. 15B) and cyclin D gene (FIG. 15C) of KSHV. In addition, treatment of HDMEC with PMA-stimulated BCBL-1 cell lysates stimulated cellular proliferation (FIG. 15D), but was not sufficient to transform HDMEC unless the cells were stably transfected with the anti-apoptotic protein Bcl-2. HDMEC that have been treated with the cell-free supernatants of PMA-stimulated BCBL-1 cells therefore are productively infected with KSHV and exhibit phenotypic characteristics and increased growth similar to the spindle cells present in KS lesions.

To investigate whether KSHV infection stimulates angiogenesis in vitro, the supernatants of KSHV-infected HDMEC were analyzed by an endothelial cell migration assay. Nor, J. E. et al., *Am J Pathol* 154, 375–84 (1999). Migration was standardized against recombinant IL-8, which could be depleted to less than 5% of its activity by an antibody that neutralizes IL-8 bioactivity (FIG. 16). While supernatants from uninfected HDMEC did not induce the migration of endothelial cells, the conditioned media from KSHV-infected HDMEC contained substantial migratory activity indicating a shift in the balance of angiogenic factors present. Hanahan, D. et al., *Cell* 86, 353–64 (1996). To determine the contribution of IL-8 and VEGF to the angiogenic activity present in supernatants of HDMEC infected with KSHV, antibodies to neutralize the activities of IL-8, GRO-α, or VEGF were added. The addition of anti-IL-8 or anti-GRO-α antibody markedly diminished the HDMEC migration, and addition of both antibodies eliminated almost all migratory activity (FIG. 32). In contrast, antibodies to VEGF did not affect migration of KSHV-infected HDMEC in this assay (FIG. 32). These studies suggest that IL-8 and GRO-α play important roles in the early angiogenic activity induced by KSHV infection, while VEGF plays little part in this activity.

Since the above experiments suggested that KSHV infection resulted in a shift in the normal angiogenic phenotype, IL-8 is a potent angiogenic factor, and KSHV has been demonstrated to encode a homolog of the human IL-8 receptors, it was postulated that IL-8 might be induced by KSHV infection, as it is by HIV infection. To test this hypothesis, we analyzed the supernatants of KSHV-infected HDMEC, which had been passaged multiple times, and uninfected parental HDMEC were analyzed for the presence of IL-8 and other angiogenic factors. IL-8 production was increased significantly in the KSHV-infected HDMEC relative to uninfected HDMEC (FIG. 17A). The production of VEGF and GRO-α were also increased in KSHV-infected HDMEC (FIG. 33). It was next examined whether KSHV and HIV-1 would combine to stimulate even greater IL-8 production by infected cells. Indeed, KSHV and HIV-1 synergize to induce IL-8 and GRO-α production by HDMEC alone and in co-cultures of HDMEC and MDM (FIG. 34A and B). Thus, in individuals infected with both viruses, HIV-1 (and HIV-1 Tat) may further augment IL-8 production, potentiating the pro-angiogenic effects of KSHV alone.

Since the above experiments suggested that KSHV infection resulted in a shift in the normal angiogenic phenotype, previous work showed that IL-8 is a potent angiogenic chemokine in chronic inflammation (Koch, A. E. et al., *Science* 258, 1798–801 (1992)), and that KSHV has been demonstrated to encode a homolog of the human IL-8 receptors, it was postulated that IL-8 may be induced by KSHV infection, as it is by HIV infection. To test this hypothesis, the 24-hour supernatants of 80–95% confluent KSHV-infected HDMEC and uninfected parental HDMEC were analyzed for the presence of IL-8 and other angiogenic factors after multiple passages. IL-8 production was increased significantly in the KSHV-infected HDMEC relative to uninfected HDMEC (FIG. 17A). The production of VEGF, which is thought to play an important role in the development of KS, and GRO-α was also increased in KSHV-infected HDMEC. Next, it was examined whether KSHV and HIV-1 would combine to stimulate even greater IL-8 production by infected cells. Indeed, KSHV and HIV-1 synergize to induce IL-8 production in co-cultures of HDMEC and MDM (FIG. 17B). Thus, in individuals infected with both viruses, HIV-1 (and HIV-1 Tat) may further augment IL-8 production, potentiating the pro-angiogenic effects of KSHV alone.

As IL-8 is induced by both KSHV and HIV, it was hypothesized that it may be responsible for the induction of endothelial cell migration by the conditioned media of KSHV-infected HDMEC. To determine the contribution of IL-8 and VEGF to the angiogenic activity induced following infection of HDMEC with KSHV, antibodies were added to neutralize the activities of IL-8 and VEGF. The anti-IL-8 antibody neutralized 40% of the angiogenic activity present in the supernatants from KSHV-infected-HDMEC, while the anti-VEGF antibody had almost no effect on endothelial cell migration (FIGS. 18A–D). These studies suggest that IL-8 plays an important role in the early angiogenic activity induced by KSHV infection, while VEGF plays little part in this activity.

In order to examine the role of IL-8 in the angiogenic phenotype of KSHV-infected lesions in vivo, a previously described SCID mouse model system of KS was used. Nor, J. E. et al., *Am J Pathol* 154, 375–84 (1999). HDMEC, which were either left uninfected or infected with KSHV, were cultured for at least five passages in vitro and then seeded into a PLA sponge and implanted into the flank of SCID mice. PLA sponges implanted with KSHV-infected HDMEC stimulate the migration of newly formed vessels into the transplanted tissue, whereas uninfected HDMEC do not (FIG. 18A). While implants containing KSHV-infected HDMEC stimulate angiogenesis, they do not induce tumor formation unless the HDMEC overexpress the oncogene Bcl-2. Immunostaining of the transplanted tissue shows in-growth of murine factor CD31-containing vessels (FIG. 18B). A significant increase in the number of new vessels was detected by counting the number of vessels in each transplanted tissue (FIG. 18C). In order to demonstrate the role of IL-8 and VEGF in the new vessel formation in this in vivo model of KS, antibodies were added that neutralize IL-8 or VEGF to the HDMEC-containing sponges prior to implantation. Administration of the anti-IL-8 antibody reduced the number of vessels staining positive for CD31 by greater than 50%, while the anti-VEGF antibody had little effect on the angiogenic response in the SCID mouse model system (FIG. 18D). Taken together, the data from KSHV-infected HDMEC and from the animal model demonstrate the involvement of IL-8 in the angiogenic phenotype of KS. As HIV-1 and HIV-1 Tat also stimulate MDM to produce IL-8, HIV-1 infection might contribute to the development of KS by shifting the balance of C-X-C chemokines to favor angiogenesis.

Discussion

The HIV-1 transactivator protein Tat is the HIV-1 protein with the strongest link to the pathogenesis of KS. Tat has been clearly implicated in the growth of KS cells, and in combination with inflammatory cytokines, is believed to drive the formation of KS lesions. Ensoli, B. et al., *Nature* 345, 84–6 (1990); Ensoli, B. et al., *Nature* 371, 674–80 (1994). In a paracrine fashion, extracellular Tat is able to bind to integrin receptors. Barillari, G. et al., *Proc Natl Acad Sci USA* 90, 7941–5 (1993); Ensoli, B. et al., *J Virol* 67, 277–87 (1993). Tat has recently been shown to stimulate intracellular signaling cascades activating NF-κB and leading to the production of several cytokines, including IL-8. Prakash, O. et al., *J Natl Cancer Inst* 92, 721–8 (2000). Studies have suggested that VEGF plays an important role in prolonging endothelial cell survival by inducing expression of the anti-apoptotic protein Bcl-2. Nor, J. E. et al., *Am J Pathol* 154, 375–84 (1999). Investigations of the role of VEGF have revealed that it is induced by inflammatory cytokines and acts in combination with bFGF in KS lesions. bFGF is a major mediator of angiogenesis in KS, and Tat can enhance its angiogenic activity on KS cells, but the mechanism of Tat's action in this regard is still unknown. Ensoli, B. et al., *Nature* 371, 674–80 (1994). It is demonstrated herein that IL-8 appears to play a central role in connecting HIV-1 Tat and KSHV to a pro-angiogenic environment which would favor the development of KS.

Endothelial cells were infected with KSHV, by treatment of HDMEC with lysates from PMA-stimulated BCBL-1 cells. This strategy has been employed recently by several groups (Miller, G. et al., *N Engl J Med* 334, 1292–7 (1996); Renne, R. et al., *Nat Med* 2, 342–6 (1996)), and herein establishes an infection lasting for at least 12 passages in culture, as determined by PCR of two KSHV genes, ORF 26 and viral cyclin D. KSHV infection of HDMEC induces a spindle-cell morphology and increased proliferation in these cells, but was not sufficient to transform HDMEC, as one other group has observed (Flore, O. et al., *Nature* 394, 588–92 (1998)), unless the cells were stably transfected with the anti-apoptotic protein. These data are in good agreement with a recent report documenting that long-term infection by KSHV and transformation required that endothelial cells be immortalized with HPV type 16 E6 and E7 (Moses, A. V. et al., *J Virol* 73, 6892–902 (1999)) and with a second report indicating that Bcl-2 is involved in transformation of KSHV-infected cells. Sgadari, C. et al., *J Immunol* 165, 509–17 (2000). Therefore, transformation of KSHV-infected cells appears to require both viral infection and an inhibition of programmed cell death.

Much work has demonstrated that new vessel growth, or angiogenesis, is required for tumor maintenance, growth, and metastasis. Hanahan, D. et al., *Cell* 86, 353–64 (1996). The data presented herein suggest that, as is the case with tumors of non-viral etiologies, angiogenesis precedes tumorigenesis in KS. Conditioned media from KSHV-infected HDMEC stimulates endothelial cell migration. Analysis of the supernatants of KSHV-infected endothelial cells revealed elevated levels of several angiogenic molecules, including IL-8. Immunodepletion of IL-8 from the conditioned media reduced the migratory activity by greater than 50% (FIGS. 18A–D). Although VEGF is clearly involved in the pathogenesis of KS, VEGF played little role in the early angiogenic phenotype induced by KSHV infection. Certainly, several cellular factors contribute to the growth and dissemination of KS, but, while not being bound by theory, IL-8 appears to be central to the early stages of angiogenesis in this disease.

HIV and KSHV might work together in vivo to induce an angiogenic phenotype via elevated levels of the proangiogenic factor IL-8, predisposing dually-infected individuals to malignancy. It is demonstrated here that HIV can potentiate the effect of KSHV on IL-8 production when HDMEC were co-cultured with MDM. Although there is some overlap in the cellular tropism of HIV and KSHV, co-infection of target cells has not been established. It has been postulated that viral proteins, such as HIV-1 Tat, may play a central role connecting HIV to the pathogenesis of KS, but the precise mechanisms by which Tat augments angiogenesis and transformation of KS cells is still unclear. It is demonstrated here that HIV-1 and Tat induce IL-8 production by macrophages, lymphocytes, and endothelial cells, and that this chemokine is important for the generation of the angiogenic phenotype that precedes transformation in KSHV-infected tissue.

Methods

KSHV/HHV8 Infection: BCBL-1 cells ($10^7$) that were left untreated, treated with PMA for 24 h, or for 48 h, were washed twice with RPMI-1640, and then resuspended in 1 ml EGM-MV. Cell lysates were prepared by freeze-thawing the cells 3 times in liquid $N_2$ and filtering them through a 0.45 μm membrane. KSHV-containing lysates were then added to a 25 mm flask containing HDMEC at 80–90% confluency. After 48 hours, infected cells were split and grown in EGM-MV. Serum-free conditioned media was collected from confluent cells after 24 h and concentrated and dialyzed against deionized water in a Centricon filter with a nominal molecular weight exclusion of $M_r$ 10,000 (Amicon, Bevery, Mass.). Total DNA present in the cellular lysates or supernatants were purified 4 passages after infection according to the manufacturer's instructions (Qiagen, San Clarita, Calif.).

Polymerase Chain Reaction (PCR): PCR was performed using primers that recognize and amplify a region within the KSHV gene sequence to yield a 233-bp fragment ($KS330_{233}$) of open reading frame (ORF) 26, as reported by (Chang, Y. et al., *Science* 266, 1865–9 (1994). The following primers were used: forward primer, 5'-AGC CGA AAG GAT TCC ATT GTG CTC-3'; reverse primer, 5'-TCC GTG TTG TCT ACG TCC AGA CGA TAT-3' (Chang, Y. et al., *Science* 266, 1865–9 (1994). PCR reaction mixtures (50 μl volume) were set up containing 0.25 μg of isolated DNA, 50 pmol of each primer, 200 μM of each deoxynucleotide triphosphate, 1.5 mM $MgCl_2$, 50 mM KCl, 20 mM tris-HCl (pH 8.4) and 2.5 U Taq DNA polymerase. DNA was amplified as follows: 94° C. for 3 minutes (1 cycle), 94° C. for 30 seconds, 72° C. for 2 minutes (40 cycles), 72° C. for 10 minutes (1 cycle). PCR products were electrophoresed through a 1% agarose gel containing ethidium bromide. PCR for KSHV specific viral cyclin D was performed as previously described. Davis, M. A. et al., *J Natl Cancer Inst* 89, 1868–74 (1997). As a positive control, DNA was isolated from PMA-treated BCBL-1 cells.

In Vitro Angiogenesis Assay: HDMEC were cultured in EGV-MV media, and used at passage 9, 10, or 11. To measure migration, cells were washed three times and incubated overnight in MCDB-131 media (GibcoBRL)+0.1% BSA, harvested, resuspended in MCDB-131+0.1% BSA, and plated at $1.75 \times 10^4$/well on the lower surface of a gelatinized 0.5 μm filter (Nucleopore Corp., Pleasation, Calif.) in an inverted modified Boyden chamber. After 1–2 h at 37° C., during which time the cells adhere to the filter, the chamber was reinverted, test substance was added to the top well, and the chamber incubated 3–4 h at 37° C. to allow migration. Chambers were then dissembled, membrane fixed and stained, and the number of cells that had migrated to the top of the filter in 10 high-power fields counted. MCDB-131 with 0.1% BSA was used as negative control and media with IL-8 (100 ng/ml) or VEGF (50 ng/ml) as positive controls. Each sample was tested in quadruplicate within an experiment, and each experiment was repeated at least twice. Endothelial cells treated in parallel showed no toxicity as monitored by trypan blue exclusion (Polverini et al., *Methods Enzymol* 198, 440–50 (1991)).

Sponge Implantation in SCID Mice: Porous poly (L-lactic acid) (PLA) sponges were fabricated as previously described (Kaufmann et al., *Cell Transplant* 6, 463–8 (1997)). Briefly, poly (L-lactic acid) (PLA, Aldrich Chemical Co., Inc., Milwaukee, Wis.) was dissolved in chloroform to yield a solution of 10% polymer (w: v), and 0.12 ml of this solution was loaded into Teflon cylinders packed with 0.4 g of sodium chloride particles. The solvent was allowed to evaporate and then the sponges were immersed for 16 hr in an aqueous solution containing 10 mg/ml of polyvinyl alcohol (Aldrich Chemical) in phosphate buffered saline (PBS). The sponges (measuring approximately 6 mm×6 mm×1 mm) with an average pore diameter of 180 μm were dried, lyophilized, and sterilized by exposure to gamma radiation. The sponges were then soaked in 100% ethanol for 2 h, washed 1 h in PBS, and then left overnight in fresh PBS. HDMEC or KSHV-infected HDMEC were grown to confluence in microvascular endothelial cell-specific media. Just before implantation, $1 \times 10^6$ HDMEC or KSHV-infected HDMEC were resuspended in a 1:1 mixture of EBM-MV: Matrigel® (Collaborative Biomedical Products, Cambridge, Mass.) and allowed to adsorb into the sponges. Greater than 90% of the seeded cells are ultimately delivered in vivo. Male SCID mice (CB.17.SCID, Taconic, Germantown, N.Y.), three to four weeks old were anesthetized with ketamine and xylazine and two sponges were implanted subcutaneously in the dorsal region of each mouse. At seven and fourteen days after implantation, mice were sacrificed and the sponges were retrieved, fixed overnight in 10% buffered formalin, dehydrated through graded ethanol, embedded in paraffin and mounted on Superfrost (Fisher Scientific, Pittsburgh, Pa.) glass slides for histologic examination. Three sponges each from four to five mice were evaluated for cell type at each time point.

CD31 Staining and Microvessel Assessment: Paraffin was removed from the sections with sequential dilutions of xylene and ethanol. The sections were then washed in FA buffer and treated with 0.5% trypsin+0.1% calcium chloride for 45 minutes at 37° C. for antigen retrieval. Seventy five microliters of rat anti-mouse CD31 (PECAM-1) (MEC13.3, PharMingen) at a concentration of 25 μg/ml was applied to sections for 1 hour at 37° C. and the anti-rat IgG Vectastain® Elite ABC Kit (Vector Laboratories, Inc., Burlingame, Calif.) was used according to the standard protocol. The endothelial cells were stained with 3-amino-9-ethyl carbazole (AEC) developing solution for about 7 minutes and then counterstained with hematoxylin for 1 min. Microvessels were quantitated by a modification of the method of Weidner, et al., that enumerates vessels in the most vascular portion of the injured tissue (granulation tissue). Weidner, N., *Breast Cancer Res Treat* 36, 169–80 (1995); Weidner, N. et al., *N Engl J Med* 324, 1–8 (1991). Sections were examined under low power (40× to 100×) to identify the regions of highest vessel density and vessels were then counted in each of 10 high power fields (HPF, 400×). A vessel lumen was not required for identification of a microvessel; cell clusters were also counted. Counts were then expressed as the total number of microvessels in 10 HPF.

SPECIFIC EXAMPLE 3

Effect of GRO-α on HIV Replication

Results

Production of GRO-α by monocyte-derived macrophages (MDM) exposed to HIV-1: MDM play a critical role in HIV pathogenesis as both producers of infectious HIV and sources of immunoregulatory factors. Gartner, S. et al., *Science* 233, 215–219 (1986); Herbein, G. et al., *Clin Exp Immunol* 95, 442–449 (1994); Meltzer, M. S. et al., *Annu Rev Immunol* 8, 169–194 (1990). In early experiments, the pattern of cytokine secretion by primary human MDM when exposed to HIV-1 was examined. Only modest increases in the cytokines TNF-α and the IL-1 receptor antagonist (IL-1ra) were detected one to three days after infection and no significant change in 12 other immunoregulatory molecules at this point in time. The levels of RANTES, MIP-1α, and MIP-1β were not elevated during the first 72 hours after infection, but increased in parallel with virus production by MDM at later timepoints. In contrast, a substantial increase in the production of the C-X-C chemokines GRO-α, GRO-γ, and IL-8, and the C-C chemokine MCP-1 were measured within 24 hours, and was maintained for greater than one week after exposure to HIV-1.

Next the chemokine production by MDM exposed to a prototypical R5 isolate of HIV (HIV-$1_{BaL}$) was compared with that by MDM exposed to the X4 isolate HIV-$1_{BRU}$. While exposure to R5 HIV or X4 HIV had similar effects on MCP-1 and IL-8 production by MDM, there was a striking difference in the production of the C-X-C chemokine GRO-a by MDM exposed to the X4 isolate HIV-$1_{BRU}$, compared with MDM exposed to the R5 isolate HIV-$1_{BaL}$ (FIG. 19A). Secreted GRO-α was elevated as early as 75 minutes after incubation with HIV-$1_{BRU}$ and remained elevated throughout the period of culture (up to 2 weeks), while MDM infected with HIV-$1_{BaL}$ produced only slightly more GRO-α than uninfected controls. Indeed, all X4 isolates of HIV-1 and HIV-2 were found to be more potent inducers of GRO-α production than any of the R5 isolates tested. MDM from 11 different healthy donors exposed to HIV-$1_{BRU}$ produced significantly more GRO-α (median value, 4.00 ng/ml) than MDM infected with HIV-$1_{BaL}$ (0.45 ng/ml, p=0.019) and uninfected controls (0.06 ng/ml, p<0.001) (FIG. 19C). Northern blot analysis revealed that exposure of MDM to HIV-1 increased steady-state GRO mRNA levels greater than 35-fold (FIG. 20). While HIV-$1_{BRU}$ stimulated far more GRO-α production than did HIV-$1_{BaL}$, no virus production was detectable in MDM exposed to HIV-$1_{BRU}$ even as late as 2 weeks after infection, while substantial HIV-1 was detected in MDM infected with HIV-$1_{BaL}$ a few days after infection (FIG. 19B). These data suggest that GRO-α production is independent of productive infection with HIV-1, and is more pronounced following exposure to viral isolates that use CXCR4 for entry.

GRO chemokine production by peripheral blood mononuclear cells (PBMC): In order to analyze the production of GRO by individual cells, the presence of GRO in PBMC stimulated with HIV-1 virions or viral proteins was observed by flow cytometry. Fresh PBMC were cultured overnight without PHA stimulation and then exposed to small numbers of HIV-1$_{BaL}$ or HIV-1$_{BRU}$ virions or the viral proteins gp120 or Tat. Staining after 6 hours revealed that GRO was present in a large percentage of monocytes treated with HIV-1$_{BRU}$, X4 gp120, or TNF-α, and in less than 10% of untreated monocytes or those treated with HIV-1$_{BaL}$ or Tat (FIGS. 21A–C). GRO proteins were detected in less than 5% of PBL in all treatment conditions (FIGS. 21A–C). In addition, no increase in GRO-α production by activated PBL was detectable by ELISA following exposure to either R5 or X4 isolates of HIV-1. Thus, as GRO-α production occurred well before the detection of virus in MDM infected with R5 HIV and in the absence of infection of MDM by X4 HIV (FIGS. 19A–C), and in more cells than could be infected by the titers of virus used, it was concluded that GRO-α production occurs by a mechanism that does not depend on completion of the viral lifecycle within the MDM. Moreover, because X4 isolates of HIV-1 stimulated GRO-α production to a far greater extent than R5 isolates, it was hypothesized that the interaction between HIV-1 gp120 and CXCR4 induces the signals necessary to upregulate GRO-α production.

Specificity of GRO-α production by MDM exposed to HIV-1: The ability of bacterial and viral antigens to stimulate the production of GRO-α by MDM was examined in order to further investigate the specificity of the response to HIV-1. While stimulation with lipopolysaccharide (LPS) from *E. coli* strain O111:B4 (up to 2 μg/ml) activated MDM as determined by an MTT-based assay for cellular activation, MDM treated with LPS did not produce increased amounts of GRO-α protein (FIG. 22A). Treatment with polymixin B (10 μg/ml) prevented the activation of MDM by LPS, but did not prevent the HIV-1$_{BRU}$-induced increases in GRO-α, indicating that GRO-α production was not due to LPS contamination of the viral stocks. In addition, viral stocks were found to be negative for detectable endotoxin using a Limulus amebocyte lysate test. Exposure to neither adenovirus nor Epstein-Barr virus (EBV) resulted in a significant increase in GRO-α production (FIG. 23). Thus, GRO-α is produced specifically in response to encounter with HIV, and not simply because the MDM are activated non-specifically by viral antigens or in response to bacterial LPS.

Engagement of CXCR4 by HIV-1 gp120 stimulates GRO-α production by MDM: Although MDM are not infected by X4 HIV under most circumstances, these cells do express CXCR4, in addition to CD4 and CCR5. Moriuchi, M. et al., *J Clin Invest* 102, 1540–1550 (1998); Simmons, G. et al., *J Virol* 72, 8453–8457 (1998); Schmidtmayerova, H. et al., *J Virol* 72, 4633–4642 (1998); Verani, A. et al., *J Immunol* 161, 2084–2088 (1998). In order to determine whether binding of HIV-1 to one of these specific receptors is required for the production of GRO-α by MDM, MDM were pre-incubated with antibodies known to block HIV binding to CXCR4, CCR5, or CD4 prior to infection with HIV-1 (FIGS. 24A–B). Neutralization of binding to CXCR4 by the anti-CXCR4 antibody 12G5 prevented the release of GRO-α by MDM exposed to HIV-1$_{BRU}$, HIV-1$_{HXB2}$, and HIV-1$_{BaL}$, while anti-CCR5 (2D7), anti-CD4, and control mouse IgG did not have a significant effect. The ability of anti-CXCR4 to block the small increase in GRO-a production induced by the R5 isolate HIV-1$_{BaL}$ suggests that this isolate has some moderate affinity for CXCR4, although it is not able to use this receptor to infect CXCR4+ T cell lines. Thus, the modest effect observed with HIV-1$_{BaL}$ is most likely attributable to interaction with CXCR4 as well, similar to the recent observation that the R5 isolate HIV-1$_{ADA}$ is able to signal via neuronal CXCR4. Zheng, J. et al., *J Neuroimmunol* 98, 185–200 (1999).

In order to confirm the role of gp120 engagement of CXCR4 in GRO-α production, it was determined whether incubation of monocytes and MDM with gp120 from X4 HIV would stimulate GRO-a production. GRO proteins were detected in greater than 55% of monocytes in response to X4-specific gp120, compared with <5% in response to Tat, as determined by intracellular cytokine analysis (FIGS. 21A–C). Treatment of MDM with recombinant gp120 from the X4 isolates HIV-1$_{IIIB}$ and HIV-1$_{MN}$, but not with gp120 from the R5 isolates HIV-1$_{93TH975}$ nor HIV-1$_{CM235}$, nor with HIV-1 Tat, significantly increased the production of GRO-α (FIG. 22A). Subsequent dose-response studies demonstrated that concentrations of gp120 as low as 100 ng/ml were able to increase GRO-α production by MDM. This concentration of envelope protein has previously been found in the serum of HIV-infected individuals, indicating that levels of gp120 present in vivo are sufficient to induce GRO-α production. Oh, S. K. et al., *J Acquired Immune Defic Syndr* 5, 251 (1992). In addition, the stimulation of GRO-α production by HIV-1$_{BRU}$ was resistant to heat inactivation at 56° for 30 minutes, but sensitive to boiling for 5 minutes, consistent with the notion that a relatively heat stable factor (e.g., gp120) is responsible for this effect. Clouse, K. A. et al., *J Immunol* 147, 2892–2901 (1991).

Neither the natural ligand for CXCR4, stromal cell-derived factor (SDF-1α), nor RANTES, which binds to CCR5 and CCR1, was able to stimulate GRO-α production (FIG. 22A). In addition, anti-CXCR4 (12G5) caused only a transient increase in GRO-α production. This suggests that it is not simply interaction with CXCR4, but specific aspects of the engagement of CXCR4 by gp120, which lead to the striking increase in GRO-α production. To further address the ability of X4 gp120 to signal the production of GRO-α, replication-incompetent HIV-1 were pseudotyped with glycoproteins from HIV-1 and vesicular stomatitis virus (VSV). Exposure of MDM to HIV-1 pseudotyped with X4 gp120 stimulated GRO-A production, while exposure to HIV-1 pseudotyped with the VSV glycoprotein (VSV-G) did not (FIG. 22B).

HIV-1$_{BRU}$-induced GRO-α production was not dependent on the prior production of pro-inflammatory cytokines, as levels of GRO-α were not diminished by incubation with neutralizing antibodies to TNF-α, IL-1, or IFN-γ. GRO-α production was sensitive to the protein tyrosine kinase (PTK) inhibitors genistein and herbimycin A and insensitive to the phosphatidylinositol 3-kinase (PI3K) inhibitor wortmannin. Although CXCR4 is coupled to G$_i$ proteins (Zheng, J. et al., *J Neuroimmunol* 98, 185–200 (1999)), HIV-1 induced GRO-α production was also insensitive to the G$_i$-protein inhibitor pertussis toxin (FIG. 25). Thus, the present invention has uncovered a new HIV-1 signaling pathway that is initiated by gp120 ligation of CXCR4 on MDM, is insensitive to pertussis toxin, involves PTKs, and leads to augmented GRO-a production.

GRO-α stimulates HIV-1 replication in primary human macrophages and lymphocytes: Increased chemokine production triggered by the ligation of CXCR4 on MDM by HIV-1 gp120 could either benefit or compromise the ability of the virus to replicate in its target cells (or have no effect). As certain chemokines (RANTES, MIP-1α, MIP-10, SDF-1α) have been demonstrated to play important roles in HIV-1 pathogenesis, mainly as inhibitors of viral entry, Cocchi, F. et al., *Science* 270, 1811–1815 (1995); Coffey, M. J. et al., *Am J Physiol* 272, L1025–1029 (1997); Bleul, C. C.

et al., *Nature* 382, 829–833 (1996); Oberlin, E., *Nature* 382, 833–835 (1996), the effect of GRO-α, and signaling through its receptor, CXCR2, on HIV replication in MDM and T lymphocytes was studied. Replication of the macrophage-tropic R5 isolate HIV-1$_{BaL}$ in MDM was augmented by the addition of exogenous GRO-α (FIGS. 26A–B). The dose response curve was bell-shaped, with maximal effect at 10 to 25 ng/ml (FIG. 26A). In experiments with MDM from 5 different donors, HIV-1$_{BaL}$ replication was increased 14-fold on average (range: 2- to 40-fold). The addition of an antibody that prevents GRO-α from interacting with CXCR2 blocked the stimulatory effect of GRO-α on HIV-1$_{BaL}$ replication in MDM (FIG. 26B). On its own, the anti-CXCR2 antibody had no significant effect on viral replication in MDM from some donors (FIG. 26A) and decreased replication in others. No viral replication was detected when MDM from multiple donors were infected with HIV-1$_{BRU}$ in the presence or absence of exogenous GRO-α, indicating that GRO-α does not confer susceptibility to productive infection with X4 HIV on MDM (FIG. 19B). In addition to the increase in viral replication seen in MDM with GRO-α treatment, HIV-1$_{BaL}$ replication in PBL was stimulated 5-fold on average (n=6; range: 2- to 8-fold) by the addition of GRO-α (FIG. 26C). Replication of the X4 isolate HIV-1$_{BRU}$ was also increased in PBL 2.4-fold on average (n=7; range: 0.9- to 4.2-fold; p=0.027) (FIG. 26D). GRO-α stimulated the replication of all isolates tested, including both R5 and X4 isolates of HIV-1 and HIV-2.

CXCR2, the receptor for GRO-α, is expressed on peripheral blood monocytes and lymphocytes: Although it has been questioned whether functional CXCR2 is present on mononuclear cells, recent studies have indicated that low levels of this receptor may indeed be present and capable of transmitting signals in T cells and monocytes. Ward, S. G. et al., *Immunity* 9, 1–11 (1998); Gerszten, R. E. et al., *Nature* 398, 718–723 (1999). Flow cytometric analyses indicate that CXCR2 is consistently expressed on a small percentage of PBL and a greater proportion of monocytes (FIG. 27). The greater expression of CXCR2 on monocytes than on PBL correlates well with the larger stimulatory effect of GRO-α on HIV-1 replication in MDM than in PBL. In addition, the expression of CXCR2 on MDM may be induced by HIV-1.

Endogenous GRO-α regulates HIV-1 replication in MDM: Because HIV-1 stimulates GRO-α production by MDM and exogenous GRO-α stimulated HIV replication in MDM, it was investigated whether endogenous GRO chemokine production is necessary for HIV-1 to replicate in these primary human cells. Indeed, addition of an antibody that neutralizes the activity of GRO-α, GRO-β, and GRO-γ (anti-GRO) markedly reduced HIV-1$_{BaL}$ replication in MDM (FIG. 28). Identical results were obtained using an antibody specific for GRO-α. These data indicate that endogenous, HIV-stimulated GRO production plays a role in activating viral replication in primary human MDM and point to the existence of an autocrine loop involving GRO-α and HIV-1 replication.

Discussion

The envelope protein gp120 allows HIV-1 to enter and productively infect MDM through interactions with CD4 and CCR5, and under some circumstances CXCR4. Moriuchi, M. et al., *J Clin Invest* 102, 1540–1550 (1998); Simmons, G. et al., *J Virol* 72, 8453–8457 (1998); Schmidtmayerova, H. et al., *J Virol* 72, 4633–4642 (1998); Verani, A. et al., *J Immunol* 161, 2084–2088 (1998). The present invention shows that HIV-1 gp120 interaction with CXCR4, independent of productive infection, induces signals that result in GRO-α production, which subsequently augments viral replication in both macrophages and T lymphocytes. Increases in the amount of GRO-α produced by MDM were detected as early as 75 minutes after exposure to X4 HIV. GRO-α was increased greater than 35-fold at the RNA level and an average of 70-fold at the protein level in response to the X4 isolate HIV-1$_{BRU}$, and only 7.5-fold in response to the macrophage-tropic R5 isolate HIV-1$_{BaL}$. GRO-α was also induced by recombinant gp120 from X4 HIV, but not from R5 HIV, and by replication-incompetent HIV-1 enveloped with X4 gp120, but not with the envelope protein of VSV (VSV-G). Moreover, GRO was detected intracellularly in the majority of monocytes (but not in lymphocytes) when exposed to low titers (m.o.i. <0.01) of HIV-1 or to recombinant HIV-1 gp120. GRO-α production was inhibited by pre-incubation with an antibody that prevents interaction with CXCR4 (12G5), and was not blocked by anti-CD4 or anti-CCR5 antibodies. GRO-a was not produced in response to other viral antigens, bacterial LPS, or the natural ligand for CXCR4, SDF-1α. These experiments indicate that GRO-α production is a specific response of MDM to encounter with X4 HIV.

Following exposure to HIV-1, GRO-α production by MDM was blocked by agents that interfere with the gp120-CXCR4 interaction and by the PTK inhibitors genistein and herbimycin A. Inhibitors of P13K (wortmannin) or G$_i$ proteins (pertussis toxin), however, had no effect on GRO-α production. Previous work has shown that pro-inflammatory cytokines (e.g., TNF-α) are released following interaction of HIV-1 gp120 with CD4 present on the surface of MDM and T lymphocytes. Merrill, J. E. et al., *J Virol* 63, 4404–4408 (1989); Clouse, K. A. et al., *J Immunol* 147, 2892–2901 (1991). In addition, CXCR4-specific binding by HIV-1 has been implicated in CD8+ T cell death mediated by release of TNF-α from MDM, an effect that, unlike GRO-α induction by gp120, could also be induced by SDF-1α and blocked by pertussis toxin. Herbein, G. et al., *Nature* 395, 189–194 (1998). The present invention has uncovered a new HIV-1 signaling pathway that is initiated by gp120 ligation of CXCR4 on MDM, is insensitive to pertussis toxin, involves PTKs, and leads to the production of the chemokine GRO-α.

The data presented herein indicate that GRO-α, a chemokine not previously suspected to play a role in HIV pathogenesis, is involved in an autocrine/paracrine loop controlling HIV-1 replication. It is demonstrated herein that exogenous GRO-α stimulates HIV-1 replication in both acutely infected primary human MDM and PBL. While the mechanism by which HIV replication is activated is not yet clear, our preliminary data suggest that GRO-α acts to enhance viral entry by increasing the surface expression of CCR5 and CXCR4. Importantly, it is shown herein that disruption of this autocrine loop by depletion of endogenous, HIV-induced GRO-α greatly reduces HIV replication in MDM. As HIV-1 evolves during the course of infection to use CXCR4 in addition to CCR5 for infection, GRO-α induced by X4 HIV could affect the replication of both R5 HIV and X4 HIV in infected individuals. The induction of GRO-α by CXCR4-using isolates of HIV-1 may contribute to the increased pathogenicity of these isolates and help to explain the increased viral replication and advanced clinical deterioration associated with the emergence of X4 HIV that often occurs some years after initial infection. Connor, R. I. et al., *J Exp Med* 185, 621–628 (1997). Consistent with this hypothesis, elevated levels of GRO-α have been detected in the bronchoalveolar lavage fluid of HIV-infected individuals with *Pneumocystis carinii* pneumonia. Villard, J. et al., *Am*

*J Respir Crit Care Med* 152, 1549–1554 (1995). In addition to effects on HIV replication, as GRO-α is angiogenic and can activate the KSHV GPCR orf 74, an increase in GRO-α following exposure to HIV may also affect the progression of AIDS-associated KS. Strieter, R. M. et al., *J Biol Chem* 270, 27348–27357 (1995); Luan, J. et al., *J Leukoc Biol* 62, 588–597 (1997); Gershengorn, M. C. et al., *J Clin Invest* 102, 1469–1472 (1998). Therefore, interventions targeting GRO-α and signaling through CXCR2 have the potential to offer new therapeutic approaches for patients infected with HIV.

Methods

Isolation and Preparation of Human Monocyte-Derived Macrophages (MDM) and Peripheral Blood Lymphocytes (PBL): MDM were prepared from the peripheral blood mononuclear cells (PBMC) of healthy volunteers as described previously. Lane, B. R. et al., *J Immunol* 163, 3653–3661 (1999). Adherent cells were consistently >90% monocytes as determined by Diff-Quik analysis and >85% CD14+by flow cytometric staining with a PE-conjugated mouse anti-human monoclonal antibody to CD14 (M5E2; PharMingen, San Diego, Calif.), as well as >99% viable as determined by Trypan blue exclusion. MDM were cultured in DMEM supplemented with 10% FBS, 2 mM glutamine, 100 U/ml penicillin, and 100 µg/ml streptomycin for up to two weeks (typically 3 days) prior to infection with HIV-1. Non-adherent cells (PBL) were collected and resuspended at 1–2×10$^6$/ml in RPMI 1640 supplemented with 10% FBS, 2 mM glutamine, 100 U/ml penicillin, and 100 µg/ml streptomycin. PBL were stimulated with PHA (Sigma, St. Louis, Mo.; 5 ug/ml) for 1 to 3 days and PHA-activated PBL were maintained in IL-2 (Hoffmann-La Roche, Nutley, N.J.; 40 U/ml).

Preparation of Viruses: All of the HIV-1 isolates used in this report were originally obtained from the NIH AIDS Research and Reference Reagent Program. Stocks of HIV-1$_{BaL}$ were prepared by infection of HOS-CD4-CCR5 cells and of HIV-1$_{BRU}$ by infection of CEM-SS cells. For some experiments, viral stocks were prepared by infection of PHA-activated, CD8-depleted PBL; results were identical to those obtained using the cell line-derived viral isolates. In order to generate envelope-pseudotyped, replication-incompetent HIV-1, 293 cells were transfected with ePLAP (10 µg), an HXB2-based HIV-1 provirus in which the env gene was replaced with the human placental alkaline phosphatase (PLAP) gene, along with 1 µg of a plasmid encoding the vesicular stomatitis virus (VSV) glycoprotein (VSV-G) or env from the X4 isolate HIV-1$_{HXB2}$, by the calcium-phosphate method. Supernatants were collected 2 days after transfection and found to contain infectious virus by RT assay and infection of T1 cells. The supernatants contained no detectable GRO-α and were used at a 1:2 dilution to infect MDM.

HIV-1 Infection of MDM and PBL: For each experiment, multiple wells of MDM or PBL were infected with equal RT counts of HIV-1 (30–300×10$^6$ CPM of RT used per 10$^5$ cells). This amount of CPM of RT activity per cell corresponds to a multiplicity of infection (MOI) of between 0.01 and 0.1 as determined by titration on HOS-CD4-CCR5 and CEM-SS cell lines and quantitation of proviral DNA in PBMC 24 h after infection. MDM were cultured for 3 days prior to infection, washed after an overnight incubation with the virus, and cultured in DMEM+10% FBS. PHA-activated PBL were washed and incubated in RPMI+10% FBS+IL-2 (40 U/ml) overnight. CD8+cells were depleted with magnetic Dynabeads® M-450 CD8 according to the manufacturer's instructions (Dynal, Lake Success, N.Y.). CD8-depleted PBL were then incubated with HIV-1 for 4 hours, washed and incubated in media +IL-2. A portion of the media (25%) was removed from the MDM and PBL supernatants and replaced twice weekly. Recombinant GRO-α and monoclonal antibodies to CXCR2 (MAB331), GRO (MAB276), and GRO-α (MAB275) were obtained from R&D Systems (Minneapolis, Minn.) and added as indicated in the figure legends. Antibodies capable of blocking HIV binding to CD4 (RPA-T4), CCR5 (2D7), and CXCR4 (12G5) were added as indicated (No azide/low endotoxin format®, PharMingen).

Cytokine ELISAs: Cellular supernatants were collected and stored at −70° C. until analysis. Extracellular immunoreactive GRO-α was measured using a sandwich-type immunoassay (ELISA) with capture (MAB275) and biotinylated detection (BAF275) antibodies according to the manufacturer's instructions (R&D Systems). The lower limit of detection for this assay is 8 pg/ml. GRO-α, as well as the other cytokines tested, was also evaluated using an in-house ELISA protocol as previously described (53, 54). Dilutions of recombinant human MCP-1, MIP-1α, MIP-1β, RANTES, IL-8, GRO-α, GRO-γ, ENA-78, NAP-2, IP-10, MIG, IL-1β, IL-1ra, IL-6, IL-10, IL-12, TGF-β, and TNF-α (R&D Systems), ranging from 1 pg/ml to 100 ng/ml, were used as standards. This ELISA method consistently detected cytokine levels >50 pg/ml.

Reverse Transcriptase (RT) Assay: HIV replication was determined by quantification of the RT activity present in the supernatants using a poly(A)-oligo(dT) template primer as previously described. Potts, B. J. et al., *Virology* 175, 465–476 (1990). RT activity was quantified using either a Series 400 PhosphorImager and ImageQuant® software (Molecular Dynamics, Sunnyvale, Calif.; FIG. 5) or a Betascope radioisotope imaging system (FIG. 1). The absolute values varied between experiments, but peak activity consistently occurred 7 to 14 days after infection of MDM and 4 to 7 days after infection of PBL.

Northern blot analysis of GRO-α mRNA: Total cellular RNA was extracted from non-infected and HIV-1$_{BRU}$-infected MDM with TRIzol (GibcoBRL, Rockville, Md.) according to the manufacturer's instructions. Equal amounts of RNA were then analyzed for GRO gene expression by northern (RNA) blot analysis. Ethidium bromide-stained gels were photographed to demonstrate equivalent amounts of 28S and 18S rRNA in each sample. The MGSA/GRO probe was digested with EcoRI and PstI (270 bp), gel-purified, and labeled by the random hexamer method with [α-$^{32}$P] dATP. Probe was annealed for 1 hour at 68° C. in QuikHyb solution (Stratagene, La Jolla, Calif.). Hybridization and high-stringency wash were performed in accordance with the manufacturer's instructions. Quantitation of RNA was determined using a Series 400 PhosphorImager and ImageQuant® software.

Intracellular cytokine staining: PBMC were collected as described above and cultured in RPMI+10% FBS. The next day, PBMC were treated for 6 h with monensin (GolgiStop™, PharMingen) and incubated with virus, viral proteins, or TNF-α as indicated in the figure legend. PBMC were then collected and stained for the presence of intracellular GRO according to the manufacturer's instructions (PharMingen). Adherent cells were collected by incubation in PBS+10 mM EDTA for 30 min at 4° C. PBMC (both adherent and non-adherent cells) were then incubated in staining buffer (DPBS+1% FBS+0.09% sodium azide) with mouse IgG for 20 min at 4° C. to block non-specific binding of IgG to target cells. After two washes with staining buffer, PBMC were fixed and permeabilized with Cytofix/Cytoperm (PharMingen). PBMC were washed twice in Perm/Wash solution and then stained with either R-phycoerythrin (PE)-conjugated mouse anti-human GRO monoclonal antibody (GRO-PE) or PE-mouse $IgG_1$, κ isotype control immunoglobulin (PharMingen). Analysis of cell staining was performed using an EPICS Elite cell sorter (Beckman-Coulter, Fullerton, Calif.). The monocyte and lymphocyte subpopulations were gated according to the pattern of forward scatter and side scatter.

Statistics: The data are expressed as the mean of triplicate wells (±standard deviation) throughout unless otherwise noted. Statistical significance was evaluated by t-test for normally distributed data and by Wilcoxon signed ranks test for non-parametric data. A p value <0.05 (*) or <0.005 (**) was regarded as statistically significant.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein including literature references and patents, are incorporated by reference as if fully set forth.

We claim:

1. A method of suppressing viral replication in a human patient having an HIV viral infection, the method comprising administering to the human patient having the HIV viral infection a therapeutically effective amount, to suppress HIV viral replication, of a non-peptide small molecule inhibitor which blocks or interferes with or prevents the binding of at least one C-X-C chemokine with at least one C-X-C chemokine receptor selected from the group consisting of CXCR1, CXCR2 and CXCR3.

2. The method of claim 1, wherein the non-peptide small molecule inhibitor is N-(2-hydroxy-4-nitrophenyl)-N'-(2-bromophenyl)urea.

3. The method of claim 1, wherein the C-X-C chemokine is selected from the group consisting of IL-8, GRO-α and IP-10.

4. A method of suppressing viral replication in a human patient having a viral infection, the method comprising administering to said human patient having a viral infection a therapeutically effective amount, to suppress viral replication, of a small molecule inhibitor which blocks, interferes with or prevents the binding of at least one C-X-C chemokine with at least one C-X-C chemokine receptor selected from the group consisting of CXCR1, CXCR2 and CXCR3; and wherein said small molecule inhibitor comprises N-(2-hydroxy-4-nitrophenyl)-N'-(2-bromophenyl)urea of formula (I):

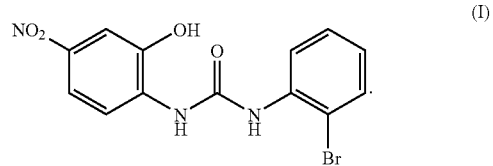

5. The method of claim 4, wherein said viral infection is an HIV infection.

* * * * *